US006075123A

United States Patent [19]
Lahti et al.

[11] Patent Number: 6,075,123
[45] Date of Patent: Jun. 13, 2000

[54] CYCLIN-C VARIANTS, AND DIAGNOSTIC AND THERAPEUTIC USES THEREOF

[75] Inventors: Jill M. Lahti; Vincent J. Kidd, both of Cordova, Tenn.

[73] Assignee: St. Jude Children's Research Hospital, Memphis, Tenn.

[21] Appl. No.: 08/867,381

[22] Filed: Jun. 2, 1997

Related U.S. Application Data

[60] Provisional application No. 60/018,614, Jun. 3, 1996.

[51] Int. Cl.[7] .......................... C07K 17/00; C07H 21/04; C12N 15/00
[52] U.S. Cl. .................... 530/350; 424/388.1; 536/23.1; 435/320.1
[58] Field of Search .................... 530/350; 424/388.1; 536/23.1; 435/320.1

[56] References Cited

FOREIGN PATENT DOCUMENTS 666270   8/1995   European Pat. Off. .
WO 93/24514   12/1993   WIPO .

OTHER PUBLICATIONS

Akoulitchev et al., Nature 377:557–560 (1995).
Betticher et al., Oncogene 11:1005–1011 (1995).
Caldas et al. Nature Gen. 8:27–32 (1994).
Cross, Science 267:1353–6 (1995).
Cross, Mol. Cell Biol. 10:6482–6490 (1990).
Demetrick et al., Cytogenet. Cell Genet. 69:190–192 (1995).
Desai et al., Mol. Biol. Cell, 3:572–582 (1992).
Gallant et al., J. Cell Biol. 117:213–224 (1992).
Gu et al., Science 265:103–106 (1994).
Guan et al., Genes & Devel. 8:2939–2952 (1994).
He et al., Cancer Res. 55:4833–4836 (1995).
He et al., Cancer Res. 54:5804–5807 (1994).
Hirai et al., Mol. Cell. Biol. 15:2672–2681 (1995).
Hussussian et al., Nature Gen. 8:15–21 (1994).
Kamb et al., Science 264:436–440 (1994).
Kamb et al. Nature Gen. 8:22–26 (1994).
Kato et al., Genes & Devel. 7:331–342 (1993).
Keyomarsi et al., Oncogene 11:941–50 (1995).
Koh et al., Nature 375:506–510 (1995).
Kowalczyk et al., Can. Genet. Cytogenet. 15:47–64 (1985).
Leclerc et al., Molec. Biol. Cell, 7:505–513 (1996).
Lee et al., Proc. Natl. Acad. Sci., USA 93:3859–3263 (1996).
Lee et al., Mol. Biol. Cell. 3:73–84 (1992).
Lees et al., Mol. Cell. Biol. 13:1194–1201 (1993).
Léopold et al. (1991) Cell 66:1207–16.
Lew et al. (1991) Cell 66:1197–206.
Li et al. Genomics, 32:253–259 (1996).
Li et al. Gene 153:237–242 (1995).
Liao et al., Nature 374:193–196 (1995).
Liu et al., Oncogene 10:1061–1067 (1995).
Lukas et al., Cancer Res. 55:4818–4823 (1995).
Lukas et al., Nature, 375:503–506 (1995).
Maldonado et al., Nature 381:86–89 (1996).
Medema et al., Proc. Natl. Acad. Sci., USA, 92:6289–6293 (1995).
Meloche et al. (Mol. Biol. Cell. 3:63–71 (1992).
Morgan, Nature 374:131–134 (1995).

(List continued on next page.)

*Primary Examiner*—Hankyel Park
*Attorney, Agent, or Firm*—Klauber & Jackson

[57] ABSTRACT

The present invention includes alternatively and partially spliced cyclin C mRNAs, recombinant DNA and the truncated protein (a truncated cyclin C) they encode. The alternatively spliced mRNAs result from an insertion of unique exons containing premature termination codons. The partially spliced mRNAs result from an insertion of additional coding sequence derived from exons. One aspect of the present invention is the demonstration that at least one of the alternatively spliced cyclin C mRNAs is produced in a cell cycle dependent fashion, as is the novel truncated cyclin box protein that it encodes. Truncated cyclin C acts as an endogenously encoded cyclin C inhibitor by negatively regulating cyclin C/cdk8 complex activity, in much the same way as the cyclin dependent protein kinase inhibitors that inhibit the D-type cyclins, cyclin A and cyclin E.

20 Claims, 15 Drawing Sheets

OTHER PUBLICATIONS

Ohtsubo et al., Mol. Cell. Biol. 15:2612–2624 (1995).
Okuda et al., Genomics 29:623–630 (1995).
O'Neill et al., Nature, 374:121–122 (1995).
Parker et al., Science 267:1024–7 (1995).
Parker et al., Proc. Natl. Acad. Sci., USA 89:2917–2921 (1992).
Parry et al., EMBO J., 14:503–511 (1995).
Pelech et al., TIBS 17:233–238 (1992).
Pietenpol et al., Cancer Res. 55:1206–1210 (1995).
Polyak et al., Genes & Devel. 8:9–22 (1994).
Prigogina et al., Can. Genet. cytogenet. 32:183–203 (1988).
Resnitzky et al., Mol. Cell. Biol., 14:1669–1679 (1994).
Rosenblatt et al., Proc. Natl. Acad. Sci. USA 89:2824–2828 (1992).
Serrano et al., Nature 366:704–707 (1993)xxxxxxxxx.
Sherr et al., Genes & Devel. 9:1149–1163 (1995).
Sherr, Cell 79:551–555 (1994).
Sherr, Cell 73:1059–1065 (1993).
Solomon et al. (1993) EMBO J., 12:3133–3142.
Tassan et al., Proc. Natl. Acad. Sci., USA 92: 8871–8875 (1995).
Jaskulski et al. (1988) Science 240: 1544–6.
Li et al. (1996) Oncogene 13:705–12.
Li et al. (1995) EMBL Sequence Database entry: Accession #U40873.-

FIG. 1A

```
  1     AATTCGCGGCCGCCGGCCGCGGCCCCGGGGGGCAGCGGAGGGCCCGGGGCCCCGTCCCACGGCTCCTCATGGCCGGAAACTTCTGGCAGAGCTCGCACTATTTACAATGGATTTTGGATAAACAAG
  1                                                          M  A  G  N  F  W  Q  S  S  H  Y  L  Q  W  I  L  D  K  Q  D
121     ATCTACTGAAGGAGCGCCAAAAAGACTTGAAATTTCTGTCTGAAGAAGAATATTGGAAGCTACAGATATTTTTACTAATGTTAGGTGTTATCCAGGCTTTAGGTGTGAACATCTTAAATTAAGACAAC
 21     L  L  K  E  R  Q  K  D  L  K  F  L  S  E  E  E  Y  W  K  L  Q  I  F  F  T  N  V  I  Q  A  L  G  E  H  L  K  L  R  Q
241     AAGTTATTGCCACTGCTACAGTCGTCTACTTCAAGAGATTCTATGCCAGATATTCCCTAAAAAGTATAGATCCAGTATTAATGGCTCCTACGTGTGTTTTGGCATCCAAAGTAGAG GAT
 61     V  I  A  T  A  T  V  V  Y  F  K  R  F  Y  A  R  Y  S  L  K  S  I  D  P  V  L  M  A  P  T  C  V  F  L  A  S  K  V  E  D
360     AAAACCAGCGCCACCTTATTGAAGCTCTTTTGACTGTTTTGTGTGTAGGTTGTTGGCAAACTAATCTTCAG GAGTTTGGTGTGTTTCAAATACAAGGTTGATTTCTGCTGCTACTTCT/
100     K  T  S  A  P  Y  *
```

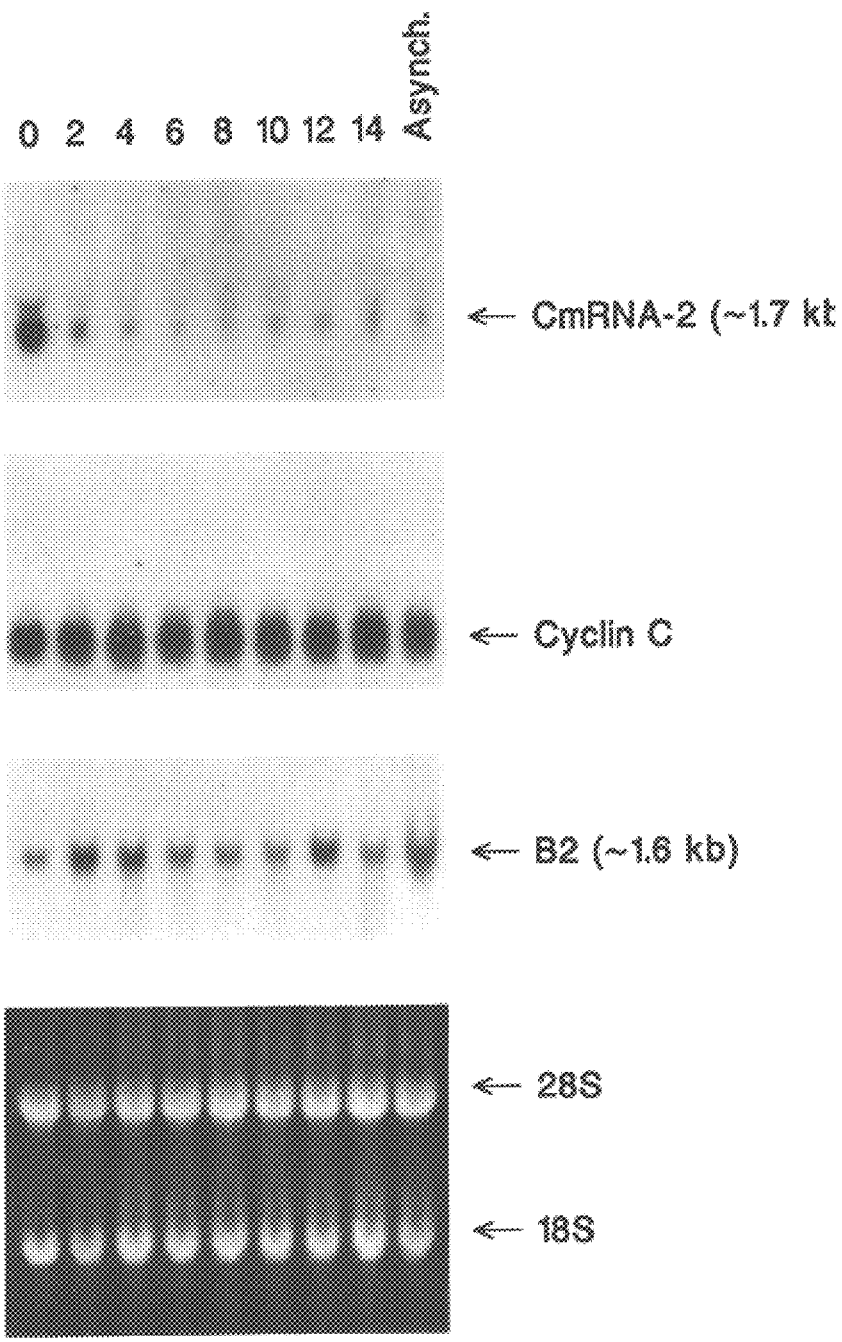

| | |
|---|---|
| 1 | MVAPRPLRRVVLFYQGKLCSMAGNFWQSSHYLQWILDKQD |
| 41 | LLKERQKDLKFLSEEEYWKLQIFFTNVIQALGEHLKLRQQ |
| 81 | VIATATVYFKRFYARYSLKSIDPVLMAPTCVFLASKVEEF |
| 121 | GVVSNTRLIAAATSVLKTRFSYAFPKEFPYRMNHILECEF |
| 161 | YLLELMDCCLIVYHPYRPLLQYVQDMGQEDMLLPLAWRIV |
| 201 | NDTYRTDLCLLYPPFMIALACLHVACVVQQKDARQWFAEL |
| 241 | SVDMEKILEIIRVILKLYEQWKNFDERKEMATILSKMPKP |
| 281 | KPPPNSEGEQGPNGSQNSSYSQS////////////////<br>-----RNSLSDKAIIYCKVTVKESRVQMEVRTLATANLKT |
| 321 | /////<br>FRRIP |

```
  1  gagcgcggttaccggacgggctggtctatggtcgctccgcgccgctcc
 51  gccgcgtggtgcttttatcaggcaagctgtgttccatgcagggaac
101  ttttggcagagctcccactatttgcaatggattttggataaacagatct
151  gttgaaggagcgccaaaaggatttaaagtttctcagaggagaatatt
201  ggaagttacaaatattttacaatgttatccaagcattaggtgaacat
251  cttaaattaagacaacaagttattgccactgctacggtatatttcaagag
301  attctatgccaggtattctctgaaaagtatagatcctgtattaatggctc
```

FIG.7B

```
351  ctacatgtgtgttttggcatccaagtagagaattggagtagtttca
351  ------------------------------------------
401  aatacaagattgattgctgctgctacttctgtattaaaactagatttc
401  ------------------------------------------
451  atatgcctttccaaggaatttccttataggatgaatcatatattagaat
451  ------------------------------------------
501  gtgaattctatctgttagaactaatggattgttgcttgatagtgtatcat
501  ------------------------------------------
551  ccttatagacctttgctcccagtatgtgcaggacatgggccaagaagacat
551  ------------------------------------------
601  gttgcttcccttgcatggaggatagtgaatgatacctacagaacggatc
601  ------------------------------------------
651  tttgcctactgtatcctccttttcatgatagctttagcttgcctacatgta
651  ------------------------------------------
```

FIG.7C

```
 701  gcctgtgttgtacagcagaaagatgccaggcaatgtttgctgagctttc
 751  tgtggatatggaaaagatttggaataatcaggttatttaaaactat
 801  atgagcagtggaagaatttcgatgagagaaagagatggcaaccattctt
 851  agtaagatgccaaaaccaaaccacctccaaaca//////////////
                                      ----gaaattccctgagtga
 901  /////////////////////gtgaaggagagcagggtccaaa
      taaggcaataatctattgcaaagttact-------------------
 951  tggaagtcagaactctagctacagccaatcttaaaacattccgaagaatt
1001  ccatag
```

1    MVAPRPLRRVVLFYQGKLCSMAGNFWQSSHYLQWILDKQD

41   LLKERQKDLKFLSEEEYWKLQIFFTNVIQALGEHLKLRQQ

81   VIATATVYFKRFYARYSLKSIDPVLMAPTCVFLASKVEEF

121  GVVSNTRLIAAATSVLKTRFSYAFPKEFPYRMNHILECEF

161  YLLELM///////////DCCLIVYHPYRPLLQYVQDMG
     ------VSKSSVINRLKHF*

201  QEDMLLPLAWRIVNDTYRTDLCLLYPPFMIALACLHVACV

241  VQQKDARQWFAELSVDMEKILEIIRVILKLYEQWKNFDER

281  KEMATILSKMPKPKPPPNSEGEQGPNGSQNSSYSQS

FIG.8

```
  1  gagcgcggttaccggacgggctgggtctatggtcgctccgcggccgctcc 51  gccgcgtggtgcttttttatcagggcaagctgtgttccatggcagggaac 101  ttttggcagagctcccactatttgcaatggatttttggataaacaagatct 151  gttgaaggagcgccaaaaggatttaaagtttctctcagaggaagaatatt 201  ggaagttacaaatattttttacaaatgttatccaagcattaggtgaacat 251  cttaaattaagacaacaagttattgccactgctacggtatatttcaagag 301  attctatgccaggtattctctgaaaagtatagatcctgtattaatggctc 351  ctacatgtgtgtttttggcatccaaagtagaggaatttggagtagtttca 401  aatacaagattgattgctgctgctacttctgtattaaaaactagattttc 451  atatgcctttccaaaggaatttccttataggatgaatcatatattagaat Exon 7
501  gtgaattctatctgttagaactaatg//////////////////////
     ------------------------gtaagtaaatcttctgtgattaat ////////////////////////////////////////////////
     agattaaaacattttttaaattaaatgaagttggaaattatttaaagaaat ////////////////////////////////////////////////
     gattttagagaggtacatttttaaaaccatccacctaatatgtgatggtga ////////////////////////////////////////////////
     aatcatggtagcctatttatattagcacctagagtctctctgaagcctgt
```

FIG.9A

```
///////////////////////////////////////////////
aaaataatttgtatatcctacttaggatgggaaaattttctgttctata ///////////////////////////////////////////////
gtaagtaactataatgaaaggattacaaacagacaagtcaggacattaaa ///////////////////////////////////////////////
ccaccataaattatgtgcacaatttgtgtgtgcgtgcagtgttatttaaa ////    ::::::::::
gata    ::::::::::

Exon 8
527 gattgttgcttgatagtgtatcatccttatagacctttgctccagtatgtg
    :::::::::::::::::::::::::::::::::::::::::::::::::

caggacatgggccaagaagacatgttgcttccccttgcat:::::::::::
    :::::::::::::::::::::::::::::::::::::::::::::::::

///////////////////////////////////////////////
aaaccattctaatattctgttccataaatatacctattaaaattaatttt ///////////////////////////////////////////////
ataacaaaacacagactgtaaacataaaaattaaggacaagttntcttta ///////////////////////////////////////////////
aagtaatcaggatacttttggtagtctgcaaacatacatataaatttac ///////////////////////////////////////////////
tgtataatttctggttttttaatttgatttttctgattttaaaaaatta ///////////////////////////////////////////////
gaaaaatgtgtttataatttgttatgagattttgaaatttaaaatatatt ///////////////////////////////////////////////
tagctgtaattttattcattgatatgtgcttatttgttgtcacattcatg ///////////////////////////////////////////////
tatccatccttttgccttgatgttttcacttttatagctgtgcttcagta ///////////////////////////////////////////////
gtataaaaggaaataaatgtgtgcaaagatgggaaatctggccctctctg ///////////////////////////////////////////////
gaggaaatatacaatcagatgaggtagttctgctttcagtaataatatga
```

FIG.9B

///////////////
tttacatttctata

Exon 9
590 ggaggatagtgaatgatacctacagaacggatc 622 tttgcctactgtatcctcctttcatgatagctttagcttgcctacatgta 673 gcctgtgttgtacagcagaaagatgccaggcaatggtttgctgagctttc 724 tgtggatatggaaaagattttggaaataatcagggttattttaaaactat 775 atgagcagtggaagaatttcgatgagagaaagagatggcaaccattctt 826 agtaagatgccaaaaccaaaaccacctccaaacagtcaaggagagcaggg 877 tccaaataaggcaataatctattgcaaagttacttggaagtcagaactct 928 agctacagccaatcttaa

SEQUENCE LISTING (1) GENERAL INFORMATION:

(iii) NUMBER OF SEQUENCES: 53

(2) INFORMATION FOR SEQ ID NO:1:

(i) SEQUENCE CHARACTERISTICS:
        (A) LENGTH: 1200 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (xi) SEQUENCE DESCRIPTION: SEQ ID NO:1:

```
AATTCGCGGC CGCCGGCCGC GGCCGGGGCA GCGGAGGGCC CGGGCCCGTC CCACGGCTCC        60

TCATGGCCGG GAACTTCTGG CAGAGCTCGC ACTATTTACA ATGGATTTTG GATAAACAAG       120

ATCTACTGAA GGAGCGCCAA AAAGACTTGA AATTTCTGTC TGAAGAAGAA TATTGGAAGC       180

TACAGATATT TTTTACTAAT GTTATCCAGG CTTTAGGTGA ACATCTTAAA TTAAGACAAC       240

AAGTTATTGC CACTGCTACA GTCTACTTCA AGAGATTCTA TGCCAGATAT TCCCTAAAAA       300

GTATAGATCC AGTATTAATG GCTCCTACGT GTGTGTTTTT GGCATCCAAA GTAGAGGAGT       360

TTGGTGTTGT TTCAAATACA AGGTTGATTT CTGCTGCTAC TTCTGTATTG AAAACTAGGT       420

TTTCATATGC CTTCCCGAAG GAGTTTCCTT ATAGGATGAA CCATATACTA GAATGTGAAT       480

TCTATCTCTT AGAATTAATG GACTGCTGTT TGATAGTGTA TCATCCTTAC AGACCTTTGC       540

TCCAATATGT GCAAGATATG GGCCAAGAAG ACATGCTGCT ACCTCTTGCT TGGAGGATAG       600

TGAATGACAC ATATAGAACT GATCTTTGTC TGCTGTACCC TCCTTTCATG ATAGCTCTAG       660

CTTGCCTACA CGTGGCCTGT GTTGTCCAGC AGAAGGATGC AAGGCAATGG TTTGCTGAGC       720

TATCTGTTGA TATGGAAAAG ATTTTAGAAA TAATCAGGGT TATTCTGAAG CTGTATGAGC       780

AGTGGAAGAA CTTTGATGAG AGGAAAGAGA TGGCTACTAT TCTTAGCAAA ATGCCTAAAC       840

CAAAACCACC TCCAAACAGT GAAGGAGAAC AGGGTCCAAA TGGTAGCCAG AACTCTAGTT       900

ATAGCCAATC TTAAGACATT CCAAAGAATT TCTTTACGGA CCACTTTGAC TCAAGACATC       960

CTGGGATCTT TCCTGTGTTC ATGAAATGGA CGGAATTTTT TTAATAACAT CTTTGACAAA      1020

GAACTTAAAG AGTAAATAGC TTGTTTGTGT CAAGCATTTT GGAAGTTTTT TATTTAAAAC      1080
```

```
TGCATCATTT TCTCTGAGGC TGGAGCAAAC GTACTAAGAT TTCTCAGTGT AAGGAATCAA      1140

ATGTTAAACC AAGCTGCGAA AGGGTAACGC TATCCACTCT AAAACAAATA GTTCATTACT      1200
```

(2) INFORMATION FOR SEQ ID NO:2:

(i) SEQUENCE CHARACTERISTICS:
        (A) LENGTH: 477 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (xi) SEQUENCE DESCRIPTION: SEQ ID NO:2:

```
AATTCGCGGC CGCCGGCCGC GGCCGGGGCA GCGGAGGGCC CGGGCCCGTC CCACGGCTCC        60

TCATGGCCGG GAACTTCTGG CAGAGCTCGC ACTATTTACA ATGGATTTTG GATAAACAAG       120

ATCTACTGAA GGAGCGCCAA AAAGACTTGA AATTTCTGTC TGAAGAAGAA TATTGGAAGC       180

TACAGATATT TTTTACTAAT GTTATCCAGG CTTTAGGTGA ACATCTTAAA TTAAGACAAC       240

AAGTTATTGC CACTGCTACA GTCTACTTCA AGAGATTCTA TGCCAGATAT TCCCTAAAAA       300

GTATAGATCC AGTATTAATG GCTCCTACGT GTGTGTTTTT GGCATCCAAA GTAGAGGATA       360

AAACCAGCGC ACCTTATTGA AGCTCTTTTG ACTGTTTTGT GTGTAGGTTG TTGGCAAACT       420

AATCTTCAGG AGTTTGGTGT TGTTTCAAAT ACAAGGTTGA TTTCTGCTGC TACTTCT         477
```

(2) INFORMATION FOR SEQ ID NO:3:

(i) SEQUENCE CHARACTERISTICS:
        (A) LENGTH: 283 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE:

(xi) SEQUENCE DESCRIPTION: SEQ ID NO:3:

```
Met Ala Gly Asn Phe Trp Gln Ser Ser His Tyr Leu Gln Trp Ile Leu
1               5                   10                  15

Asp Lys Gln Asp Leu Leu Lys Glu Arg Gln Lys Asp Leu Lys Phe Leu
            20                  25                  30

Ser Glu Glu Glu Tyr Trp Lys Leu Gln Ile Phe Phe Thr Asn Val Ile
        35                  40                  45

Gln Ala Leu Gly Glu His Leu Lys Leu Arg Gln Gln Val Ile Ala Thr
    50                  55                  60

Ala Thr Val Tyr Phe Lys Arg Phe Tyr Ala Arg Tyr Ser Leu Lys Ser
65                  70                  75                  80

Ile Asp Pro Val Leu Met Ala Pro Thr Cys Val Phe Leu Ala Ser Lys
                85                  90                  95

Val Glu Glu Phe Gly Val Val Ser Asn Thr Arg Leu Ile Ser Ala Ala
            100                 105                 110

Thr Ser Val Leu Lys Thr Arg Phe Ser Tyr Ala Phe Pro Lys Glu Phe
        115                 120                 125

Pro Tyr Arg Met Asn His Ile Leu Glu Cys Glu Phe Tyr Leu Leu Glu
    130                 135                 140
```

Leu Met Asp Cys Cys Leu Ile Val Tyr His Pro Tyr Arg Pro Leu Leu
145                 150                 155                 160

Gln Tyr Val Gln Asp Met Gly Gln Glu Asp Met Leu Leu Pro Leu Ala
            165                 170                 175

Trp Arg Ile Val Asn Asp Thr Tyr Arg Thr Asp Leu Cys Leu Leu Tyr
            180                 185                 190

Pro Pro Phe Met Ile Ala Leu Ala Cys Leu His Val Ala Cys Val Val
            195                 200                 205

Gln Gln Lys Asp Ala Arg Gln Trp Phe Ala Glu Leu Ser Val Asp Met
210                 215                 220

Glu Lys Ile Leu Glu Ile Ile Arg Val Ile Leu Lys Leu Tyr Glu Gln
225                 230                 235                 240

Trp Lys Asn Phe Asp Glu Arg Lys Glu Met Ala Thr Ile Leu Ser Lys
            245                 250                 255

Met Pro Lys Pro Lys Pro Pro Asn Ser Glu Gly Glu Gln Gly Pro
            260                 265                 270

Asn Gly Ser Gln Asn Ser Ser Tyr Ser Gln Ser
            275                 280

(2) INFORMATION FOR SEQ ID NO:4:

(i) SEQUENCE CHARACTERISTICS:
        (A) LENGTH: 105 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE:

(xi) SEQUENCE DESCRIPTION: SEQ ID NO:4:

Met Ala Gly Asn Phe Trp Gln Ser Ser His Tyr Leu Gln Trp Ile Leu
1               5                   10                  15

Asp Lys Gln Asp Leu Leu Lys Glu Arg Gln Lys Asp Leu Lys Phe Leu
            20                  25                  30

Ser Glu Glu Glu Tyr Trp Lys Leu Gln Ile Phe Phe Thr Asn Val Ile
            35                  40                  45

Gln Ala Leu Gly Glu His Leu Lys Leu Arg Gln Gln Val Ile Ala Thr
50                  55                  60

Ala Thr Val Tyr Phe Lys Arg Phe Tyr Ala Arg Tyr Ser Leu Lys Ser
65                  70                  75                  80

Ile Asp Pro Val Leu Met Ala Pro Thr Cys Val Phe Leu Ala Ser Lys
            85                  90                  95

Val Glu Asp Lys Thr Ser Ala Pro Tyr
            100                 105

(2) INFORMATION FOR SEQ ID NO:5:

(i) SEQUENCE CHARACTERISTICS:
        (A) LENGTH: 303 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE:

(vi) ORIGINAL SOURCE:
    (A) ORGANISM: Homo sapiens (xi) SEQUENCE DESCRIPTION: SEQ ID NO:5:

```
Met Val Ala Pro Arg Pro Leu Arg Arg Val Val Leu Phe Tyr Gln Gly
1               5                   10                  15

Lys Leu Cys Ser Met Ala Gly Asn Phe Trp Gln Ser Ser His Tyr Leu
            20                  25                  30

Gln Trp Ile Leu Asp Lys Gln Asp Leu Leu Lys Glu Arg Gln Lys Asp
        35                  40                  45

Leu Lys Phe Leu Ser Glu Glu Tyr Trp Lys Leu Gln Ile Phe Phe
    50                  55                  60

Thr Asn Val Ile Gln Ala Leu Gly Glu His Leu Lys Leu Arg Gln Gln
65                  70                  75                  80

Val Ile Ala Thr Ala Thr Val Tyr Phe Lys Arg Phe Tyr Ala Arg Tyr
                85                  90                  95

Ser Leu Lys Ser Ile Asp Pro Val Leu Met Ala Pro Thr Cys Val Phe
            100                 105                 110

Leu Ala Ser Lys Val Glu Glu Phe Gly Val Val Ser Asn Thr Arg Leu
        115                 120                 125

Ile Ala Ala Thr Ser Val Leu Lys Thr Arg Phe Ser Tyr Ala Phe
    130                 135                 140

Pro Lys Glu Phe Pro Tyr Arg Met Asn His Ile Leu Glu Cys Glu Phe
145                 150                 155                 160

Tyr Leu Leu Glu Leu Met Asp Cys Cys Leu Ile Val Tyr His Pro Tyr
                165                 170                 175

Arg Pro Leu Leu Gln Tyr Val Gln Asp Met Gly Gln Glu Asp Met Leu
            180                 185                 190

Leu Pro Leu Ala Trp Arg Ile Val Asn Asp Thr Tyr Arg Thr Asp Leu
        195                 200                 205

Cys Leu Leu Tyr Pro Pro Phe Met Ile Ala Leu Ala Cys Leu His Val
    210                 215                 220

Ala Cys Val Val Gln Gln Lys Asp Ala Arg Gln Trp Phe Ala Glu Leu
225                 230                 235                 240

Ser Val Asp Met Glu Lys Ile Leu Glu Ile Ile Arg Val Ile Leu Lys
                245                 250                 255

Leu Tyr Glu Gln Trp Lys Asn Phe Asp Glu Arg Lys Glu Met Ala Thr
            260                 265                 270

Ile Leu Ser Lys Met Pro Lys Pro Lys Pro Pro Asn Ser Glu Gly
        275                 280                 285

Glu Gln Gly Pro Asn Gly Ser Gln Asn Ser Ser Tyr Ser Gln Ser
290                 295                 300
```

(2) INFORMATION FOR SEQ ID NO:6:

(i) SEQUENCE CHARACTERISTICS:
        (A) LENGTH: 267 amino acids
        (B) TYPE: amino acid
        (C) STRANDEDNESS: single
        (D) TOPOLOGY: linear (ii) MOLECULE TYPE: protein (iii) HYPOTHETICAL: NO (v) FRAGMENT TYPE:

(vi) ORIGINAL SOURCE:
    (A) ORGANISM: Drosophila melanogaster (xi) SEQUENCE DESCRIPTION: SEQ ID NO:6:

Met Ala Gly Asn Phe Trp Gln Ser Ser His Ser Gln Gln Trp Ile Leu
1               5                   10                  15

Asp Lys Pro Asp Leu Leu Arg Glu Arg Gln His Asp Leu Leu Ala Leu
            20                  25                  30

Asn Glu Asp Glu Tyr Gln Lys Val Phe Ile Phe Ala Asn Val Ile
            35                  40                  45

Gln Val Leu Gly Glu Gln Leu Lys Leu Arg Gln Gln Val Ile Ala Thr
50                      55                  60

Ala Thr Val Tyr Phe Lys Arg Phe Tyr Ala Arg Asn Ser Leu Lys Asn
65                  70                  75                  80

Ile Asp Pro Leu Leu Leu Ala Pro Thr Cys Ile Leu Leu Ala Ser Lys
                85                  90                  95

Val Glu Glu Phe Gly Val Ile Ser Asn Ser Arg Leu Ile Ser Ile Cys
            100                 105                 110

Gln Ser Ala Ile Lys Thr Lys Phe Ser Tyr Ala Tyr Ala Gln Glu Phe
            115                 120                 125

Pro Tyr Arg Thr Asn His Ile Leu Glu Cys Glu Phe Tyr Leu Leu Glu
130                 135                 140

Asn Leu Asp Cys Cys Leu Ile Val Tyr Gln Pro Tyr Arg Pro Leu Leu
145                 150                 155                 160

Gln Leu Val Gln Asp Met Gly Gln Glu Asp Gln Leu Leu Thr Leu Ser
                165                 170                 175

Trp Arg Ile Val Asn Asp Ser Leu Arg Thr Asp Val Cys Leu Leu Tyr
            180                 185                 190

Pro Pro Tyr Gln Ile Ala Ile Ala Cys Leu Gln Ile Ala Cys Val Ile
            195                 200                 205

Leu Gln Lys Asp Ala Thr Lys Gln Trp Phe Ala Glu Leu Asn Val Asp
210                 215                 220

Leu Asp Lys Val Gln Glu Ile Val Arg Ala Ile Val Asn Leu Tyr Glu
225                 230                 235                 240

Leu Trp Lys Asp Trp Lys Glu Lys Asp Glu Ile Gln Met Leu Leu Ser
                245                 250                 255

Lys Ile Pro Lys Pro Lys Pro Pro Gln Arg
                260                 265

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides C-1"

(iii) HYPOTHETICAL: NO (xi) SEQUENCE DESCRIPTION: SEQ ID NO:7:

TCCAGCAGAA GGATGCAA                                                18

(2) INFORMATION FOR SEQ ID NO:8:

(i) SEQUENCE CHARACTERISTICS:
        (A) LENGTH: 18 base pairs (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides C-2"

(iii) HYPOTHETICAL: NO (xi) SEQUENCE DESCRIPTION: SEQ ID NO:8:

CTCCAGCACA CAGTCAAC                                                 18

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides C-3"

(iii) HYPOTHETICAL: NO (xi) SEQUENCE DESCRIPTION: SEQ ID NO:9:

AGGTGAACAT CTTAAATT                                                 18

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides C-4"

(iii) HYPOTHETICAL: NO (xi) SEQUENCE DESCRIPTION: SEQ ID NO:10:

TAGGAGCCAT TAATACTG                                                 18

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides C-5"

(iii) HYPOTHETICAL: NO (xi) SEQUENCE DESCRIPTION: SEQ ID NO:11:

GACCACTTTG ACTCAAGA                                                 18

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides C-6"

(iii) HYPOTHETICAL: NO (xi) SEQUENCE DESCRIPTION: SEQ ID NO:12:

CTGCAGAATC ACTATACA                                                    18

(2) INFORMATION FOR SEQ ID NO:13:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotides C-7"

(iii) HYPOTHETICAL: NO (xi) SEQUENCE DESCRIPTION: SEQ ID NO:13:

GTCCATTTCA TGAACACA                                                    18

(2) INFORMATION FOR SEQ ID NO:14:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotides C-8"

(iii) HYPOTHETICAL: NO (xi) SEQUENCE DESCRIPTION: SEQ ID NO:14:

AGCCATCTCT TTCCTCTC                                                    18

(2) INFORMATION FOR SEQ ID NO:15:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotides C-9"

(iii) HYPOTHETICAL: NO (xi) SEQUENCE DESCRIPTION: SEQ ID NO:15:

CAAGCTAGAG CTATCATG                                                    18

(2) INFORMATION FOR SEQ ID NO:16:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotides C-10"

(iii) HYPOTHETICAL: NO (xi) SEQUENCE DESCRIPTION: SEQ ID NO:16:

CGCTCCTTCA GTAGATCTTG                                                  20

(2) INFORMATION FOR SEQ ID NO:17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides C-11"

(iii) HYPOTHETICAL: NO (xi) SEQUENCE DESCRIPTION: SEQ ID NO:17:

TTGAAATTTC TGTCTGAA                                18

(2) INFORMATION FOR SEQ ID NO:18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides C-12"

(iii) HYPOTHETICAL: NO (xi) SEQUENCE DESCRIPTION: SEQ ID NO:18:

AAACTCCTTC GGGAAGGC                                18

(2) INFORMATION FOR SEQ ID NO:19:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides C-13"

(iii) HYPOTHETICAL: NO (xi) SEQUENCE DESCRIPTION: SEQ ID NO:19:

ATCAACAGAT AGCTCAGC                                18

(2) INFORMATION FOR SEQ ID NO:20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides C-14"

(iii) HYPOTHETICAL: NO (xi) SEQUENCE DESCRIPTION: SEQ ID NO:20:

GTCTTCTTGG CCCATATC                                18

(2) INFORMATION FOR SEQ ID NO:21:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
            (A) DESCRIPTION: /desc = "Oligonucleotides C-15"

(iii) HYPOTHETICAL: NO (xi) SEQUENCE DESCRIPTION: SEQ ID NO:21:

GTAGACTGTA GCAGTGGC                                                          18

(2) INFORMATION FOR SEQ ID NO:22:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotides C-16"

(iii) HYPOTHETICAL: NO (xi) SEQUENCE DESCRIPTION: SEQ ID NO:22:

GCATCCAAAG TAGAGGAG                                                          18

(2) INFORMATION FOR SEQ ID NO:23:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotides C-17"

(iii) HYPOTHETICAL: NO (xi) SEQUENCE DESCRIPTION: SEQ ID NO:23:

CCTTTGCTCC AATATGTG                                                          18

(2) INFORMATION FOR SEQ ID NO:24:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotides C-18"

(iii) HYPOTHETICAL: NO (xi) SEQUENCE DESCRIPTION: SEQ ID NO:24:

TAGAGAATAT TCGCTTGAG                                                         19

(2) INFORMATION FOR SEQ ID NO:25:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotides C-19"

(iii) HYPOTHETICAL: NO (xi) SEQUENCE DESCRIPTION: SEQ ID NO:25:

```
TAGTGCGAGC TCTGCCAGA                                                    19

(2) INFORMATION FOR SEQ ID NO:26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides C-20"

(iii) HYPOTHETICAL: NO (xi) SEQUENCE DESCRIPTION: SEQ ID NO:26:

GAGATAGAAT TCACATTC                                                     18

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides C-21"

(iii) HYPOTHETICAL: NO (xi) SEQUENCE DESCRIPTION: SEQ ID NO:27:

CTAAAAAGTA TAGATCCAGT                                                   20

(2) INFORMATION FOR SEQ ID NO:28:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides C-22"

(iii) HYPOTHETICAL: NO (xi) SEQUENCE DESCRIPTION: SEQ ID NO:28:

TAGTGCGAGC TCTGCCAGAA GTTCC                                             25

(2) INFORMATION FOR SEQ ID NO:29:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides C-23"

(iii) HYPOTHETICAL: NO (xi) SEQUENCE DESCRIPTION: SEQ ID NO:29:

AACTTCTGGC AGAGCTCGCA C                                                 21

(2) INFORMATION FOR SEQ ID NO:30:

(i) SEQUENCE CHARACTERISTICS:
```

(A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides C-24"

(iii) HYPOTHETICAL: NO (xi) SEQUENCE DESCRIPTION: SEQ ID NO:30:

CAATGGATTT TGGATAAAC                                                19

(2) INFORMATION FOR SEQ ID NO:31:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides C-25"

(iii) HYPOTHETICAL: NO (xi) SEQUENCE DESCRIPTION: SEQ ID NO:31:

CTCTACTTTG GATGCCAA                                                 18

(2) INFORMATION FOR SEQ ID NO:32:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides C-26"

(iii) HYPOTHETICAL: NO (xi) SEQUENCE DESCRIPTION: SEQ ID NO:32:

GAGTTTGGTG TTGTTTCA                                                 18

(2) INFORMATION FOR SEQ ID NO:33:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides C-27"

(iii) HYPOTHETICAL: NO (xi) SEQUENCE DESCRIPTION: SEQ ID NO:33:

GCTCTATGCA GGTGGATT                                                 18

(2) INFORMATION FOR SEQ ID NO:34:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides C-28"

(iii) HYPOTHETICAL: NO (xi) SEQUENCE DESCRIPTION: SEQ ID NO:34:

GAAACTACAG GTGCTGAG                                                18

(2) INFORMATION FOR SEQ ID NO:35:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides C-29"

(iii) HYPOTHETICAL: NO (xi) SEQUENCE DESCRIPTION: SEQ ID NO:35:

AGCTATCATG AAAGGAGG                                                18

(2) INFORMATION FOR SEQ ID NO:36:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides C-30"

(iii) HYPOTHETICAL: NO (xi) SEQUENCE DESCRIPTION: SEQ ID NO:36:

AGGATAGTGA ATGACACA                                                18

(2) INFORMATION FOR SEQ ID NO:37:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides C-31"

(iii) HYPOTHETICAL: NO (xi) SEQUENCE DESCRIPTION: SEQ ID NO:37:

ATAATCAGGG TTATTCTG                                                18

(2) INFORMATION FOR SEQ ID NO:38:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides C-41-1"

(iii) HYPOTHETICAL: NO (xi) SEQUENCE DESCRIPTION: SEQ ID NO:38:

GCACCTTATT GAAGCTCT                                                18

(2) INFORMATION FOR SEQ ID NO:39:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides C-41-2"

(iii) HYPOTHETICAL: NO (xi) SEQUENCE DESCRIPTION: SEQ ID NO:39:

GTTTGCCAAC AACCTACA                                            18

(2) INFORMATION FOR SEQ ID NO:40:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides C-41-3"

(iii) HYPOTHETICAL: NO (xi) SEQUENCE DESCRIPTION: SEQ ID NO:40:

GATAAAACCA GCGCACCT                                            18

(2) INFORMATION FOR SEQ ID NO:41:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides C-41-4"

(iii) HYPOTHETICAL: NO (xi) SEQUENCE DESCRIPTION: SEQ ID NO:41:

CTGAAGATTA GTTTGCCA                                            18

(2) INFORMATION FOR SEQ ID NO:42:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides CPP-1"

(iii) HYPOTHETICAL: NO (xi) SEQUENCE DESCRIPTION: SEQ ID NO:42:

AGCGCACCTT ATTGAAGCTC TT                                      22

(2) INFORMATION FOR SEQ ID NO:43:

(i) SEQUENCE CHARACTERISTICS:
        (A) LENGTH: 22 base pairs
        (B) TYPE: nucleic acid
        (C) STRANDEDNESS: single (D) TOPOLOGY: linear (ii) MOLECULE TYPE: other nucleic acid
            (A) DESCRIPTION: /desc = "Oligonucleotides CPP-2"

(iii) HYPOTHETICAL: NO (xi) SEQUENCE DESCRIPTION: SEQ ID NO:43:

AGGCAAGCTA GAGCTATCAT GA                                              22

(2) INFORMATION FOR SEQ ID NO:44:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotides CPP-3"

(iii) HYPOTHETICAL: NO (xi) SEQUENCE DESCRIPTION: SEQ ID NO:44:

AGATCTACTG AAGGAGCGCC AA                                              22

(2) INFORMATION FOR SEQ ID NO:45:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotides CPP-4"

(iii) HYPOTHETICAL: NO (xi) SEQUENCE DESCRIPTION: SEQ ID NO:45:

AGATTAGTTT GCCAACAACC TACA                                            24

(2) INFORMATION FOR SEQ ID NO:46:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotides PRIMER 1"

(iii) HYPOTHETICAL: NO (xi) SEQUENCE DESCRIPTION: SEQ ID NO:46:

GACTTGCTGG CTGCCTCATA                                                 20

(2) INFORMATION FOR SEQ ID NO:47:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotides PRIMER 2"

(iii) HYPOTHETICAL: NO (xi) SEQUENCE DESCRIPTION: SEQ ID NO:47:

ATATATGAAA GGTATTACAG CCACAA    26

(2) INFORMATION FOR SEQ ID NO:48:

(i) SEQUENCE CHARACTERISTICS:
        (A) LENGTH: 1508 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vi) ORIGINAL SOURCE:
        (A) ORGANISM: Homo sapiens (xi) SEQUENCE DESCRIPTION: SEQ ID NO:48:

```
GAGCGCGGTT ACCGGACGGG CTGGGTCTAT GGTCGCTCCG CGGCCGCTCC GCCGCGTGGT    60
GCTTTTTTAT CAGGGCAAGC TGTGTTCCAT GGCAGGGAAC TTTTGGCAGA GCTCCCACTA   120
TTTGCAATGG ATTTTGGATA AACAAGATCT GTTGAAGGAG CGCCAAAAGG ATTTAAAGTT   180
TCTCTCAGAG GAAGAATATT GGAAGTTACA AATATTTTTT ACAAATGTTA TCCAAGCATT   240
AGGTGAACAT CTTAAATTAA GACAACAAGT TATTGCCACT GCTACGGTAT ATTTCAAGAG   300
ATTCTATGCC AGGTATTCTC TGAAAAGTAT AGATCCTGTA TTAATGGCTC CTACATGTGT   360
GTTTTTGGCA TCCAAAGTAG AGGAATTTGG AGTAGTTTCA AATACAAGAT TGATTGCTGC   420
TGCTACTTCT GTATTAAAAA CTAGATTTTC ATATGCCTTT CCAAAGGAAT TTCCTTATAG   480
GATGAATCAT ATATTAGAAT GTGAATTCTA TCTGTTAGAA CTAATGGATT GTTGCTTGAT   540
AGTGTATCAT CCTTATAGAC CTTTGCTCCA GTATGTGCAG GACATGGGCC AAGAAGACAT   600
GTTGCTTCCC CTTGCATGGA GGATAGTGAA TGATACCTAC AGAACGGATC TTTGCCTACT   660
GTATCCTCCT TTCATGATAG CTTTAGCTTG CCTACATGTA GCCTGTGTTG TACAGCAGAA   720
AGATGCCAGG CAATGGTTTG CTGAGCTTTC TGTGGATATG GAAAAGATTT GGAAATAAT   780
CAGGGTTATT TTAAAACTAT ATGAGCAGTG GAAGAATTTC GATGAGAGAA AAGAGATGGC   840
AACCATTCTT AGTAAGATGC CAAAACCAAA ACCACCTCCA AACAGTGAAG GAGAGCAGGG   900
TCCAAATGGA AGTCAGAACT CTAGCTACAG CCAATCTTAA AACATTCCGA AGAATTCCAT   960
AGTGGACCAC TTGGAAATAA ACCATTGGAC AGATTTCAGT AATGTCTTCA GTGGAACACA  1020
AATGAAAATG AATAGCTTGT TTCTGTCAAG CATATTGGAA AGTGATTTTA TTTTTGCAAA  1080
TAGTTTTTCT TTAATATGAT TCTAGTACAT AATTGATTGA TTAAATCTCT TGATTATAAA  1140
TGTTTGGAAA GGTTCTAAGG GGACCTACAG ACAGACATAC ATAGACATTT CAAAATTAAT  1200
AGCTTTTGAT TAGTATAATA TTTCTTAATT TGGATAATAA AAATTGTAGC TTTTTATTAA  1260
GCCAGGAAAC ATGAAGCATA ATTTGTTTAA AATTCTCTTT GGTCATTGAG GGACCAAAAA  1320
AGGACGTAAA ATTTACAGTC AATCTATGAG GGTTTTTTTC CCTCCATAAG TTTAACTTTA  1380
AAACTGTATT TAAGGAATCA AATCTTACAA AATCCTGGAA GATTTTGGTA ATGATGTTGA  1440
TAATTTCAGG GAAATTAATC AAGTACCGTA TATTGATTTA AAAGTGTATT TTATTCAGTA  1500
GTTTGAGG                                                          1508
```

(2) INFORMATION FOR SEQ ID NO:49:

(i) SEQUENCE CHARACTERISTICS:
        (A) LENGTH: 1006 base pairs (B) TYPE: nucleic acid
        (C) STRANDEDNESS: double
        (D) TOPOLOGY: linear (ii) MOLECULE TYPE: cDNA (iii) HYPOTHETICAL: NO (vi) ORIGINAL SOURCE:
        (A) ORGANISM: Homo sapiens (xi) SEQUENCE DESCRIPTION: SEQ ID NO:49:

```
GAGCGCGGTT ACCGGACGGG CTGGGTCTAT GGTCGCTCCG CGGCCGCTCC GCCGCGTGGT      60
GCTTTTTTAT CAGGGCAAGC TGTGTTCCAT GGCAGGGAAC TTTTGGCAGA GCTCCCACTA     120
TTTGCAATGG ATTTTGGATA AACAAGATCT GTTGAAGGAG CGCCAAAAGG ATTTAAAGTT     180
TCTCTCAGAG GAAGAATATT GGAAGTTACA AATATTTTTT ACAAATGTTA TCCAAGCATT     240
AGGTGAACAT CTTAAATTAA GACAACAAGT TATTGCCACT GCTACGGTAT ATTTCAAGAG     300
ATTCTATGCC AGGTATTCTC TGAAAAGTAT AGATCCTGTA TTAATGGCTC CTACATGTGT     360
GTTTTTGGCA TCCAAAGTAG AGGAATTTGG AGTAGTTTCA AATACAAGAT TGATTGCTGC     420
TGCTACTTCT GTATTAAAAA CTAGATTTTC ATATGCCTTT CCAAAGGAAT TCCTTATAG     480
GATGAATCAT ATATTAGAAT GTGAATTCTA TCTGTTAGAA CTAATGGATT GTTGCTTGAT     540
AGTGTATCAT CCTTATAGAC CTTTGCTCCA GTATGTGCAG ACATGGGCC AAGAAGACAT     600
GTTGCTTCCC CTTGCATGGA GGATAGTGAA TGATACCTAC AGAACGGATC TTTGCCTACT     660
GTATCCTCCT TTCATGATAG CTTTAGCTTG CCTACATGTA GCCTGTGTTG TACAGCAGAA     720
AGATGCCAGG CAATGGTTTG CTGAGCTTTC TGTGGATATG GAAAAGATTT TGGAAATAAT     780
CAGGGTTATT TTAAAACTAT ATGAGCAGTG GAAGAATTTC GATGAGAGAA AAGAGATGGC     840
AACCATTCTT AGTAAGATGC CAAAACCAAA ACCACCTCCA AACAGAAATT CCCTGAGTGA     900
TAAGGCAATA ATCTATTGCA AAGTTACTGT GAAGGAGAGC AGGGTCCAAA TGGAAGTCAG     960
AACTCTAGCT ACAGCCAATC TTAAAACATT CCGAAGAATT CCATAG                    1006
```

(2) INFORMATION FOR SEQ ID NO:50:

(i) SEQUENCE CHARACTERISTICS:
        (A) LENGTH: 325 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Homo sapiens (xi) SEQUENCE DESCRIPTION: SEQ ID NO:50:

```
Met Val Ala Pro Arg Pro Leu Arg Arg Val Val Leu Phe Tyr Gln Gly
1               5                   10                  15

Lys Leu Cys Ser Met Ala Gly Asn Phe Trp Gln Ser Ser His Tyr Leu
            20                  25                  30

Gln Trp Ile Leu Asp Lys Gln Asp Leu Leu Lys Glu Arg Gln Lys Asp
        35                  40                  45

Leu Lys Phe Leu Ser Glu Glu Tyr Trp Lys Leu Gln Ile Phe Phe
    50                  55                  60

Thr Asn Val Ile Gln Ala Leu Gly Glu His Leu Lys Leu Arg Gln Gln
65                  70                  75                  80
```

```
Val Ile Ala Thr Ala Thr Val Tyr Phe Lys Arg Phe Tyr Ala Arg Tyr
                85                  90                  95

Ser Leu Lys Ser Ile Asp Pro Val Leu Met Ala Pro Thr Cys Val Phe
            100                 105                 110

Leu Ala Ser Lys Val Glu Glu Phe Gly Val Val Ser Asn Thr Arg Leu
        115                 120                 125

Ile Ala Ala Thr Ser Val Leu Lys Thr Arg Phe Ser Tyr Ala Phe
    130                 135                 140

Pro Lys Glu Phe Pro Tyr Arg Met Asn His Ile Leu Glu Cys Glu Phe
145                 150                 155                 160

Tyr Leu Leu Glu Leu Met Asp Cys Cys Leu Ile Val Tyr His Pro Tyr
                165                 170                 175

Arg Pro Leu Leu Gln Tyr Val Gln Asp Met Gly Gln Glu Asp Met Leu
            180                 185                 190

Leu Pro Leu Ala Trp Arg Ile Val Asn Asp Thr Tyr Arg Thr Asp Leu
        195                 200                 205

Cys Leu Leu Tyr Pro Pro Phe Met Ile Ala Leu Ala Cys Leu His Val
    210                 215                 220

Ala Cys Val Val Gln Gln Lys Asp Ala Arg Gln Trp Phe Ala Glu Leu
225                 230                 235                 240

Ser Val Asp Met Glu Lys Ile Leu Glu Ile Ile Arg Val Ile Leu Lys
                245                 250                 255

Leu Tyr Glu Gln Trp Lys Asn Phe Asp Glu Arg Lys Glu Met Ala Thr
            260                 265                 270

Ile Leu Ser Lys Met Pro Lys Pro Lys Pro Pro Asn Arg Asn Ser
    275                 280                 285

Leu Ser Asp Lys Ala Ile Ile Tyr Cys Lys Val Thr Val Lys Glu Ser
290                 295                 300

Arg Val Gln Met Glu Val Arg Thr Leu Ala Thr Ala Asn Leu Lys Thr
305                 310                 315                 320

Phe Arg Arg Ile Pro
            325

(2) INFORMATION FOR SEQ ID NO:51:

(i) SEQUENCE CHARACTERISTICS:
        (A) LENGTH: 854 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vi) ORIGINAL SOURCE:
        (A) ORGANISM: Homo sapiens (xi) SEQUENCE DESCRIPTION: SEQ ID NO:51:

GAGCGCGGTT ACCGGACGGG CTGGGTCTAT GGTCGCTCCG CGGCCGCTCC GCCGCGTGGT      60

GCTTTTTTAT CAGGGCAAGC TGTGTTCCAT GGCAGGGAAC TTTTGGCAGA GCTCCCACTA    120

TTTGCAATGG ATTTTGGATA ACAAGATCT GTTGAAGGAG CGCCAAAAGG ATTTAAAGTT     180

TCTCTCAGAG GAAGAATATT GGAAGTTACA AATATTTTTT ACAAATGTTA TCCAAGCATT    240

AGGTGAACAT CTTAAATTAA GACAACAAGT TATTGCCACT GCTACGGTAT ATTTCAAGAG    300

ATTCTATGCC AGGTATTCTC TGAAAAGTAT AGATCCTGTA TTAATGGCTC CTACATGTGT    360
```

```
GTTTTTGGCA TCCAAAGTAG AGGAATTTGG AGTAGTTTCA AATACAAGAT TGATTGCTGC      420

TGCTACTTCT GTATTAAAAA CTAGATTTTC ATATGCCTTT CCAAAGGAAT TCCTTATAG      480

GATGAATCAT ATATTAGAAT GTGAATTCTA TCTGTTAGAA CTAATGGTAA GTAAATCTTC      540

TGTGATTAAT AGATTAAAAC ATTTTTAAAT TAAATGAAGT TGGAAATTAT TTAAAGAAAT      600

GATTTTAGAG AGGTACATTT TAAACCATC CACCTAATAT GTGATGGTGA AATCATGGTA       660

GCCTATTTAT ATTAGCACCT AGAGTCTCTC TGAAGCCTGT AAAATAATTT GTATATCCTA      720

CTTAGGATGG GAAAATTTTT CTGTTCTATA GTAAGTAACT ATAATGAAAG GATTACAAAC      780

AGACAAGTCA GGACATTAAA CCACCATAAA TTATGTGCAC AATTTGTGTG TGCGTGCAGT      840

GTTATTTAAA GATA                                                       854
```

(2) INFORMATION FOR SEQ ID NO:52:

(i) SEQUENCE CHARACTERISTICS:
        (A) LENGTH: 179 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Homo sapiens (xi) SEQUENCE DESCRIPTION: SEQ ID NO:52:

```
Met Val Ala Pro Arg Pro Leu Arg Arg Val Val Leu Phe Tyr Gln Gly
1               5                   10                  15

Lys Leu Cys Ser Met Ala Gly Asn Phe Trp Gln Ser Ser His Tyr Leu
            20                  25                  30

Gln Trp Ile Leu Asp Lys Gln Asp Leu Leu Lys Glu Arg Gln Lys Asp
        35                  40                  45

Leu Lys Phe Leu Ser Glu Glu Tyr Trp Lys Leu Gln Ile Phe Phe
    50                  55                  60

Thr Asn Val Ile Gln Ala Leu Gly Glu His Leu Lys Leu Arg Gln Gln
65                  70                  75                  80

Val Ile Ala Thr Ala Thr Val Tyr Phe Lys Arg Phe Tyr Ala Arg Tyr
                85                  90                  95

Ser Leu Lys Ser Ile Asp Pro Val Leu Met Ala Pro Thr Cys Val Phe
            100                 105                 110

Leu Ala Ser Lys Val Glu Glu Phe Gly Val Val Ser Asn Thr Arg Leu
        115                 120                 125

Ile Ala Ala Ala Thr Ser Val Leu Lys Thr Arg Phe Ser Tyr Ala Phe
    130                 135                 140

Pro Lys Glu Phe Pro Tyr Arg Met Asn His Ile Leu Glu Cys Glu Phe
145                 150                 155                 160

Tyr Leu Leu Glu Leu Met Val Ser Lys Ser Ser Val Ile Asn Arg Leu
                165                 170                 175

Lys His Phe
```

(2) INFORMATION FOR SEQ ID NO:53:

(i) SEQUENCE CHARACTERISTICS:
        (A) LENGTH: 815 base pairs
        (B) TYPE: nucleic acid
        (C) STRANDEDNESS: double
        (D) TOPOLOGY: linear -continued

```
    (ii) MOLECULE TYPE: cDNA (iii) HYPOTHETICAL: NO (vi) ORIGINAL SOURCE:
           (A) ORGANISM: Homo sapiens (xi) SEQUENCE DESCRIPTION: SEQ ID NO:53:

AAACCATTCT AATATTCTGT TCCATAAATA TACCTATTAA AATTAATTTT ATAACAAAAC       60

ACAGACTGTA AACATAAAAA TTAAGGACAA GTTNTCTTTA AAGTAATCAG GATACTTTTT      120

GGTAGTCTGC AAACATACAT ATAAATTTAC TGTATAATTT CTGGTTTTTT AATTTGATTT      180

TTCTGATTTT TAAAAAATTA GAAAAATGTG TTTATAATTT GTTATGAGAT TTTGAAATTT      240

AAAATATATT TAGCTGTAAT TTTATTCATT GATATGTGCT TATTTGTTGT CACATTCATG      300

TATCCATCCT TTTGCCTTGA TGTTTTCACT TTTATAGCTG TGCTTCAGTA GTATAAAAGG      360

AAATAAATGT GTGCAAAGAT GGGAAATCTG GCCCTCTCTG GAGGAAATAT ACAATCAGAT      420

GAGGTAGTTC TGCTTTCAGT AATAATATGA TTTACATTTC TATAGGAGGA TAGTGAATGA      480

TACCTACAGA ACGGATCTTT GCCTACTGTA TCCTCCTTTC ATGATAGCTT TAGCTTGCCT      540

ACATGTAGCC TGTGTTGTAC AGCAGAAAGA TGCCAGGCAA TGGTTTGCTG AGCTTTCTGT      600

GGATATGGAA AAGATTTTGG AAATAATCAG GGTTATTTTA AAACTATATG AGCAGTGGAA      660

GAATTTCGAT GAGAGAAAAG AGATGGCAAC CATTCTTAGT AAGATGCCAA AACCAAAACC      720

ACCTCCAAAC AGTCAAGGAG AGCAGGGTCC AAATAAGGCA ATAATCTATT GCAAAGTTAC      780

TTGGAAGTCA GAACTCTAGC TACAGCCAAT CTTAA                                815
```

CYCLIN-C VARIANTS, AND DIAGNOSTIC AND THERAPEUTIC USES THEREOF

CROSS-REFERENCE TO RELATED APPLICATIONS

The present Application is a non-provisional application claiming the priority of copending provisional U.S. Ser. No. 60/018,614 filed on Jun. 3, 1996. Applicants claim the benefits of this Application under 35 U.S.C. §119(e).

RESEARCH SUPPORT

The research leading to the present invention was supported in part by NIH grants CA 67938 and CA 21765. The government may have certain rights in the present invention. Support for this invention was also provided by the AMERICAN LEBANESE SYRIAN ASSOCIATED CHARITIES.

FIELD OF THE INVENTION

This invention relates generally to naturally occurring alternative forms of a protein that interacts with a protein kinase. This interaction has been proposed to be involved in the regulation of RNA transcription. The invention more particularly relates to a truncated form of the protein, a more stable form of the protein, related biomolecules and to methods of making and using the same, including diagnostic and therapeutic uses. The invention further includes corresponding amino acid and nucleotide sequences.

BACKGROUND OF THE INVENTION

The cell cycle for replicating cells can be divided into two periods: (1) the cell division period, when the cell divides and separates, with each daughter cell receiving identical copies of the DNA; and (2) the period of growth, known as the interphase period. For the cell cycle of eucaryotes, the cell division period is termed the M (mitotic) period. The interphase period in eucaryotes is further divided into three successive phases: G1 (gap 1) phase, which directly follows the M period; S (synthetic) phase, which follows G1; and G2 (gap 2) phase, which follows the S phase, and immediately precedes the M period. During the two gap phases no net change in DNA occurs, though damaged DNA may be repaired. On the other hand, throughout the interphase period there is continued cellular growth and continued synthesis of other cellular components. Towards the end of the G1 phase, the cell passes a restrictive point and becomes committed to duplicate its DNA. At this point, the cell is also committed to divide. During the S phase, the cell replicates DNA. The net result is that during the G2 phase, the cell contains two copies of all of the DNA present in the G1 phase. During the subsequent M period, the cells divide with each daughter cell receiving identical copies of the DNA. Each daughter cell starts the next round of the growth cycle by entering the G1 phase.

The G1 phase represents the interval in which cells respond maximally to extracellular signals, including mitogens, anti-proliferative factors, matrix adhesive substances, and intercellular contacts. Passage through the restrictive point late in G1 phase defines the time at which cells lose their dependency on mitogenic growth factors for their subsequent passage through the cycle and, conversely, become insensitive to anti-proliferative signals induced by compounds such as transforming growth factor, cyclic AMP analogs, and rapamycin. Once past the restrictive point, cells become committed to duplicating their DNA and undergoing mitosis, as noted above, and the programs governing these processes are largely cell autonomous. (See generally, Darnell et al. (1986) in *Molecular Cell Biology*, pp. 146–148, Scientific American Books, New York.)

Regulation of the human cell cycle requires the periodic formation, activation, and inactivation of protein kinase complexes that consist of a regulatory (cyclin) subunit and a catalytic (cyclin dependent kinase or cdk) subunit. Cell cycle-dependent fluctuations in the levels of many of the cyclin proteins contribute to the activation of these protein kinase complexes. For example, cyclin B participates in the regulation of the G2/M transition by its association with its catalytic subunit, $p34^{cdc2}$, whereas cyclin A, in complexes with both $p34^{cdc2}$ and cdk2, is essential for the completion of S-phase and entry into G2-phase. Complexes formed between the D-type cyclins and either cdk4 or cdk6 integrate growth factor signals and the cell cycle, allow cells to progress through G1-phase. This particular cell cycle pathway is specifically altered during tumorigenesis, presumably due to its role in responses to mitogenic stimulation. Alterations have been identified in many components of this pathway, including the D-type cyclins, cyclin dependent protein kinases, and cyclin dependent kinase inhibitors (CKIs). Another G1-phase cyclin, cyclin E, in conjunction with its catalytic subunit cdk2, appears to be essential for progression from G1-phase into S-phase and the initiation of DNA replication. Cyclin E and cdk2 do not appear to be directly targeted during tumorigenesis, quite possibly due to their essential nature. (See generally, Sherr, *Cell* 79:551–555 (1994)) and Sherr, *Cell* 73:1059–1065 (1993)).

A class of novel polypeptides that are collectively known as cdk inhibitors (CKIs) can negatively regulate cyclin/cdk activity by associating with these complexes. These so-called "cell cycle brakes" act to inhibit cyclin/cdk complexes by binding specifically to either the cyclin or the cdk, but generally not both. CKI activity is cell cycle regulated allowing these proteins to function as inhibitors of their cognate cyclin/cdk complexes for very limited periods during the cell cycle. The cdk inhibitors isolated thus far include $p21^{Cip1,Waf1,Sdi1,Cap20}$, $p27^{Kip1}$, $p57^{Kip2}$, and a small family of inhibitors of cdk4 (INK4), which include $p16^{INK4a}$, $p15^{INK4b}$, $p18^{INK4c}$, and $p19^{INK4d}$. In some cases (i.e., $p21^{Cip1,Waf1,Sdi1,Cap20}$) this inhibitory activity may be conditional, and these proteins may also act to positively regulate cyclin/cdk complexes by functioning as "bridge" molecules that maintain complex formation and enzyme activity. The p21, p27, and p57 proteins have been found in association with multiple cyclins (including D, E, and A), while the INK4 inhibitors specifically interact with complexes containing the D-type cyclins and cdk4 or cdk6. Because these proteins are important in cell cycle control, many are targeted for inactivation by both tumor viruses and genetic alterations during oncogenesis. Loss of specific CKI function can result in unregulated DNA replication, and aid in the generation of further mutations due to accumulating DNA damage. To date, mutations and/or deletions of the $p16^{INK4a}$ gene have been observed in a broad range of tumor types, strongly supporting its role as a tumor suppressor. (See generally, Sherr et al., *Genes & Devel.* 9:1149–1163 (1995)) and Morgan, *Nature* 374:131–134 (1995).)

Cyclin C was originally isolated from both human and Drosophila cDNA libraries by virtue of its ability to complement a CLN 1-3 defective *S. cerevisiae* strain (Lew et al., *Cell* 66:1197–1206 (1991); Leopold et al., *Cell* 66:1207–1216 (1991); Lahue et al., (1991)). The CLN1-3 yeast cyclins function during the G1-phase of the cell cycle by helping convey external growth signals to the nucleus and promote cell cycle progression (Cross, *Mol. Cell Biol.*

10:6482–6490 (1990). Thus, it was postulated that cyclin C was, itself, a G1-phase cyclin regulatory partner. The recent discovery of a cdk partner for cyclin C, cdk8, indicates that, like other G1-phase cyclins, cyclin C functions to regulate a specific cdk, in a cell cycle dependent manner (Tassan et al., *Proc. Natl. Acad. Sci., USA* 92: 8871–8875 (1995)). Cyclin C not only associates with cdk8 in vitro, thereby activating the kinase, but also associates with cdk8 in vivo. Furthermore, the high degree of sequence identity between mammalian cyclin C and cdk8 with the *S. cerevisiae* SRB10 and SRB11 gene products, indicate that this complex plays an important role in the regulation of transcription (O'Neill et al., *Nature*, 374:121–122 (1995); Liao et al., *Nature* 374:193–196 (1995)). In yeast, the SRB10 and SRB11 gene products, a cdk and a regulatory cyclin partner respectively, are associated in vivo with RNA polymerase II. This cyclin/cdk complex is involved in both positive and negative regulation of transcription. The complex also may play a particularly important role in relaying extracellular growth signals to the transcription apparatus by either directly, or indirectly, phosphorylating the C-terminal domain (CTD) of RNA polymerase II (Tassan et al., supra).

The human cdk 8 catalytic partner of cyclin C maps to human chromosome 13q12, a region associated with the BRCA2 breast cancer susceptibility gene, but the significance of this observation is unknown. The CCNC gene encoding human cyclin C has recently been cloned and localized to human chromosome 6q21 (Demetrick et al., *Cytogenet. Cell Genet.* 69:190–192 (1995); Li et al. (1996a)). This region of chromosome six is often deleted or altered during tumorigenesis, suggesting that the CCNC gene might be a candidate tumor suppressor (Kowalczyk et al., (1985); Prigogina et al. (1988)). The integrity of the CCNC gene was examined in a subset of acute lymphoblastic leukemias (ALLs) with 6q21 deletions, and one allele of this gene was consistently deleted (>90% of primary tumors) (Li et al., (1996a)). However, careful examination of the remaining CCNC allele by single-strand conformational polymorphism (SSCP) revealed no further physical alterations. Similar results involving the frequent deletion of cyclin dependent protein kinase inhibitors, such as p27$^{Kip1}$, have been demonstrated by others. It is possible that these genes exert their effects in tumors due to haploinsufficiency of the corresponding proteins, or that they are not the actual tumor suppressors, but share close physical linkage with the target genes (Pietenpol et al., *Cancer Res.* 55:1206–1210 (1995); Li et al. (1996)).

The existence of a specific and unique cyclin dependent protein kinase partner, cdk8, for cyclin C indicates that cyclin C functions like other cyclins, i.e., to regulate a kinase catalytic domain. It has been proposed that the cyclin C-cdk8 complex regulates RNA transcription during the cell cycle. However, to date, no factor analogous to a cdk inhibitor has been identified that, in turn, specifically regulates cyclin C/cdk8 complex activity.

The citation of any reference herein should not be deemed as an admission that such reference is available as prior art to the instant invention.

SUMMARY OF THE INVENTION

One aspect of the present invention describes a novel amino acid polymer that specifically regulates cyclin C/cdk8 complex activity and thereby plays an important role in the regulation of RNA transcription. The amino acid polymer functions in a manner that is analogous, at least in result, to other cdk inhibitors, by disabling the active cyclin C/cdk8 complex during a portion of the cell cycle. Much like the p16$^{INK4}$-related proteins and other CKIs such as p21$^{Waf1/Cip1}$, p27$^{Kip1}$, and p57$^{Kip2}$, the amino acid polymer functions as inhibitor of its associated protein kinase at specific times during the cell cycle.

The present invention includes an amino acid polymer that hinders the formation of an active cyclin C-cdk8 complex. In some embodiments, the amino acid polymer also possesses a specific binding affinity for cdk8. In one aspect of the invention the amino acid polymer is a protein. In another aspect of the invention the amino acid polymer is an active fragment of the protein. The present invention includes agonists, and mimics of the amino acid polymer.

In some embodiments of this aspect of the present invention, the amino acid polymer is a truncated form of cyclin C. In one embodiment the amino acid polymer is a truncated form of cyclin C that comprises at least about 20% or alternatively at least about 30% of the amino acid sequence encoded by the cyclin-box region. In another embodiment the amino acid polymer is a truncated form of cyclin C that comprises at least about 40% or alternatively at least about 50% of the amino acid sequence encoded by the cyclin-box region. In a preferred embodiment the amino acid polymer is a truncated form of cyclin C that comprises at least about 60% or alternatively at least about 70% of the amino acid sequence encoded by the cyclin-box region. In the another preferred embodiment of this aspect of the invention, the amino acid polymer has the amino acid sequence of SEQ ID NO:4 (see, FIG. 1B).

In one embodiment of the invention the amino acid polymer is derived from Avian cells. In a preferred embodiment the amino acid polymer is derived from mammalian cells. In one such embodiment, the amino acid polymer is a human protein that has all of the intronic sequences removed with the exception of the introns located between exon 7 and 9 (exon 8 is included). In a particular embodiment of this type, the human amino acid polymer has an amino acid sequence of SEQ ID NO:52.

Another aspect of the present invention, includes an isolated amino acid polymer corresponding to a human cyclin C that does not encode a PEST sequence rich carboxyterminal domain. In one such embodiment, the amino acid polymer contains additional coding sequence between sequences derived from exons 11 and 12 in the human cyclin C cDNA. In a particular embodiment, the amino acid polymer has an amino acid sequence of SEQ ID NO:50. Such an amino acid polymer can have greater stability than the native human cyclin C since the PEST sequence has been shown to be involved in the rapid turnover of many proteins.

A further aspect of the invention includes the use of detectable labels, such as but not limited to an enzyme, a radioactive element, a biochemiluminescent, a chromophore that absorbs in the ultraviolet and/or visible and/or infrared region of the electromagnetic spectrum; and a fluorophore. The present invention includes the amino acid polymer labeled with such a detectable label.

The present invention includes antibodies to all of the amino acid polymers of the instant invention. In a preferred embodiment of this aspect of the invention, there are antibodies for truncated cyclin C which have a greater affinity for the truncated protein than for the full-length form of cyclin C so that the truncated cyclin C may be distinguished from the full-length form of cyclin C. In one such embodiment, the antibody is raised against a peptide comprising all or a portion of amino acids 167–178 of SEQ ID NO:52.

In another embodiment, the antibody is for an amino acid polymer of the present invention that corresponds to a human cyclin C that does not encode a PEST sequence rich carboxyterminal domain. Preferably such an antibody has a greater affinity for the amino acid polymer than for human cyclin C. In one such embodiment, the antibody is raised against a peptide comprising all or a portion of amino acids 286–325 of SEQ ID NO:50.

The antibodies of the present invention may be selected from polyclonal antibodies, monoclonal antibodies or chimeric (bispecific) antibodies and all such variants are considered to be included herein. Either type of antibody can further comprise a detectable label as described above.

A related aspect of the present invention includes an immortal cell line that produces a monoclonal antibody against the amino acid polymers of the instant invention. In one embodiment the immortal cell line produces a monoclonal antibody against a truncated cyclin C. In one such embodiment the immortal cell line produces a monoclonal antibody against the truncated cyclin C having the amino acid sequence of SEQ ID NO:4 and/or SEQ ID NO:52. Alternatively, the immortal cell line can produce a monoclonal antibody to SEQ ID NO:50.

The present invention also includes methods for isolating the amino acid polymers from bacterial, insect or animal cells.

One aspect of the present invention includes the isolated nucleic acids that encode the amino acid polymers of the present application. In some embodiments the nucleic acid is an MRNA, in other embodiments it is a recombinant DNA molecule, or a degenerate variant thereof. In one such embodiment, the isolated nucleic acid encodes the amino acid sequence of SEQ ID NO:4.

In one particular embodiment of this type, the nucleic acid has the coding sequence for the amino acid sequence of SEQ ID NO:4 contained in SEQ ID NO:2. In another embodiment, the isolated nucleic acid encodes the amino acid sequence of SEQ ID NO:52. In one particular embodiment of this type, the nucleic acid has the coding sequence for the amino acid sequence for SEQ ID NO:52 contained in SEQ ID NO:51. In yet another embodiment, the isolated nucleic acid encodes the amino acid sequence of SEQ ID NO:50. In one particular embodiment of this type, the nucleic acid has the cod ing sequence for the amino acid sequence for SEQ ID NO:50 contained in SEQ ID NO:49.

The present invention also includes the corresponding DNAs, including cDNAs and mRNAs. Nucleic acids that hybridize to the nucleic acids of the present invention under standard and/or stringent hybridization conditions are also included in the present invention.

Nucleotide probes are also included in the present invention. Such nucleotide probes may be used for screening for the nucleic acids of the present invention. All of the nucleotide probes of the present invention may be labeled with a detectable label as described above.

In one embodiment the nucleotide probe comprises all or a portion of the nucleotide sequence of nucleotides 885–928 of SEQ ID NO:49. In another embodiment, the nucleotide probe comprises all or a portion of the nucleotide sequence of nucleotides 527–771 of SEQ ID NO:51. In still another embodiment, the nucleotide probe comprises all or a portion of the nucleotide sequence of SEQ ID NO:53. In still another embodiment, the nucleotide probe comprises all or a portion of the nucleotide sequence of nucleotides 357–429 of SEQ ID NO:2.

One aspect of the present invention includes expression vectors that contain a nucleic acid of the present invention which is operatively linked to an expression control sequence. These expression vectors may be homologously recombined in a chromosome in a cell. In some embodiments of this aspect of the invention, the cell contains a nucleic acid that has been disrupted, and the cell is unable to express a functional form of the amino acid polymer of the present invention. In one such embodiment of this aspect of the invention, the cell is a chicken DT40 cell.

In other embodiments of this aspect of the invention, the cell is mammalian and can be placed into a mammalian blastocyst. The blastocyst can then be re-implanted into a pseudopregnant female mammal to generate a transgenic animal. In one embodiment of this aspect of the invention, the transgenic animal contains a nucleic acid that has been disrupted, and the transgenic animal cannot express a functional form of the amino acid polymer of the present invention. In more preferred embodiments the transgenic animal is a mouse that can be used as an animal model. When the transgenic mouse contains a disrupted nucleic acid as described above, the transgenic animal is a "knockout" mouse.

The present invention also includes a pharmaceutical composition for treating oncogenesis containing a therapeutically effective amount of an amino acid polymer of the present invention, or an agent capable of promoting the production and/or activity of the amino acid polymer, or an agent capable of mimicking the activity of the amino acid polymer, or an agent capable of inhibiting the production and/or activity of the amino acid polymer, and mixtures thereof.

An alternative aspect of the present invention includes antisense nucleic acid that functions by hybridizing to the mRNA encoding the amino acid polymers of the present invention. In some embodiments the antisense nucleic acid is RNA. In other embodiments the antisense nucleic acid is DNA. The present invention also includes a recombinant DNA molecule having a DNA sequence which, on transcription, produces an antisense ribonucleic acid against an mRNA coding for an amino acid polymer of the present invention.

In still another aspect of the present invention there is a ribozyme that catalyzes the cleaving of a precursor RNA as part of the process of converting the precursor RNA to an MRNA transcript encoding truncated cyclin C. The precursor RNA contains the exons that encode cyclin C, and one or more introns that have one or more sites for cleaving the introns from the precursor RNA. The ribozyme acts at a particular site of the precursor RNA, a site which is not cleaved during the process of converting the precursor RNA to an mRNA transcript encoding the full-length cyclin C. In one embodiment the ribozyme is a Tetrahymena-type ribozyme. In another embodiment the ribozyme is a Hammerhead-type ribozyme. The present invention also includes a recombinant DNA molecule which, upon transcription, produces the ribozyme. In preferred embodiments the site of cleavage of the RNA precursor for the ribozyme is in the cyclin-box region.

Test kits are also included in the present invention. Test kits contain markers with specific affinities for particular target molecules and directions for using the kit. More particularly, these test kits are for identifying target molecules which are the amino acid polymers and nucleic acids of the present invention. Markers may be labeled with the detectable labels of the present invention. In one embodiment, a nucleic acid of the present invention is identified in a biological sample using a kit containing a marker that is a detectably labeled nucleotide probe of the present invention. In another embodiment, an amino acid polymer of the present invention is identified in a biological sample using a kit containing a marker that is an antibody of the present invention. In a preferred embodiment of this type, the marker is an antibody that is specific for truncated cyclin C. In some embodiments, the markers are in packaged in predetermined amounts. In other embodiments a standard target molecule, known to react with the marker, is included in the kit. Other kits may contain additional reagents that react with the marker to bestow or enhance its detectability and/or buffering materials.

One preferred set of directions is for using a kit to detect the presence of an amino acid polymer of the present invention by the steps of:

(a) contacting a biological sample obtained from a cell, in which the presence of the amino acid polymer is suspected, with a marker that is an antibody for the amino acid polymer, under conditions that allow binding of the amino acid polymer to the antibody to occur; and (b) detecting whether the binding has occurred. Detection of binding indicates the presence of the amino acid polymer in the sample.

Another preferred set of directions is for using a kit of the present invention to detect the presence of an alternatively spliced mRNA of the present invention by the steps of:

(a) contacting a biological sample obtained from a cell, in which the presence of the alternatively spliced mRNA is suspected, with a marker that is a nucleotide probe for the alternatively spliced mRNA, under conditions that allow hybridization to occur;and (b) detecting whether hybridization has occurred. Detection of hybridization indicates the presence of the alternatively spliced mRNA in the sample.

These directions are not meant to be solely for kits, but rather also function as teachings for the skilled artisan to practice the methodology with the appropriate reagents, even in the absence of the kits themselves.

The invention also includes the full-length form of Avian cyclin C having the amino acid sequence of SEQ ID NO:3 (see, FIG. 1A and FIG. 1C) antibodies raised against it and nucleic acids that code for the amino acid sequence of SEQ ID NO:3. More specifically, the invention includes the nucleic acid having the DNA sequence of SEQ ID NO: 1 (see, FIG. 1A and FIG. 1C). In a related embodiment, the nucleic acid has an RNA sequence corresponding to SEQ ID NO: 1. The invention includes the use of these biomolecules to perform targeted disruption of the cyclin C gene in chicken DT40 cells via homologous recombination. Targeted disruption is a very powerful molecular genetic tool used in drug development. The chicken DT40 cell line is a valuable system for the ready isolation of mutant cells, that is technically less difficult and less time consuming than the murine model.

The present invention also includes methodology for distinguishing the G2/M phase (late G2 phase and M phase) from the G1/S phase (late G1 phase and S phase) in the cell cycle of a given cell. This methodology relies on the presence of the truncated cyclin C and one of the alternatively spliced mRNA e.g., CmRNA1, CmRNA2, or an mRNA-encoding the amino acid sequence of SEQ ID NO:52 during the G2/M phase and their absence during the G1/S phase. Monitoring either the alternatively spliced mRNA or truncated cyclin C alone or together may be used to distinguish these phases. Directions and kits described above for identifying truncated cyclin C or the alternatively spliced mRNA may be used for this purpose.

The present invention also includes a method of preventing and/or treating oncogenesis by administering to an animal a therapeutically effective amount of the truncated cyclin C, an agent capable of promoting the production and/or activity of the truncated cyclin C, an agent capable of mimicking the activity of the truncated cyclin C, an agent capable of inhibiting the production of truncated cyclin C, and mixtures thereof.

The present invention also includes a method of promoting cell growth by administering to a subject animal a nucleic acid encoding the amino acid sequence of SEQ ID NO:50 or the amino acid polymer itself. This longer lived from of a cyclin C should be more effective since less protein will be needed to be administered or synthesized.

Another aspect of the invention is an in vitro method for detecting or diagnosing the presence of a disease associated with elevated or decreased levels of the truncated cyclin C in a mammalian subject having the steps of: (a) evaluating the level of the truncated cyclin C in a biological sample from a mammalian subject and (b) comparing the level detected in step (a) to a level of the truncated cyclin C present in normal subjects or in the subject at an earlier time. An increase in the level of the truncated cyclin C as compared to normal levels indicates a disease associated with elevated levels of truncated cyclin C, and decreased level of truncated cyclin C as compared to normal levels indicates a disease associated with decreased levels of truncated cyclin C.

A variation of this aspect of the invention tests for the presence of truncated cyclin C during the different phases of the cell cycle. The presence of truncated cyclin C during the G1/S phase or its absence during the G2/M phase is indicative of a diseased state.

An in vitro method for monitoring a therapeutic treatment of a disease associated with elevated or decreased levels of truncated cyclin C in a mammalian subject is also disclosed. This test evaluates the levels of the truncated cyclin C in a series of biological samples obtained at different time points from a mammalian subject undergoing a therapeutic treatment for a disease associated with elevated or decreased levels of truncated cyclin C.

The present invention also includes methods of delivering a recombinant DNA molecule, encoding the amino acid polymers of the present invention, to a target cell which comprises providing a virus-derived vector that has been modified to comprise the recombinant DNA molecule and causing the vector to transfect the cell. Appropriate virus derived vectors include but are not limited to adenovirus, adeno-associated virus and retrovirus derived vectors. In one embodiment of this invention, the recombinant DNA is designed to be transcribed in the target cell constitutively. In another embodiment, the recombinant DNA is designed to be transcribed in the target cell under regulatable conditions. In preferred embodiments, the target cell is a human cell.

These and other aspects of the present invention will be better appreciated by reference to the following drawings and Detailed Description.

BRIEF DESCRIPTION OF THE DRAWINGS

FIGS. 1A–1C depict nucleotide sequence(s) and predicted ORFs of the avian cyclin C and alternatively spliced cyclin C cDNAs. (FIG. 1A) The avian cyclin C cDNA sequence (SEQ ID NO: 1) and its predicted ORF (SEQ ID NO:3). The cyclin-box region is shaded. The translational start site for the cyclin C protein is indicated by the bold M. The location of introns within the coding regions is shown by the arrowheads above the DNA sequence. The termination codon is indicated by an asterisk. (FIG. 1B) The alternatively spliced exon is shown by the large, bolded arrowheads. The nucleotide sequence (SEQ ID NO:2) and corresponding ORF of this alternatively spliced region is shown in bold italics. The termination codons are denoted by asterisks. The alternatively spliced region rejoins the normal cyclin C sequence after the second large, bolded arrowhead above the DNA sequence. GenBank acquisition numbers for these sequences are as follows: cyclin C (U40873), alternatively spliced cyclin C( U40874). (FIG. 1C) The predicted protein sequence of the avian cyclin C cDNA is shown in comparison to the corresponding human (line 2) and Drosophila (line 3) protein sequences. Identity is denoted by a hyphen (−) and gaps are denoted by periods (.). The conserved cyclin-box region is shown in shadowed boxes. The human cyclin C protein contains 20 additional amino acid residues at its aminoterminus, unlike the avian or Drosophila proteins which do not contain this region.

(FIG. 3A) RT-PCR primers corresponding to the 5' portion of exon 4a and the 3' portion of exon 7. (FIG. 3B) RT-PCR primers corresponding to the 3' portion of exon 4a and the 5' portion of exon 2.

FIGS. 4A–4D depict Northern blot analysis of alternatively spliced cyclin C mRNA expression in synchronized DT40 cells. RNA isolated from elutriated and nocodazole-blocked DT40 (B-cells) was transferred to a membrane and hybridized with either, (FIG. 4A) the alternatively spliced cyclin C PCR probe (described in Materials and Methods), (FIG. 4B) hybridization of the same RNA samples with the avian cyclin C probe, (FIG. 4C) a chicken cyclin B2 cDNA probe, or (FIG. 4D) the same RNAs stained with EtBr. The location of the major alternatively spliced cyclin C transcript (1.7 kb; CmRNA-2, having SEQ ID NO:2) is shown by the arrow. The location of the cyclin B2 mRNA is also appropriately indicated.

(FIG. 5A) To determine whether the Drosophila cyclin C antibody would recognize the avian proteins, it was used to immunoprecipitate either the full-length normal cyclin C transcript or the alternatively spliced cyclin C transcript, which produces a truncated cyclin C protein. These cyclin C proteins were generated by in vitro transcription translation (IVTT) and then immunoprecipitated as described by others (Leclerc et al., Molec. Biol. Cell, 7:505–513 (1996). (FIG. 5B) The same Drosophila cyclin C antibody was used to detect either (1) the in vitro transcribed translated normal (C) or alternatively spliced (AC) transcripts, (2) total cell lysate from nocodazole blocked DT40 cells, or (3) the same DT40 cell lysate after preincubation with a GST-cyclin C fusion protein corresponding to the avian gene. Incubation of the cyclin C antibody with the GST-cyclin C fusion protein acts as a competitor. Competition with this GST-cyclin C protein is indicated below the lanes with a (+). The location of the normal ~30 kDa cyclin C protein, as well as the ~19 kDa truncated cyclin C-box protein is marked on the side of the panels.

FIG. 6 shows the comparison of normal human cyclin C protein sequence and alternatively spliced form 1 (human cyclin C alternatively spliced form with an additional exon between 11 and 12). Single letter amino acid sequence of normal human cyclin C (top line) and alternatively spliced from 1 (bottom line). Identical residues are indicated by (−). Gaps in the sequence are indicated by (/).

FIG. 7 shows the nucleotide sequence comparison of human cyclin C and alternatively spliced human cyclin C form 1 (as defined in FIG. 6). The nucleotide sequence of human cyclin C is shown on the top line. Alternatively spliced form 1 on the bottom line. Identical nucleotides are indicated by (−) and gaps are shown by (/).

FIG. 8 shows the comparison of normal human cyclin C protein sequence and partially spliced form 1. Single letter amino acid sequence of normal human cyclin C (top line) and partially spliced form 1 (bottom line). Identical residues are indicated by (−). Gaps in the sequence are indicated by (/). The predicted termination codon is shown by *.

FIG. 9 shows the nucleotide sequence comparison of human cyclin C and partially spliced human cyclin C form 1. The nucleotide sequence of human cyclin C is shown on the top line. Partially spliced form 1 on the bottom line. Identical nucleotides are indicated by (−) and gaps are shown by (/) and ::: indicates the location of an approximately 600 nucleotides of unsequenced DNA presumed to contain exon 8.

DESCRIPTION OF THE INVENTION

Figure 2:
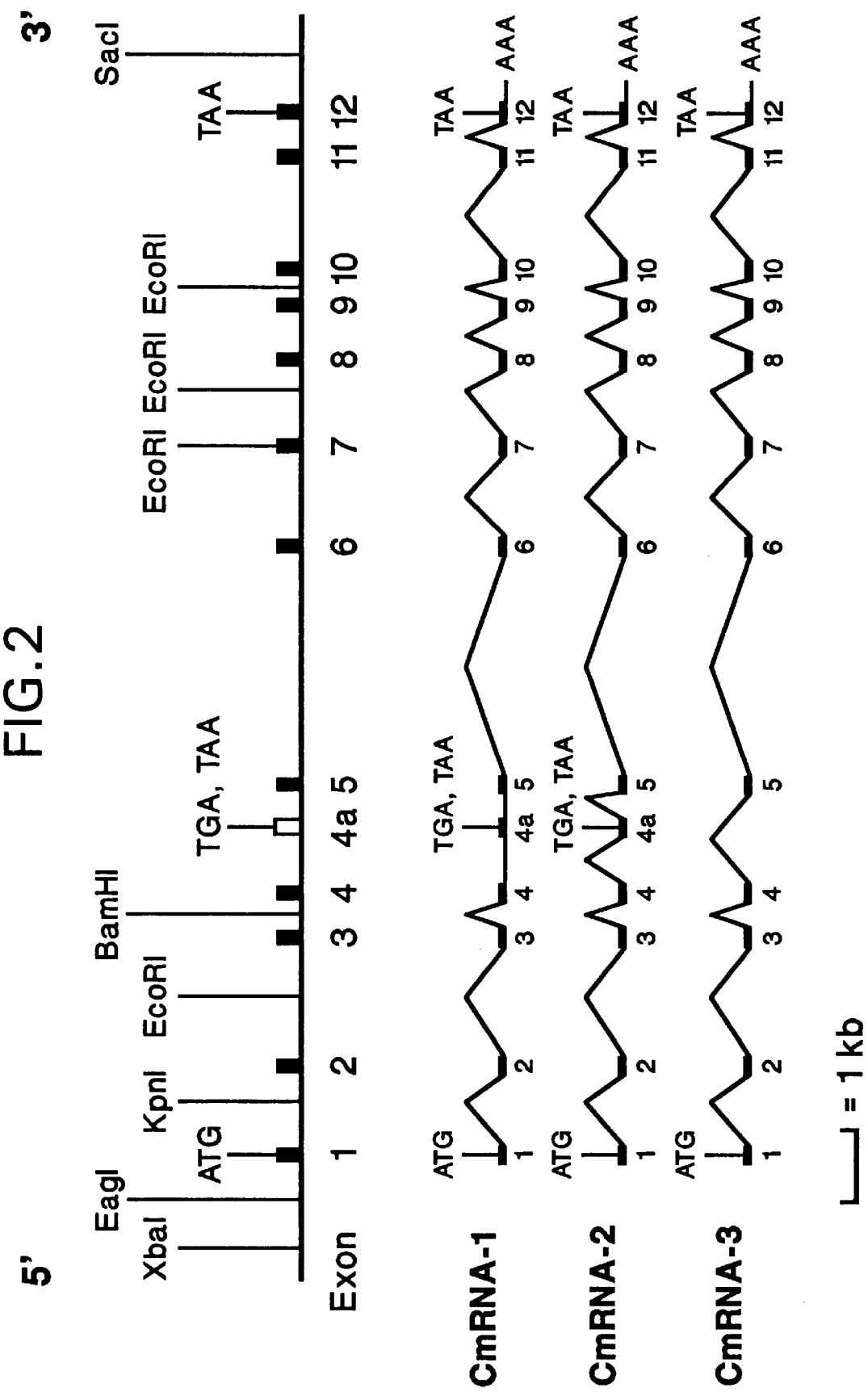
FIG. 2 depicts a schematic representation of the avian cyclin C gene. The location of the translational start site of the cyclin C protein is shown by the ATG. Similarly, the termination codon for the protein is shown by the TAA. Restriction endonuclease sites are indicated above the gene structure. The orientation of the gene is indicated above the schematic by 5' and 3'. A comparison of the isolated cyclin C mRNAs with the positions of the exons and introns of the gene is shown below the gene. The normal translational start codon shared by all of these mRNAs is indicated by the ATG. Both cyclin C mRNAs 1 and 2 contain exon 4a, and, therefore contain premature in-frame termination codons indicated by the TGA and TAA. Cyclin C mRNA 3 is the only mRNA capable of encoding an intact cyclin C ORF. Polyadenylation of these mRNAs is indicated by the AAA sequence. GenBank accession numbers for the avian genomic cyclin C sequences are as follows: Exon 2, U40875; Exon 3, U40876; Exon 4, U40877; Exon 4a, U40878; Exon 5, U40879; Exon 6, U40880; Exon 7, U40881; Exon 8, U40882; Exon 9, U40883; Exon 10, U40884; Exon 11, U40885; Exon 12, U40886.

The present invention describes a novel amino acid polymer a truncated cyclin C that plays an important role in the regulation of RNA transcription by acting to attenuate the cyclin C/cdk8 complex activity. The present invention includes nucleic acids that specifically encode such an amino acid polymer including two particular alternatively spliced cyclin C mRNAs (CmRNA-1, CmRNA-2) a DNA having a nucleotide sequence of SEQ ID NO:2, and a corresponding RNA to that recombinant DNA. The present invention further includes methods of making, detecting, isolating, and using the amino acid polymer as a cell cycle marker protein. The present invention more specifically includes a truncated human cyclin C. The human truncated cyclin C has the amino acid sequence of SEQ ID NO:52. In addition, the present invention includes an alternatively spliced human mRNA which encodes a cyclin C containing additional codes sequences derived from exons 11 and 12 in the human cyclin C cDNA. The alternatively spliced human mRNA encodes an amino acid polymer having an alternative carboxy-terminal end, relative to cyclin C. This protein is more long-lived than cyclin C and may be used as a stable analog of human cyclin C. Antibodies raised against the amino acid polymers of the present invention, their use for detection of the amino acid polymers of the present invention, corresponding antisense nucleic acids and ribozymes are also disclosed.

Figure 1A:
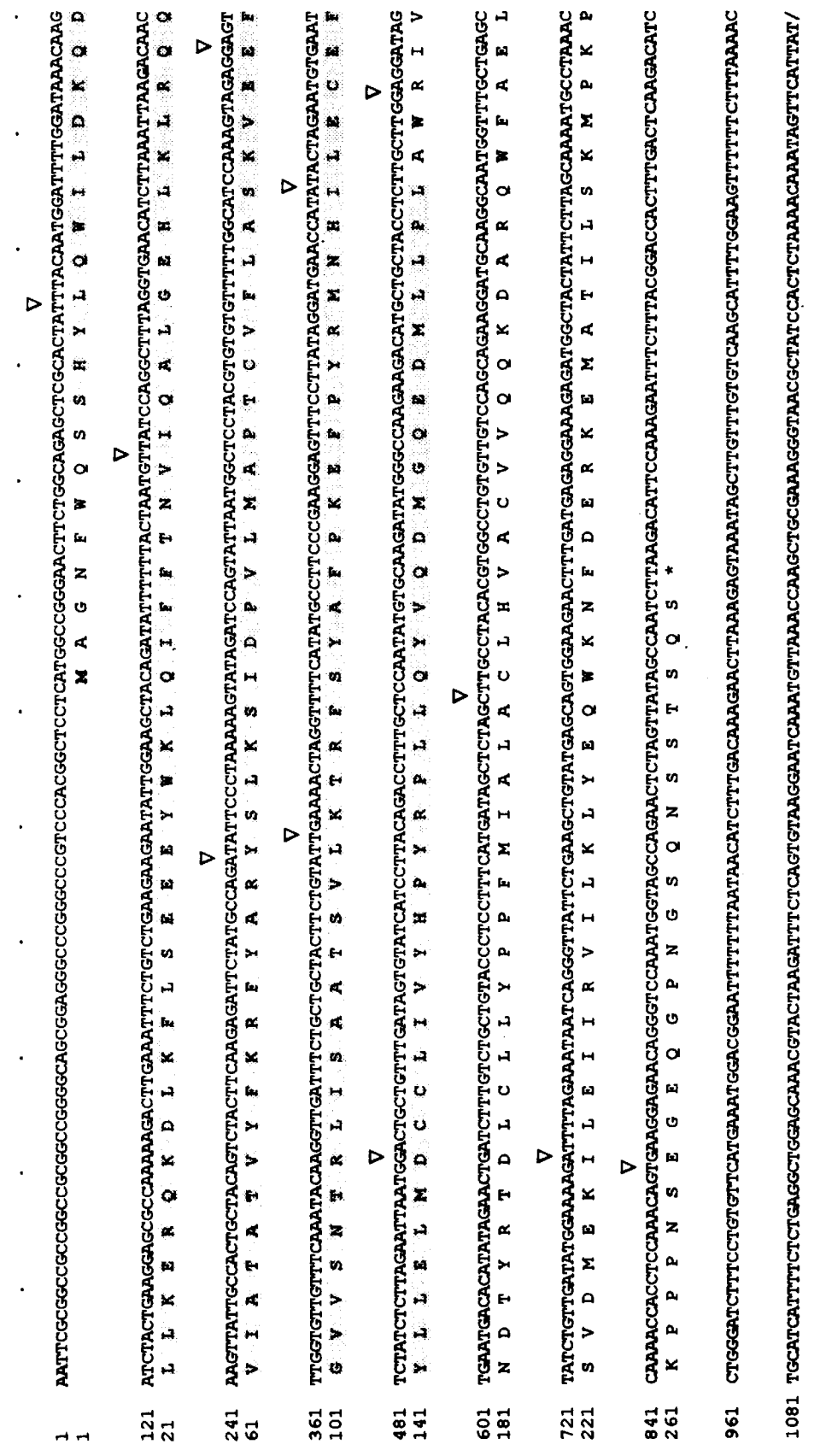

An amino acid polymer that binds cdk8 and hinders the cyclin C/cdk8 complex activity As noted above, the present invention provides an amino acid polymer (a cyclin C/cdk8 inhibitor) that hinders the formation of an active cyclin C/cdk8 complex. In some embodiments of the present invention the amino acid polymer also has a binding affinity for cdk8. In a specific embodiment, the cyclin C/cdk8 inhibitor is a truncated cyclin C with a sequence set forth in SEQ ID NO:4 (see, FIG. 1B). In another specific embodiment, the truncated cyclin C has an amino acid sequence of SEQ ID NO:52.

The term "hinders" as used herein, is meant to encompass a mild inhibition, a complete inhibition and all intermediary states of inhibition.

The phrase "hinders the formation of an active cyclin C-cdk8 complex" as used herein, includes inhibiting the formation of a cyclin C-cdk8 complex, by for example binding cdk8 in a competitive manner with cyclin C; inhibiting the activity of an existing cyclin C-cdk8 complex, for example by forming a tertiary complex with cyclin C and cdk8; and any combination of these two inhibitory mechanisms.

The term "amino acid polymer" as used herein, is used interchangeably with the term "polypeptide" and denotes a polymer comprising amino acids connected by peptide bonds.

The term "cyclin C/cdk8 inhibitor" is used herein to denote "the amino acid polymer" which corresponds to the "truncated cyclin C" of the present invention. One such specific amino acid polymer of the invention is the truncated cyclin C having the amino acid sequence set forth in SEQ ID NO:4. Another is the truncated cyclin C having an amino acid sequence of SEQ ID NO:52.

For cyclin C, the "cyclin box region" extends from amino acid 9 to amino acid 175. The exact requirements for a functional cyclin box region (which is necessary for physical interaction of a cdk with an appropriate cyclin) are loosely defined by a region of shared protein sequence homology. However, it should be recognized that there is no evidence that this entire region is required for many of the cyclin-cdk interactions; only cyclin A/ckd2 has been examined (Lees et al., *Mol. Cell. Biol.* 13:1194–1201 (1993)). In fact, studies by Lee et al. (*Proc. Natl. Acad Sci., USA* 93:3859–3263 (1996)) demonstrate that a novel 35 kDa protein (p35) found in post-mitotic neurons can bind to a cdk and regulate its function, much like a "conventional" cyclin. However, p35 has very limited sequence homology to any of the members of the cyclin gene family (i.e., cyclin A, cyclin B, cyclin C, cyclin D1, D2, D3, cyclin E, cyclin E, and cyclin G).

The invention further provides an antigenic fragment of the cyclin C/cdk8 inhibitor, which can be used, e.g., after conjugation with a carrier protein, to generate antibodies to the cyclin C/cdk8 inhibitor. Furthermore, as set forth below, the present invention contemplates the cyclin C/cdk8 inhibitor containing synthetic amino acids, derivitized by acetylation or phosphorylation, or substituted with conservative amino acids that provide the same biochemical properties.

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

Proteins having a slightly altered amino acid sequence from that described herein and presented in FIG. 1B (SEQ ID NO:4), but displaying substantially equivalent activity are contemplated by the present invention. These modifications may be deliberate, for example, such as modifications obtained through site-directed mutagenesis, or may be accidental, such as those obtained through mutations in hosts that are producers of the complex or its named subunits.

The amino acid residues described herein are preferred to be in the "L" isomeric form and include both naturally occurring amino acids as well as amino acid analogs such as norleucine. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxyl group present at the carboxyl terminus of a polypeptide.

It should be noted that all amino acid residue sequences are represented herein by formulae whose left and right orientation is in the conventional direction of amino-terminus to carboxyl-terminus. Furthermore, it should be noted that a dash at the beginning or end of an amino acid residue sequence indicates a peptide bond to a further sequence of one or more amino-acid residues.

The amino acid polymers of the present invention may be obtained in several ways including by isolation from animal cells, by synthetic means such as solid-phase peptide synthesis or by isolation from recombinant cells that contain one or more copies of a DNA transcript encoding the cyclin C/cdk8 inhibitor.

The term "polypeptide" is used in its broadest sense to refer to a compound of two or more subunit amino acids, amino acid analogs, or peptidomimetics. The subunits may be linked by peptide bonds. In another embodiment, the subunit may be linked by other the bonds, e.g., ester, ether, etc. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

Synthetic polypeptides, prepared using the well known techniques of solid phase, liquid phase, or peptide condensation techniques, or any combination thereof, can include natural and unnatural amino acids. Amino acids used for peptide synthesis may be standard Boc ($N^\alpha$-amino protected $N^\alpha$-t-butyloxycarbonyl) amino acid resin with the standard de-protecting, neutralization, coupling and wash protocols of the original solid phase procedure of Merrifield (*J Am. Chem. Soc.* 85:2149–2154 (1963)), or the base-labile $N^\alpha$-amino protected 9-fluorenylmethoxycarbonyl (Fmoc) amino acids first described by Carpino et al. (*J. Org. Chem.*

37:3403–3409 (1972)). Both Fmoc and Boc $N^\alpha$-amino protected amino acids can be obtained from Fluka, Bachem, Advanced Chemtech, Sigma, Cambridge Research Biochemical, Bachem, or Peninsula Labs or other chemical companies familiar to those who practice this art. In addition, the method of the invention can be used with other $N^\alpha$-protecting groups that are familiar to those skilled in this art. Solid phase peptide synthesis may be accomplished by techniques familiar to those in the art and provided, for example, in Stewart and Young, 1984, Solid Phase Synthesis, Second Edition, Pierce Chemical Co., Rockford, Ill.; Fields et al., *Int. J. Pept. Protein Res.* 35:161–214 (1990), or using automated synthesizers, such as sold by ABS. Thus, polypeptides of the invention may comprise D-amino acids, a combination of D- and L-amino acids, and various "designer" amino acids (e.g., β-methyl amino acids, Cα-methyl amino acids, and Nα-methyl amino acids, etc.) to convey special properties. Synthetic amino acids include ornithine for lysine, fluorophenylalanine for phenylalanine, and norleucine for leucine or isoleucine. Additionally, by assigning specific amino acids at specific coupling steps, α-helices, β turns, β sheets, γ-turns, and cyclic peptides can be generated.

In one aspect of the invention, the peptides may comprise a special amino acid at the C-terminus which incorporates either a $CO_2H$ or $CONH_2$ side chain to simulate a free glycine or a glycine-amide group. Another way to consider this special residue would be as a D or L amino acid analog with a side chain consisting of the linker or bond to the bead. In one embodiment, the pseudo-free C-terminal residue may be of the D or the L optical configuration; in another embodiment, a racemic mixture of D and L-isomers may be used.

The present invention further provides for determination of the structure of the amino acid polymers of the present invention, which can be provided in sufficient quantities by recombinant expression (infra) or by synthesis. This is achieved by assays based on the physical or functional properties of the product, including radioactive labeling of the product followed by analysis by gel electrophoresis, immunoassay, etc.

The structure of the amino acid polymers of the present invention can be analyzed by various methods known in the art. Structural analysis can be performed by identifying sequence similarity with other known proteins. The degree of similarity (or homology) can provide a basis for predicting structure and fuiction of the cyclin C/cdk8 inhibitor, or a domain thereof. In a specific embodiment, sequence comparisons can be performed with sequences found in GenBank, using, for example, the FASTA and FASTP programs (Pearson et al., *Proc. Natl. Acad. Sci., USA* 85:2444–48 (1988)).

The protein sequence can be further characterized by a hydrophilicity analysis (e.g., Hopp et al., *Proc. Natl. Acad. Sci., USA* 78:3824 (1981)). A hydrophilicity profile can be used to identify the hydrophobic and hydrophilic regions of the cyclin C/cdk8 inhibitor.

Secondary structural analysis (e.g., Chou et al., *Biochemistry* 13:222 (1974)) can also be done, to identify regions of the cyclin C/cdk8 inhibitor that assume specific secondary structures.

Manipulation, translation, and secondary structure prediction, as well as open reading frame prediction and plotting, can also be accomplished using computer software programs available in the art.

By providing an abundant source of the recombinant cyclin C/cdk8 inhibitor, the present invention enables quantitative structural determination of cyclin C/cdk8 inhibitor, or domains thereof. In particular, enough material is provided for nuclear magnetic resonance (NMR), infrared (IR), Raman, and ultraviolet (UV), and circular dichroism (CD) spectroscopic analysis. In particular NMR provides very powerful structural analysis of molecules in solution, which more closely approximates their native environment (Marion et al., *Biochem. Biophys. Res. Comm.* 113:967–974 (1983); Bar et al., *J. Magn. Reson.* 65:355–360 (1985); Kimura et al., *Proc. Natl. Acad. Sci., USA* 77:1681–1685 (1980)). Other methods of structural analysis can also be employed. These include but are not limited to X-ray crystallography (Engstom, *Biochem. Exp. Biol.* 11:7–13 (1974)).

More preferably, co-crystals of cyclin C/cdk8 inhibitor as a complex with cdk8 and/or the cyclin C/cdk8 complex can be studied. Analysis of co-crystals provides detailed information about binding, which in turn allows for rational design of ligand agonists and antagonists. Computer modeling can also be used, especially in connection with NMR or X-ray methods (Fletterick, R. and Zoller, M. (eds.), 1986, Computer Graphics and Molecular Modeling, in *Current Communications in Molecular Biology, Cold Spring Harbor Laboratory, Cold Spring Harbor, N.Y.*).

Nucleic Acids Encoding the Cyclin C/cdk8 inhibitor

The present invention includes isolation of mRNA encoding an cyclin C/cdk8 inhibitor factor of the invention, as well as all of the mRNAs encoding the amino acid polymers of the present invention, including naturally occurring forms of the amino acid polymers, and any antigenic fragments thereof from any animal, particularly mammalian or avian, and more particularly human, source.

In the practice of the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach,* Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology,* John Wiley & Sons, Inc. (1994).

Therefore, if appearing herein, the following terms shall have the definitions set out below.

As used herein, the term "gene" refers to an assembly of nucleotides that encode a polypeptide, and includes genomic DNA nucleic acids which can contain a complete set of introns and exons, and cDNA.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

"Heterologous" DNA refers to DNA not naturally located in the cell, or in a chromosomal site of the cell. Preferably, the heterologous DNA includes a gene foreign to the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogues thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS. Moderate stringency hybridization conditions correspond to a higher $T_m$, e.g., 40% formamide, with 5× or 6× SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 18 nucleotides; preferably at least about 36 nucleotides; and more preferably the length is at least about 48 nucleotides.

In a specific embodiment, the term "standard hybridization conditions" refers to a $T_m$ of 55 ° C., and utilizes conditions as set forth above. In a preferred embodiment, the $T_m$ is 60° C.; in a more preferred embodiment, the $T_m$ is 65° C.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc.) (Reeck et al., *Cell* 50:667 (1987)).

Accordingly, the term "sequence similarity" in all its grammatical forms refers to the degree of identity or correspondence between nucleic acid or amino acid sequences of proteins that do not share a common evolutionary origin (see Reeck et al., supra). However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Similarly, in a particular embodiment, two amino acid sequences are "substantially homologous" or "substantially similar" when greater than 30% of the amino acids are identical, or greater than about 60% are similar (functionally identical). Preferably, the similar or homologous sequences are identified by alignment using, for example, the GCG (Genetics Computer Group, Program Manual for the GCG Package, *Version* 7, Madison, Wis.) pileup program.

The term "corresponding to" is used herein to refer to similar or homologous sequences, whether the exact position is identical or different from the molecule to which the similarity or homology is measured. The term "corresponding to" refers to the sequence similarity, and not the numbering of the amino acid residues or nucleotide bases.

A gene encoding an amino acid polymer of the present invention, whether genomic DNA or cDNA, can be isolated from any source, particularly from a human cDNA or genomic library. Methods for obtaining the gene are well known in the art, as described above (see, e.g., Sambrook et al., supra). Accordingly, any animal cell potentially can serve as the nucleic acid source for the molecular cloning of the gene. The DNA may be obtained by standard procedures known in the art from cloned DNA (e.g., a DNA "library"), by chemical synthesis, by cDNA cloning, or by the cloning of genomic DNA, or fragments thereof, purified from the desired cell (See, for example, Sambrook et al., supra; Glover, D.M. (ed.), 1985, DNA Cloning: A Practical Approach, MRL Press, Ltd., Oxford, U.K. Vol. 1, II). Clones derived from genomic DNA may contain regulatory and intron DNA regions in addition to coding regions; clones derived from cDNA will not contain intron sequences other than those portions included by alternative splicing. Whatever the source, the gene should be molecularly cloned into a suitable vector for propagation of the gene.

Identification of the specific DNA fragment containing the desired gene may be accomplished in a number of ways. For example, if an amount of a portion of the gene or its specific RNA, or a fragment thereof, is available and can be purified and labeled, the generated DNA fragments may be screened by nucleic acid hybridization to a labeled probe (Benton et al., *Science* 196:180 (1977); Grunstein et al., *Proc. Natl. Acad. Sci., USA* 72:3961 (1975)). For example, a set of oligonucleotides corresponding to the partial amino acid sequence information obtained for an amino acid polymer of the present can be prepared and used as probes for DNA encoding that protein, or as primers for cDNA or mRNA (e.g., in combination with a poly-T primer for RT-PCR). Preferably, a fragment is selected that is highly unique to the particular amino acid polymer. Those DNA fragments with substantial homology to the probe will hybridize. As noted above, the greater the degree of homology, the more stringent hybridization conditions can be used. In a specific embodiment, high stringency hybridization conditions are used to identify an homologous mRNA for the particular mRNAs of the present invention.

Further selection can be carried out on the basis of the properties of the gene and its alternative splice sites, e.g., if the alternative splice sites facilitate the formation of an MRNA that encodes a protein product having the isoelectric, electrophoretic, amino acid composition, or partial amino acid sequence of the amino acid polymers as disclosed herein. Thus, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing or non-equilibrium pH gel electrophoresis behavior, proteolytic digestion maps, or antigenic properties as known for the particular amino acid polymer. For example, the ability of a cyclin C/cdk8 inhibitor to bind to cdk8 and to hinder the active cyclin C/cdk8 complex is indicative of its identity as an cyclin C/cdk8 inhibitor of the present invention.

The present invention also relates to cloning vectors containing genes encoding analogs and derivatives of the amino acid polymers of the present invention, that have the same or homologous functional activity as the particular amino acid polymer, and homologs thereof from other species. The production and use of derivatives and analogs related to amino acid polymers of the present invention are within the scope of the present invention. In a specific embodiment, the derivative or analog is functionally active, e.g., capable of exhibiting one or more functional activities associated with a wild-type cyclin C/cdk8 inhibitor of the invention. Derivatives can be made by altering the encoding nucleic acid sequences by substitutions, additions or deletions that provide for functionally equivalent molecules. Preferably, derivatives are made that have enhanced or increased functional activity relative to the native cyclin C/cdk8 inhibitor, or have greater stability than the amino acid polymer.

Due to the degeneracy of nucleotide coding sequences, other DNA and/or MRNA sequences which encode substantially the same amino acid sequence as an amino acid polymer of the present invention may be used in the practice of the present invention. These include but are not limited to allelic genes, homologous genes from other species, and nucleotide sequences comprising all or portions of nucleic acids encoding such amino acid polymer which are altered by the substitution of different codons that encode the same amino acid residue within the sequence, thus producing a silent change. Likewise, such derivatives include, but are not limited to, those containing, as a primary amino acid sequence, all or part of the amino acid sequence of an amino acid polymer of the present invention, e.g., as set forth in SEQ ID NO:4, SEQ ID NO:50, or SEQ ID NO:52, including altered sequences in which functionally equivalent amino acid residues are substituted for residues within the sequence resulting in a conservative amino acid substitution. Substitution of one or more amino acid residues within the sequence by an amino acid of a similar polarity, which acts as a functional equivalent, may result in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred substitutions are:

Lys for Arg and vice versa such that a positive charge may be maintained;

Glu for Asp and vice versa such that a negative charge may be maintained;

Ser for Thr such that a free -OH can be maintained; and

Gln for Asn such that a free $NH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces P-turns in the protein's structure.

The genes encoding the amino acid polymer derivatives and analogs of the invention can be produced by various methods known in the art. The manipulations which result in their production can occur at the gene or protein level. For example, a cloned gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of an amino acid polymer of the present invention, care should be taken to ensure that the modified gene remains within the same translational reading frame as the native nucleic acid, uninterrupted by translational stop signals, in the region where the desired activity is encoded.

Additionally, a nucleic acid sequence encoding an amino acid polymer of the present invention can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity of the mutated gene product. Any technique for mutagenesis known in the art can be used, including but not limited to, in vitro site-directed mutagenesis (Hutchinson, et al., *J. Biol. Chem.* 253:6551 (1978); Zoller et al., *DNA* 3:479–488 (1984); Oliphant et al., *Gene* 44:177 (1986); Hutchinson et al., *Proc. Natl. Acad. Sci., USA* 83:710 (1986)), use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification,* H. Erlich, ed., Stockton Press, Chapter 6, pp. 61–70).

In a specific embodiment, a truncated cyclin C fusion protein can be expressed. A truncated cyclin C fusion protein comprises at least a functionally active portion of a another protein joined via a peptide bond to at least a functionally active portion of a truncated cyclin C polypeptide. The sequences of the other protein can be amino- or carboxy-terminal to the truncated cyclin C sequences. A recombinant DNA molecule encoding such a fusion protein comprises a sequence encoding at least a functionally active portion of the other protein joined in-frame to the truncated cyclin C coding sequence, and preferably encodes a cleavage site for a specific protease, e.g., thrombin or Factor Xa, preferably at the junction of the other protein and the truncated cyclin C. In a specific embodiment, the other protein is glutathione-S-transferase (GST) and the fusion protein is a GST-truncated cyclin C fusion protein that bind directly to cdk8 in vitro, including radiolabeled cdk8. In another embodiment, the other protein is green fluorescent protein (GFP) and the fusion protein is a GFP-truncated cyclin C fusion protein.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli,* and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences form the yeast 2µ plasmid.

Expression of the Amino Acid Polymers of the Present Invention

The nucleotide sequence coding for an amino acid polymer of the present invention, or antigenic fragment, derivative or analog thereof, or a functionally active derivative, including a chimeric protein, thereof, can be inserted into an appropriate expression vector, i.e., a vector which contains the necessary elements for the transcription and translation of the inserted protein-coding sequence. Such elements are termed herein a "promoter." Thus, the nucleic acid encoding an amino acid polymer of the invention is operationally associated with a promoter in an expression vector of the invention. Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native gene encoding the amino acid polymer and/or its flanking regions.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage DNA, plasmid DNA, or cosmid DNA. The expression elements of vectors vary in their strengths and specificities. Depending on the host-vector system utilized, any one of a number of suitable transcription and translation elements may be used.

A recombinant protein of the present invention, or functional fragment, derivative, chimeric construct, or analog thereof, may be expressed chromosomally, after integration of the coding sequence by recombination. In this regard, any of a number of amplification systems may be used to achieve high levels of stable gene expression (See Sambrook et al., 1989, supra).

The cell into which the recombinant vector comprising the nucleic acid encoding the amino acid polymer is cultured in an appropriate cell culture medium under conditions that provide for expression of amino acid polymer by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of the amino acid polymer may be controlled by any promoter/enhancer element known in the art, but these regulatory elements must be functional in the host selected for expression. Promoters which may be used to control cyclin C/cdk8 inhibitor gene expression include, but are not limited to, the SV40 early promoter region (Benoist et al., *Nature* 290:304–310 (1981)), the promoter contained in the 3' long terminal repeat of Rous sarcoma virus (Yamamoto et al., *Cell* 22:787–797 (1981)), the herpes thymidine kinase promoter (Wagner et al., *Proc. Natl. Acad. Sci., USA* 78:1441–1445 (1981)), the regulatory sequences of the metallothionein gene (Brinster et al. *Nature,* 296:39–42 (1986)); prokaryotic expression vectors such as the β-lactamase promoter (Villa-Kamaroff et al., *Proc. Natl. Acad. Sci., USA* 75:3727–3731 (1978)), or the tac promoter (DeBoer et al. *Proc. Natl. Acad. Sci., USA* 80:21–25 (1983)); see also "Useful proteins from recombinant bacteria" in *Scientific American* 242:74–94 (1980); promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., *Cell* 38:639–646 (1984); Ornitz et al., *Cold Spring Harbor Symp. Quant. Biol.* 50:399–409 (1986); MacDonald, *Hepatology* 7:425–515 (1984)); insulin gene control region which is active in pancreatic beta cells (Hanahan, *Nature* 315:115–122 (1985)), immunoglobulin gene control region which is active in lymphoid cells (Grosschedl et al. *Cell,* 38:647–658 (1984); Adames et al., *Nature* 318:533–538 (1984); Alexander et al., *Mol. Cell. Biol.* 7:1436–1444 (1984)), mouse mammary tumor virus control region which is active in testicular, breast, lymphoid and mast cells (Leder et al., *Cell,* 45:485–495 (1986)), albumin gene control region which is active in liver (Pinkert et al., *Genes and Devel.* 1:268–276 1987)), alpha-fetoprotein gene control region which is active in liver (Krunlauf et al., *Mol. Cell. Biol.* 5:1639–1648 (1985); Hammer et al. *Science* 235:53–58 (1987)), alpha 1-antitrypsin gene control region which is active in the liver (Kelsey et al., *Genes and Devel.,* 1:161–171 (1987)), beta-globin gene control region which is active in myeloid cells (Mogram et al., *Nature* 315:338–340 (1985); Kollias et al., *Cell* 46:89–94 (1986)), myelin basic protein gene control region which is active in oligodendrocyte cells in the brain (Readhead et al., *Cell* 48:703–712 1987)), myosin light chain-2 gene control region which is active in skeletal muscle (Sani, *Nature* 314:283–286 (1985)), and gonadotropic releasing hormone gene control region which is active in the hypothalamus (Mason et al., *Science* 234:1372–1378 (1985)).

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al.,*J. Biol. Chem.* 267:963–967 (1984); Wu et al., *J. Biol. Chem.* 263:14621–14624 (1988); Hartmut et al., Canadian Patent Application No. 2,012,311, filed Mar. 15, 1990).

Transgenic Animal Models of truncated cyclin C Activity

As noted above, the functional activity of truncated cyclin C or the stabilized cyclin C exemplified by the amino acid polymer having the amino acid sequence of SEQ ID NO:50 can be evaluated transgenically. In this respect, a transgenic mouse (or other animal) model can be used. A DNA fragment encoding truncated cyclin C (hereafter referred to as the "truncated cyclin C gene") for example, can be introduced transgenically using standard techniques, either to provide for over expression of the protein, or to complement animals defective in the protein. Transgenic vectors, including viral vectors, or cosmid clones (or phage clones) corresponding to the wild type locus of candidate gene, can be constructed using the isolated DNA fragment encoding truncated cyclin C, as described below. Cosmids may be introduced into transgenic mice using published procedures (Jaenisch, *Science* 240:1468–1474 (1988)).

Alternatively, truncated cyclin C genes can be tested by examining their phenotypic effects when expressed in antisense orientation in wild-type animals. In this approach, expression of the wild-type allele is suppressed, which leads to a mutant phenotype. RNA·RNA duplex formation (antisense-sense) prevents normal handling of mRNA, resulting in partial or complete elimination of wild-type gene effect. This technique has been used to inhibit TK synthesis in tissue culture and to produce phenotypes of the Kruppel mutation in Drosophila, and the Shiverer mutation in mice (Izant et al., *Cell* 36:1007–1015 (1984); Green et al., *Annu. Rev. Biochem.* 55:569–597 (1986); Katsuki et al., *Science* 241:593–595 (1988)). An important advantage of this approach is that only a small portion of the gene need be expressed for effective inhibition of expression of the entire cognate MRNA. (This technique is particularly advantageous in the present invention, since in some embodiments the full-length form of cyclin C is expressed and only the truncated cyclin C is eliminated.) The antisense transgene will be placed under control of its own promoter or another promoter expressed in the correct cell type, and placed upstream of the SV40 polyA site. This transgene can be used to make transgenic mice, or by using gene knockout technology.

Antibodies to the Amino Acid Polymers of the Present Invention

According to the present invention, amino acid polymers of the present invention produced recombinantly or by chemical synthesis, and fragments or other derivatives or analogs thereof, including fusion proteins, may be used as an immunogen to generate antibodies that recognize specific and unique portions of these polypeptides. Such antibodies include but are not limited to polyclonal, monoclonal (Kohler et aL, *Nature* 256:495–497 (1975); Kozbor et al., *Immunology Today* 4:72 (1983); Cole et al., in *Monoclonal Antibodies and Cancer Therapy,* Alan R. Liss, Inc., pp. 77–96 (1985); PCT/US90/02545; Cote et al., *Proc. Natl. Acad. Sci., USA* 80:2026–2030 (1983)), chimeric (Morrison et al., *J. Bacteriol.* 159–870 (1984); Neuberger et al., *Nature* 312:604–608 (1984); Takeda et al., *Nature* 314:452–454 (1985)), single chain (U.S. Pat. No. 4,946,778), Fab fragments, and an Fab expression library. The antibodies of the invention may be cross reactive over species, e.g., they may recognize homologous proteins from different species. Polyclonal antibodies have greater likelihood of cross reactivity. Alternatively, an antibody of the invention may be specific for a single form of an amino acid polymer of the present invention such an antibody specific for the human truncated cyclin C.

For the production of polyclonal antibody, various host animals can be immunized by injection, including but not limited to rabbits, mice, rats, sheep, goats, etc. In one embodiment, for example the cyclin C/cdk8 inhibitor polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an amino acid polymer of the present invention, one may assay generated hybridomas for a product which binds to the amino acid polymer fragment containing such epitope. For selection of an antibody specific to such an amino acid polymer from a particular species of animal, one can select on the basis of positive binding with the amino acid polymer expressed by or isolated from cells of that species of animal.

The foregoing antibodies can be used in methods known in the art relating to the localization and activity of the amino acid polymer, e.g., for Western blotting, imaging the polypeptide in situ, measuring levels thereof in appropriate physiological samples, etc.

Inhibition of Cyclin C/cdk8 inhibitor Expression

The present invention extends to the preparation of antisense nucleotides and ribozymes that may be used to interfere with the expression of the cyclin C/cdk8 inhibitor at the translational level. This approach utilizes antisense nucleic acid and ribozymes to block translation of a specific mRNA, either by masking that mRNA with an antisense nucleic acid or cleaving it with a ribozyme. Such approaches also may be used to interfere with the expression of the stabilized human cyclin C exemplified by the amino acid polymer having an amino acid sequence of SEQ ID NO:50.

Antisense nucleic acids are DNA or RNA molecules that are complementary to at least a portion of a specific mRNA molecule (see Weintraub, 1990; Marcus-Sekura, *Anal. Biochem.* 172:298 (1988)). In the cell, they hybridize to that mRNA, forming a double stranded molecule. The cell does not translate an mRNA in this double-stranded form. Therefore, antisense nucleic acids bind mRNA and thereby interfere with the expression of the protein encoded by the mRNA. Oligomers of about fifteen nucleotides and molecules that hybridize to the AUG initiation codon will be particularly efficient, since they are easy to synthesize and are likely to pose fewer problems than larger molecules when introducing them into organ cells.

Antisense methods have been used to inhibit the expression of many genes in vitro (Marcus-Sekura, supra; Hambor et al., *J. Exp. Med.* 168:1237 (1988)). Preferably synthetic antisense nucleotides contain phosphoester analogs, such as phosphorothiolates, or thioesters, rather than natural phosphoester bonds. Such phosphoester bond analogs are more resistant to degradation, increasing the stability, and therefore the efficacy, of the antisense nucleic acids.

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech, *J. Am. Med. Assoc.* 260:3030 (1988)). Because they are sequence-specific, only mRNAs with particular sequences are inactivated.

Investigators have identified two types of ribozymes, Tetrahymena-type and "hammerhead"-type (Hasselhoff and Gerlach, 1988). Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

Therapeutic Methods and Gene Therapy

Various diseases or disorders mediated by inappropriate cell cycle activity due to increased or decreased activity of the cyclin C/cdk8 inhibitor of the invention may be addressed by introducing genes that encode either antisense or ribozyme molecules that inhibit expression of the cyclin C/cdk8 inhibitor (where the disease or disorder is associated with excessive cyclin C/cdk8 inhibitor activity), or the cyclin C/cdk8 inhibitor (where the disease or disorder is associated with decreased cyclin C/cdk8 inhibitor activity). In addition, in vitro or in vivo transfection with one of the foregoing genes may be useful for evaluation of cell cycle activity in an animal model, which in turn may serve for drug discovery and evaluation.

In a specific embodiment, the present invention is directed to the treatment of tumors and other cancers by modulating the activity of a truncated cyclin C, e.g., by enhancing or inhibiting expression of the cyclin C/cdk8 inhibitor to increase or decrease its activity. In specific embodiments, the invention provides for introducing an antisense nucleotide or a ribozyme specific for the alternatively spliced MRNA to inhibit truncated cyclin C activity. In this instance, increased expression of genes indirectly under control of truncated cyclin C may be necessary to restore appropriate cell cycle and growth characteristics to a transformed cell, in which case a transgene vector of the invention for expression of truncated cyclin C can be used. Under other circumstances, control of proliferation of a cancer cell is accomplished by maintaining an active cyclin C/cdk8 complex, thereby regulating uncontrolled cell proliferation characteristic of cancer cells. As the present invention provides for detecting the level and activity of truncated cyclin C in cells, such as cancer cells, specifically tumor cells, the need to increase or decrease the activity of truncated cyclin C in a given cell can be readily determined.

Examples of tumors that can be treated according to the invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

In another embodiment, dysproliferative changes (such as metaplasias and dysplasias) are treated or prevented in epithelial tissues such as those in the cervix, esophagus, and lung. Thus, the present invention provides for treatment of conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, *Basic Pathology,* 2d Ed., W.B. Saunders Co., Philadelphia, pp. 68–79). Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder. For a review of such disorders, see Fishman et al., *Medicine,* 2d Ed., J. B. Lippincott Co., Philadelphia (1985).

In one embodiment, a gene for regulation of truncated cyclin C (e.g., an antisense gene) is introduced in vivo in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, in a specific embodiment, tumors can be specifically targeted. Examples of particular vectors include, but are not limited to, a defective herpes virus 1 (HSV1) vector (Kaplitt et al., *Molec. Cell. Neurosci.* 2:320–330 (1991)), an attenuated adenovirus vector, such as the vector described by Stratford-Perricaudet et al. (*J. Clin. Invest.,* 90:626–630 (1990)), and a defective adeno-associated virus vector (Samulski et al., *J. Virol.* 61:3096–3101 (1987); Samulski et al. *J. Virol.,* 63:3822–3828 (1989)).

Preferably, for in vitro administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-$\gamma$ (IFN-$\gamma$), or anti-CD4 antibody, can be administered to block humoral or cellular immune responses to the viral vectors (see, e.g., Wilson, *Nature Medicine* (1994)). In addition, it is advantageous to employ a viral vector that is engineered to express a minimal number of antigens.

In another embodiment the gene can be introduced in a retroviral vector, e.g., as described in Anderson et al., U.S. Pat. No. 5,399,346; Mann et al., *Cell* 33:153 (1983); Temin et al., U.S. Pat. No. 4,650,764; Temin et al., U.S. Pat No.. 4,980,289; Markowitz et al., *J. Virol.* 62:1120 (1988); Temin et al., U.S. Pat. No. 5,124,263; International Patent Publication No. WO 95/07358, published Mar. 16, 1995, by Dougherty et al.; and Kuo et al., *Blood* 82:845 (1993).

Targeted gene delivery is described in International Patent Publication WO 95/28494, published October 1995.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Feigner et al., *Proc. Natl. Acad. Sci., USA* 84:7413–7417 (1987); see Mackey et al., *Proc. Natl. Acad. Sci., USA* 85:8027–8031 (1988)). The use of cationic lipids may promote encapsulation of negatively charged nucleic acids, and also promote fusion with negatively charged cell membranes (Feigner et al., *Science* 337:387–388 (1989)). The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancreas, liver, kidney, and the brain. Lipids may be chemically coupled to other molecules for the purpose of targeting (see Mackey et al., 1988, supra). Targeted peptides, e.g., hormones or neurotransmitters, and proteins such as antibodies, or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., Wu et al., *J. Biol. Chem.* 267:963–967 (1992); Wu et al., 1988, Hartmut et al., supra).

Detection of an Amino Acid Polymer of the Present Invention

As suggested earlier, the diagnostic method of the present invention comprises examining a cellular sample or medium by means of an assay including an effective amount of a binding partner of the amino acid polymer, such as an anti-cyclin C/cdk8 inhibitor antibody, preferably an affinity-purified polyclonal antibody, and more preferably a mAb, or oligonucleotide containing the specific sequence.

The present invention also relates to a variety of diagnostic applications, including methods for detecting the presence of stimuli such as the earlier referenced polypeptide ligands, by reference to their ability to elicit the activities which are mediated by the present cyclin C/cdk8 inhibitor. As mentioned earlier, the cyclin C/cdk8 inhibitor can be used to produce antibodies to itself by a variety of known techniques, and such antibodies could then be isolated and utilized as in tests for the presence of particular transcription activation activity in suspect target cells.

The procedures and their application are all familiar to those skilled in the art and accordingly may be utilized within the scope of the present invention. For example, a "competitive" procedure is described in U.S. Pat. Nos. 3,654,090 and 3,850,752. A "sandwich" procedure is described in U.S. Pat. Nos. RE 31,006 and 4,016,043. Still other procedures are known such as the "double antibody," or "DASP" procedure.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

An amino acid polymer of the present invention or its binding partner(s) can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

Other means for detecting specific binding are well known in the art, including biosensors such as the BIAcore™ system (Pharmacia Biosensor AB, Uppsala, Sweden), or optical immunosensor systems. These systems can be grouped into four major categories: reflection techniques; surface plasmon resonance; fiber optic techniques, and integrated optic devices. Reflection techniques include ellipsometry, multiple integral reflection spectroscopy, and fluorescent capillary fill devices. Fiber-optic techniques include evanescent field fluorescence, optical fiber capillary tube, and fiber optic fluorescence sensors. Integrated optic devices include planer evanescent field fluorescence, input grading coupler immunosensor, Mach-Zehnder interferometer, Hartman interferometer and difference interferometer sensors. Holographic detection of binding reactions is accomplished detecting the presence of a holographic image that is generated at a predetermined image location when one reactant of a binding pair binds to an immobilized second reactant of the binding pair (see U.S. Pat. No. 5,352,582, issued Oct. 4, 1994 to Lichtenwalter et al.).

Examples of optical immunosensors are described in general in a review article by G. A. Robins (Advances in Biosensors), Vol. 1, pp. 229–256, 1991. More specific description of these devices are found for example in U.S. Pat. Nos. 4,810,658; 4,978,503; 5,186,897; R. A. Brady et al. (*Phil. Trans. R. Soc. Land.* B 316:143–160 (1987)) and G. A. Robinson et al. (in Sensors and Actuators, Elsevier, 1992).

The following examples are presented in order to more fully illustrate the preferred embodiments of the invention. They should in no way be construed, however, as limiting the broad scope of the invention.

EXAMPLES

Various references cited herein are listed after the Examples, infra.

Example 1

ALTERNATIVELY SPLICED CYCLIN C mRNA IS WIDELY EXPRESSED, CELL CYCLE REGULATED, AND ENCODES A TRUNCATED CYCLIN BOX PROTEIN

Introduction

Screening of an avian T-cell cDNA library results in the isolation of a cyclin C homologue as well as an abundant, yet distinct, cyclin C-related CDNA. The predicted open reading frame (ORF) of the cyclin C CDNA predicted a 283 amino acid protein that is >99% identical to the human protein and 72% identical to the *Drosophila melanogaster* protein. However, the predicted ORF of the cyclin C-related CDNA predicts a much smaller 105 amino acid protein that is identical to cyclin C well into the cyclin-box region (amino acid residue 98), where it abruptly diverges and then terminates. Using PCR analysis of cDNA derived from a range of cell lines and tissues, alternative splicing of the avian cyclin C gene is demonstrated. This alternatively spliced cDNA is the result of the insertion of a unique exon containing premature termination codons within the cyclin-box region of the normal protein. (The cyclin box region includes amino acids 9-175 as determined by homology with other cyclins i.e., cyclin A, cyclin B, cyclin D1, cyclin E, etc.). Furthermore, a smaller ~19 kDa protein that co-migrates with the in vitro transcribed and translated truncated cyclin C protein is detected in normal and virally-transformed avian cells with a *Drosophila melanogaster* cyclin C antibody (Leclerc et al., supra).

Steady-state levels of the normal cyclin C mRNA and protein do not vary during the cell cycle. However, expression of alternatively spliced cyclin C mRNA and protein is regulated in a cell cycle-dependent manner with a peak in G2/M and early G1-phase, similar to the expression of cyclin B2 (Gallant et al., *J. Cell Biol.* 117:213–224 (1992)). The expression of highly conserved cyclin C and truncated cyclin C ORFs in a variety of virally-transformed cell lines and normal tissues indicates that both cyclin C and truncated cyclin C are important in regulating transcription (Leclerc et al. supra; Maldonado et al., *Nature* 381:86–89 (1996)). The truncated cyclin C protein functions as endogenously encoded cyclin C inhibitor by negatively regulating cyclin C/cdk8 complex activity, in much the same way as the cyclin dependent protein kinase inhibitors function to inhibit the D-type cyclins, cyclin A and cyclin E (Sherr et al., *Genes & Devel.* 9:1149–1163 (1995)).

MATERIALS AND METHODS

Isolation and characterization of the chicken cyclin C cDNAs and genomic clones.

Chicken cyclin C cDNAs are isolated from a chicken UG9 T-cell CDNA library (Lahti et al., *Proc. Natl. Acad. Sci., USA* 88: 10595–10960 (1991)) by low-stringency hybridization with a human cyclin C cDNA (Lew et al., supra). Twenty cDNAs are isolated from a screen of ~80,000 cDNAs, and they are subsequently grouped according to size, and later, nucleotide sequence differences. DNA sequence is determined as previously described (Bunnell et al., *Proc. Natl. Acad. Sci. USA* 87:7467–7471 (1990); Kidd et al., *Cell Growth & Differ.* 2:85–93 (1991); Xiang et al., *J. Biol. Chem.* 269:15786–15794 (1994)). The corresponding chicken gene is isolated by screening a Cornish White Rock chicken cosmid library (Stratagene) with the full-length chicken cyclin C cDNA as previously described (Eipers et al., *Genomics* 13:613–621 (1992)). EcoRI fragments containing the entire gene are subcloned into a pKS plasmid vector (Stratagene), and the resulting plasmid, as well as cosmid, DNA used for double strand DNA sequence analysis. Using oligonucleotide primers designed for sequencing the cDNA clones, all exons and intron/exon boundaries are sequenced in both directions as described (Xiang et al., supra). Oligonucleotides are spaced approximately 80–100 bp apart spanning the cDNA. All DNA sequence data is analyzed using the IntelliGenetics program. The following oligonucleotides are used for this analysis: C-1, 5' TCCAG-CAGAAGGATGCAA 3'; C-2, 5' CTCCAGCACACAGT-CAAC 3'; C-3, 5' AGGTGAACATCTTAAATT 3'; C-4, 5' TAGGAGCCATTAATACTG 3'; C-5, 5' GAC-CACTTTGACTCAAGA 3'; C-6, 5' CTGCAGAATCAC-TATACA 3'; C-7, 5' GTCCATTTCATGAACACA 3'; C-8, 5' AGCCATCTCTTTCCTCTC 3'; C-9, 5' CAAGCTAGAGC-TATCATG 3'; C-10, 5' CGCTCCTTCAGTAGATCTTG 3'; C-11, 5' TTGAAATTTCTGTCTGAA 3'; C-12, 5' AAACTCCTTCGGGAAGGC 3'; C-13,5' ATCAACAGAT-AGCTCAGC 3'; C-14, 5' GTCTTCTTGGCCCATATC 3'; C-15, 5' GTAGACTGTAGCAGTGGC 3'; C-16, 5' GCATC-CAAAGTAGAGGAG 3'; C-1 7, 5' CCTTTGCTCCAATAT-GTG 3'; C-18, 5' TAGAGAATATTCGCTTGAG 3'; C-19,5' TAGTGCGAGCTCTGCCAGA 3'; C-20, 5' GAGATA-GAATTCACATTC 3'; C-21, 5' CTAAAAAGTATAGATC-CAGT 3'; C-22, 5' TAGTGCGAGCTCTGCCAGAAGT-TCC 3'; C-23, 5' AACTTCTGGCAGAGCTCGCAC 3'; C-24 5' CAATGGATTTTGGATAAAC 3'; C-25 5' CTC-TACTTTGGATGCCAA 3'; C-26, 5' GAGTTTGGTGT-TGTTTCA 3'; C-27 5' GCTCTATGCAGGTGGATT 3'; C-28, 5' GAAACTACAGGTGCTGAG 3'; C-29, 5' AGC-TATCATGAAAGGAGG 3'; C-30, 5' AGGATAGTGAAT-GACACA 3'; C-31, 5' ATAATCAGGGTTATTCTG 3'; C-41-1, 5' GCACCTTATTGAAGCTCT 3'; C-41-2, 5' GTTTGCCAACAACCTACA 3'; C-41-3, 5' GATAAAAC-CAGCGCACCT 3'; C-41-4, 5' CTGAAGATT-AGTTTGCCA 3'.

RT-PCR analysis of cyclin C gene expression.

Total RNA from chicken UG9 T-cells and DT40 B-cells is isolated by hot phenol extraction as described (Bunnell et al., supra). Poly(A)$^+$ RNAs corresponding to avian liver and brain are obtained from Clonetech. One microgram ($\mu$g) of RNA is analyzed from both cell lines and tissues by reverse transcriptase - polymerase chain reactions (RT-PCR) as previously described by others (Kinzler et al. 1991). Cyclin C-specific oligonucleotides are used to generate both the complementary DNA (cDNA) and the PCR products. The sequences of these oligonucleotides are as follows: CPP-1, 5' AGCGCACCTTATTGAAGCTCTT 3'; CPP-2, 5' AGGCAAGCTAGAGCTATCATGA 3'; CPP-3, 5' AGATC-TACTGAAGGAGCGCCAA 3'; CPP-4, 5' AGATT-AGTTTGCCAACAACCTACA 3'. The resulting RT-PCR products are run on 1% agarose-TBE gels and the fragments excised by electroblotting, as previously described (Kinzler et al., *Science* 253:661–665 (1991)). The isolated fragments are then purified and ligated into the TA vector (Invitrogen). The resulting clones are screened for inserts, the plasmids purified, and double-strand DNA sequence analysis performed as described above.

Cell cycle synchronization of DT40 cells. RNA and protein isolation, Northern blotting, immunoprecipitations, and Western blotting.

DT40 cells are synchronized by a two-step process. Because these B-cells are normally grown in suspension culture (Buerstedde et al., *Cell* 67:179–188 (1991)), their sensitivity to cell cycle drugs is somewhat limited. To overcome this problem a G1-phase enriched cell population is first elutriated by centrifugal elutriation. Elutriation conditions are as follows: Cells are grown in culture to a concentration of $0.5-1\times10^8$. These cells are then centrifuged gently and resuspended in 40–50 ml culture media containing 50% of the normal serum concentration. The elutriator (J6-M1 centrifuge) is prewashed with the same media (50% serum), and the centrifuge speed set to 2000 rpm. The pump is set at 8 ml/min. The cell suspension is then applied to the elutriator. The elutriator is washed by using the media containing 50% serum for 10 min. The pump is increased from 8 ml/min to 11 ml/min. Cells are collected to 100 ml. The collected cells are centrifuged and resuspended in regular culture media at a concentration of $0.5\times10^6$/ml. The elutriated cells are analyzed by fluorescence activated cell sorting (FACS) to confirm their position in the G1-phase of the cell cycle (Dolznig et al., *Cell Growth & Differ.* 6:1341–1352 (1995). Nocodazole (Sigma) is then added to a final concentration of 0.5 $\mu$g/ml to block the cells for 10–12 hrs. The synchrony of these cells blockage at metaphase is again confirmed by FACS analysis. The nocodazole-treated cells are washed twice with phosphate-buffered saline (PBS) to remove the drug and to release them from the chemical block. The cells are then added back to regular cell culture media and time points collected at 2 hr intervals. RNA is extracted from cells collected at these defined 2 hr intervals following their release from nocodazole, as described previously (Dolznig et al. 1995). Northern blot analysis of this total RNA is performed following transfer to a Duralose membrane with a PCR probe generated from intron 4 through intron 4a, which contains exon 4a, but does not contain any other region of the normal cyclin C mRNA (See FIG. 2). The sequence of the oligonucleotides used for generating this exon 4a-specific probe is as follows: Primer 1 (intron 4 derived) 5'-GACTTGCTGGCTGCCTCATA-3', Primer 2 (intron 4a derived) 5'-ATATATGAAAGGTATTACAGCCACAA-3'. This probe is labeled with [$^{32}$P]-dCTP (NEN), the blot hybridized, washed and visualized as previously described (Lahti et al. (1991); Li et al., *Gene* 153: 237–242 (1995). The same blot is hybridized with a chicken cyclin B2 cDNA as a positive control (Gallant et al., supra) and a $\beta$-actin cDNA probe as a control to demonstrate equal loading of RNA. This gel is also stained with ethidium bromide for the same purposes. A polyclonal antisera made to the *Drosophila melanogaster* cyclin C protein (Leclerc et al., supra) is used for the immunoprecipitation and Western blotting experiments. This antibody is affinity-purified by using a gel-purified full-length form of cyclin C. The previously reported protocols for both immunoprecipitation and Western blotting using this cyclin C antibody are followed (Leclerc et al., supra).

RESULTS

Avian cyclin C cDNAs and their predicted open reading frames.

Figure 1C:
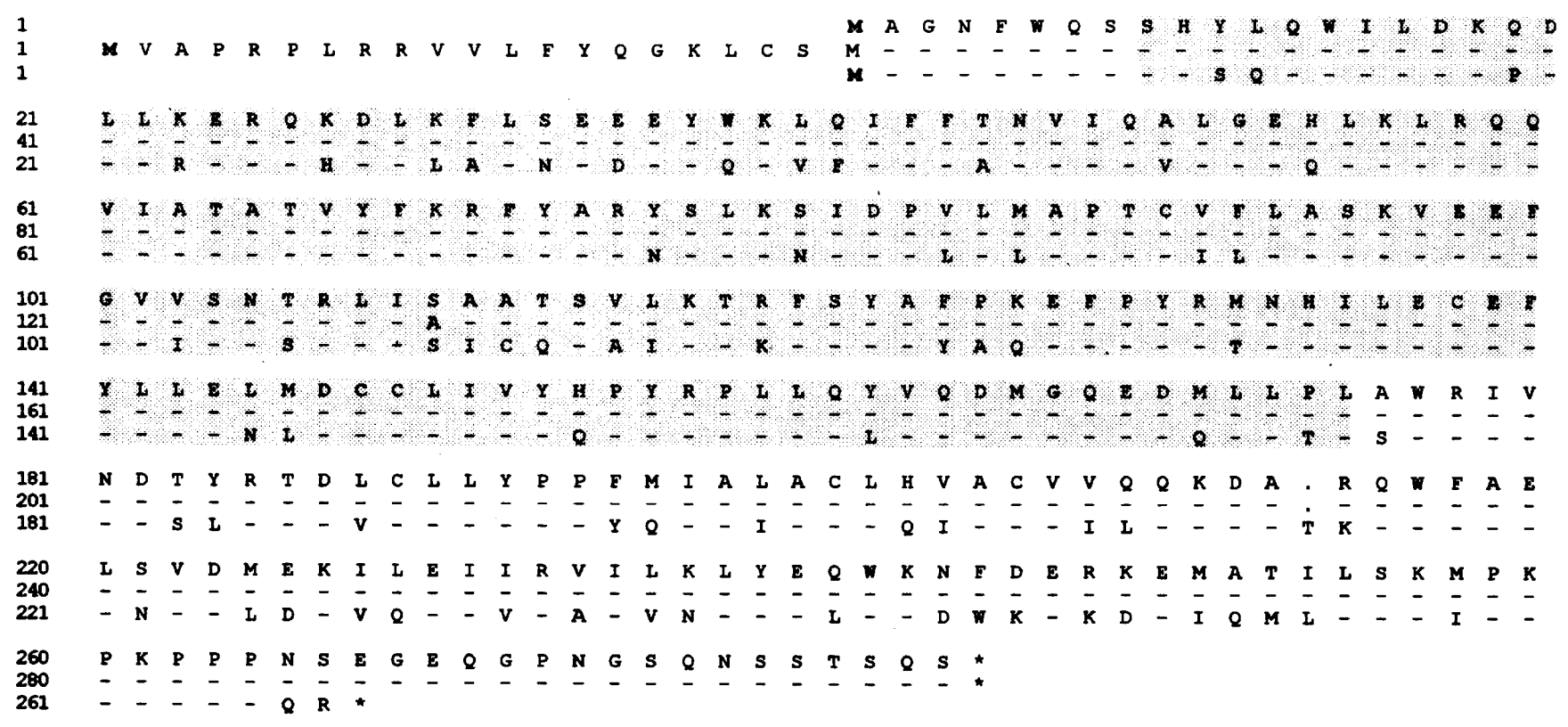

Screening of the chicken UG9 T-cell cDNA library yielded >20 positive cDNA clones. Restriction analysis of miniprep DNA from these lambda phage clones indicates that they contain inserts ranging in size from 1.8 to ~2.2 kb (data not shown). The inserts from these phage are subsequently cloned into a pKS plasmid vector, and the corresponding nucleotide sequence determined. Two distinct classes of cDNA sequences emerge; one corresponding to the previously reported cyclin C sequences from Drosophila and human, and the other containing a 73 bp insertion between codons 98 and 99 of the predicted ORF from the normal cyclin C homologue (FIG. 1A and 1B, SEQ ID NO:2). This insertion results in the addition of seven unique amino acids to the first 98 of the cyclin C protein and the termination of the predicted protein due to a chain terminating codon immediately after residue 105 (SEQ ID NO:4, see FIG. 1B). An additional in-frame termination codon is found 42 bp downstream of the first. The alternative cDNA sequence then rejoins the predicted sequence of the normal cyclin C cDNA, but due to the 73 bp size of the insertion a frame-shift occurs in the remaining cyclin C coding region. The predicted ORF of the avian cyclin C cDNA produces a 283 amino acid protein (SEQ ID NO:3) and is virtually identical to the predicted ORF of the human protein, containing only one amino acid difference at amino acid residue 110 of chicken (130 of human); a serine residue instead of an alanine residue (FIG. 1C). In avians, both the cyclin C and cyclin C-related cDNAs predict ORFs that start at a methionine residue that is identical to that used in the Drosophila cyclin C mRNA (FIG. 1A and FIG. 1C).

Location of the 73 bp cyclin C cDNA insertion within the avian cyclin C gene.

The corresponding cyclin C gene is isolated by screening a chicken genomic cosmid library with the avian cDNA insert. Six positive cosmid clones are identified and analyzed further by restriction endonuclease mapping and DNA sequencing. The mosaic structure of the avian cyclin C gene is shown in FIG. 2. The location of introns that interrupt the coding sequence in the avian gene is identical to intron ositions within the human gene [FIGS. 1 and 2; (Li et al., *Genomics* 32:253–259 (1996a))]. Intron distances in the avian cyclin C gene are established by PCR. To determine whether the 73 bp insertion found in the cyclin C-related cDNA is a part of the normal gene, and its location, specific oligonucleotide primers are made corresponding to the 5' and 3' ends of this sequence. The 73 bp sequence found in the alternative cyclin C cDNA corresponds to an identical 73 bp sequence (exon 4a) located between exons 4 and 5 of the normal cyclin C gene, the same location predicted by the cyclin C-related cDNA sequence (FIGS. 1 and 2). This sequence is not contiguous with either exons 4 or 5 in the genomic clones, indicating that it is an alternatively spliced exon located within the normal avian cyclin C gene.

Identification of alternate cyclin C mRNAs.

Figure 3A:
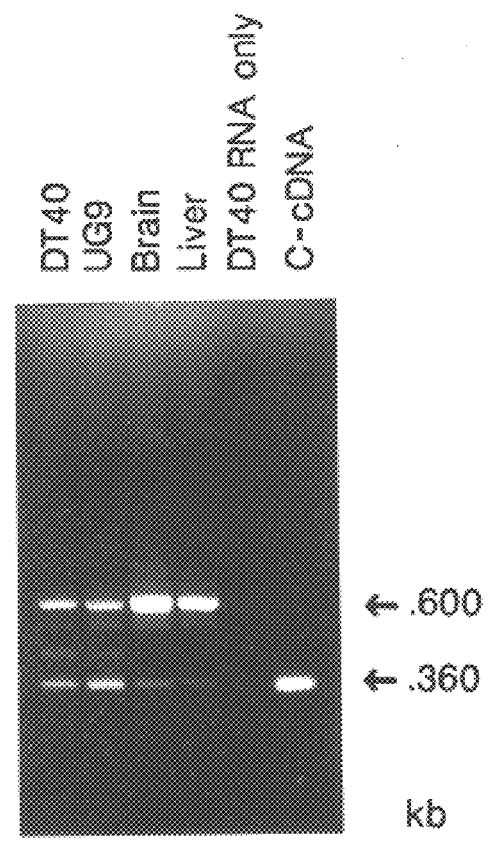
FIGS. 3A–3B depict RT-PCR analysis of the various cyclin C mRNAs (1, 2, and 3; as depicted in FIG. 2) from avian cell lines and tissues. The source of the cell line or tissue is indicated above each lane. Controls include DT40 cell RNA in the absence of PCR primers (RNA only) and the chicken cyclin C cDNA (C-cDNA) as a positive control. The sizes of the RT-PCR reaction products that were sequenced are shown to the left of each panel.

If the variant avian cyclin C cDNA arises from the insertion of an additional exon by alternative splicing, it would indicate that production of such an alternatively spliced cyclin C-related mRNA is an important mechanism for regulating cyclin C/cdk8 kinase activity in cells. To examine the expression of this cyclin C-related mRNA in various avian cell lines and tissues a specific RT-PCR primer set to amplify a region extending from the alternatively spliced exon (exon 4a) through exon 7 is designed (FIG. 2). This primer set should amplify a 360 bp region of cyclin C-related mRNA, while it would produce a >5 kb fragment from genomic DNA due to the introns located between these exons. The results of this experiment using UG9 and DT40 cell lines (which are both virally-transformed tumor cell lines), as well as normal liver and brain tissue poly($A^+$) RNA, demonstrates that all cell lines and tissues examined express the alternatively spliced 360 bp product (FIG. 3A). This product co-migrates with the positive control generated from the cyclin C-related cDNA and it is not found in negative controls. In addition, an unknown, but prominent, band of ~600 bp was observed as well (FIG. 3A). To determine the origin of this band, as well as verify the nature of the 360 bp product, the 360 bp and ~600 bp RT-PCR fragments are excised from gels and subcloned into the transactivator (TA) vector for DNA sequence analysis. This DNA sequence analysis verifies the identity of the 360 bp product as the alternatively spliced intron in all cell lines and tissues (data not shown). However, the larger 600 bp band contains the intronic sequence normally found between exons 4a and 5 in its entirety, but none of the intronic sequences found between the other exons included in this PCR product.

Figure 3B:
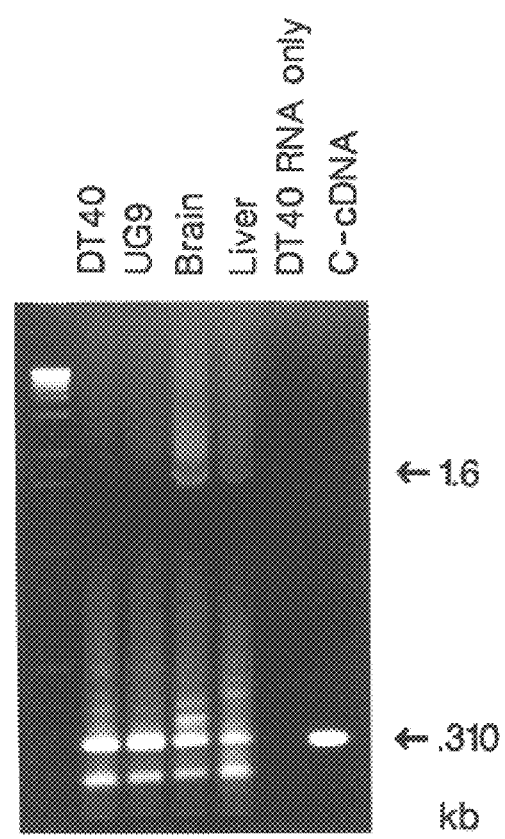

These results indicate that as many as three different cyclin C mRNAs might be present in these various cells (CmRNA-1, CmRNA-2, and CmRNA-3, FIG. 2). Only one of these transcripts, CmRNA-3,(having SEQ ID NO:1) would encode the entire cyclin C protein. To confirm this, a second set of oligonucleotide primers specific to the 5' end of exon 4a, or the adjacent intron found 5' of this exon, and extending to exon 2 is designed. If, indeed, the region between exons 4 and 5 is normally transcribed and produces two cyclin C-related mRNAs, two distinctly sized fragments of 310 bp and 1.6 kb should be observed. The size of the PCR product predicted from genomic DNA for the same region is >4 kb. As expected, the 310 bp and ~1.6 kb products are observed when RT-PCR reactions are performed with the various avian cell line and tissue RNAs (FIG. 3B). However, possibly the size and/or secondary structure of the larger RT-PCR fragment (~1.6 kb) limits the sensitivity of its detection. Once again, these bands are excised and cloned into the TA vector and their respective DNA sequences are determined. The smaller 310 bp fragment contains sequence from exons 2, 3, 4, and 4a, but no intronic sequences. Conversely, the larger 1.6 kb fragment contains these same exonic regions as well as the intronic sequence located between exons 4 and 4a. Attempts to detect additional introns of the cyclin C gene encoded in mRNAs by RT-PCR were unsuccessful, suggesting that this is a specific event involving only this region. These experiments confirm that in avians, cyclin C gene expression is complex and involves the production of multiple MRNA species, some of which may produce truncated cyclin C proteins.

Expression of the alternatively spliced cyclin C mRNA and its corresponding protein during the cell cycle.

To determine the biological significance of the expression of the alternatively spliced cyclin C mRNAs their expression is examined by Northern (FIG. 4) and Western (FIG. 5) blotting of RNA and protein, respectively. The RNA and protein used in these analyses are prepared from synchronized DT40 cells. Synchronous cell cycle progression of DT40 cells is achieved as described in Materials and Methods. RNA is then extracted from these cells and used for detection of the exon 4a containing cyclin C-related mRNA species with a PCR-generated probe. This probe includes only exon 4a and its immediately flanking introns, and therefore should not detect the normal, completely processed cyclin C mRNA. The nature of the probe used for detecting the alternatively spliced cyclin C mRNA is important, since the alternatively spliced cyclin C mRNA varies from the normal mRNA by only 73 bp, and both species are detected as a co-migrating band when analyzed by Northern blotting with the cyclin C cDNA (FIG. 4). Examination of the Northern blot probed with the exon 4a-specific probe reveals that the abundance of a major, alternatively spliced 1.7 kb cyclin C-related MRNA which varies markedly during the cell cycle, reaches maximal levels during G2/M and early G1 phase of the cell cycle (FIG. 4A). Conversely, expression of the mRNA encoding the normal cyclin C protein is invariant during the cell cycle (FIG. 4B). Additionally, levels of the truncated cyclin C mRNA (CmRNA-2) are comparable to the normal cyclin C mRNA only during G2/M phase, since the steady-state levels of the C mRNA-2 species diminish substantially during the remainder of the cell cycle. This pattern of RNA expression is similar to that observed for cyclin B2 on the same blot (FIG. 4C). Identical loading of RNA for each time point was demonstrated by EtBr staining (FIG. 4D) and β-actin hybridization. The alternatively spliced cyclin C mRNA (CmRNA-2) is found to be more abundant than any of the other RNA products detected by RT-PCR containing intronic sequences (CmRNA-1 and CmRNA-3), since the major mRNA transcript is ~1.7 kb in size. Thus, expression of the alternatively spliced cyclin C is cell cycle-specific and contributes to the function and/or regulation of the normal cyclin C/cdk8 complex during G2/M and early G1-phase. The cell cycle regulation of the CmRNA-2 species is definitely more dramatic than that observed for either avian or human cyclin C [FIG. 4B and (Lew et al., supra).

Figure 5A:
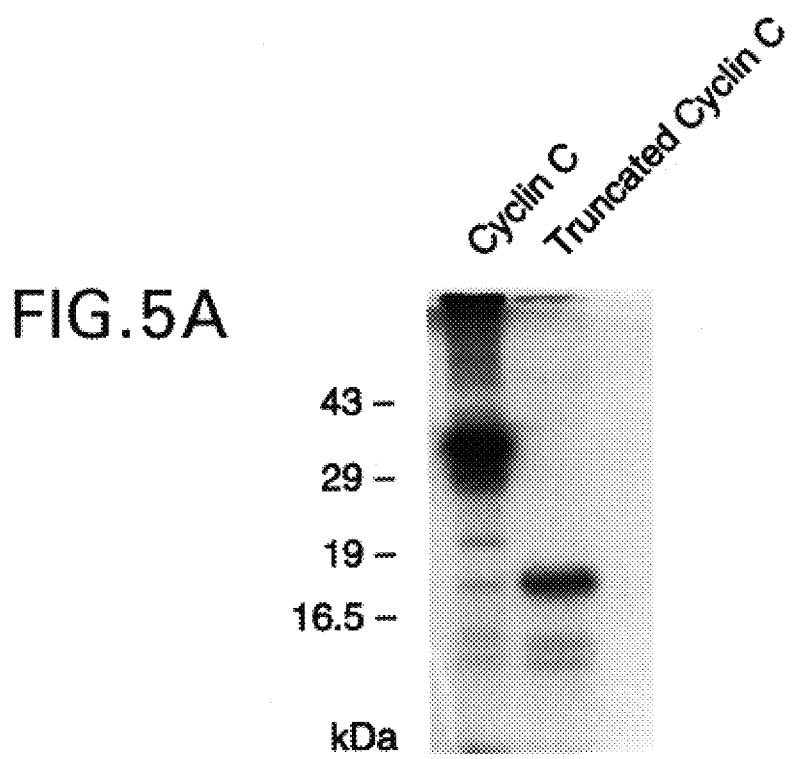
FIGS. 5A–5B depict expression of a smaller, 19 kDa cyclin C-related protein in avian cells.
Figure 5B:
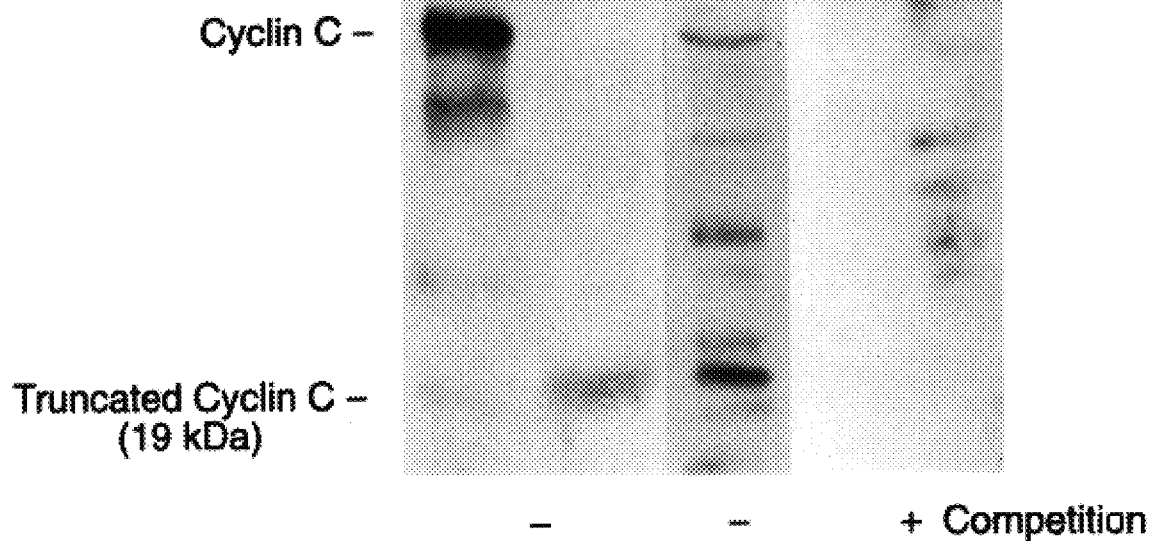

Western blot analysis of cyclin C proteins from synchronized DT40 B-cells reveals a relatively abundant ~19 kDa protein in G2/M-phase blocked cells (FIG. 5B). The cyclin C antibody used in these experiments is generated to the *D. melanogaster* cyclin C protein, which is highly related to both the human and avian homologues [FIG. 1 and (Leclerc et al., supra)]. This antibody recognized both the normal and truncated cyclin C IVTT (in vitro transcription translation (IVTT) products when used for immunoprecipitation of these proteins (FIG. 5A). A ~30 kDa cyclin C protein is detected in DT40 cell lysates from cells synchronized in G2/M-phase by nocodazole treatment (FIG. 5B). These cyclin C proteins co-migrate with the IVTT products corresponding to the normal and truncated avian cyclin C cDNAs, which are detected in this experiment by Western blot analysis using the affinity purified Drosophila cyclin C antibody (FIG. 5B). Specificity of the cyclin C antibody recognition of the 19 and 30 kDa cyclin C protein species is demonstrated by competition with an avian cyclin C-GST fusion protein (FIG. 5B). Detection of both the 30 kDa and the 19 kDa cyclin C proteins is dramatically inhibited by this preincubation, demonstrating the specificity of the cyclin C antibody interactions. In addition, this particular antibody has been extensively characterized in another study (Leclerc et al., supra). The 19 kDa cyclin C-related protein species is not detected in either asynchronous or late G1/early S-phase (G1/S phase), consistent with the reports of others (Leclerc et al., supra). Thus, it appears that the 19 kDa cyclin C-related protein corresponds to the CmRNA-2 species.

DISCUSSION

Expression of the cyclin C gene is complex. In avians, two mRNAs encoding truncated cyclin box proteins are produced in a cell cycle dependent fashion. In addition, a ~19 kDa protein is detected by cyclin C antisera during G2/M phase, and early G1-phase but not during late G1- or S-phase, in avian cell lines and normal tissues. The 19 kDa protein co-migrates with a similarly sized protein produced by in vitro transcription and translation (IVTT) of an alternatively spliced avian cyclin C-related mRNA. Expression of this alternatively spliced cyclin C mRNA is regulated during the cell cycle, peaking during G2/M phase. The recent discovery of a putative cyclin C cdk partner, cdk8, suggests that, like other G1 cyclins, the truncated cyclin C functions to regulate a specific Cdk, in a cell cycle dependent manner (Tassan et al., supra; Leclerc et al., supra). Cyclin C not only associates with cdk8 in vitro, leading to its activation, but they are also associated in vivo. Furthermore, the high degree of sequence identity between mammalian cyclin C and cdk8 with the *S. cerevisiae* SRB10 and SRB11 gene products, respectively, indicates that this complex might play an important role in the regulation of transcription. In yeast, the SRB10 and SRB11 gene products are associated in vivo with RNA polymerase II, and this cyclin/cdk complex is essential for integrating growth regulatory signals with gene transcription (O'Neill et al., supra; Liao et al., supra; Maldonado et aL, supra; Leclerc et al., supra).

One function of a truncated cyclin C protein would be analogous to endogenous CKIs, binding to and inactivating cdk8 during a portion of the cell cycle. Thus, much like the p16$^{INK4}$-related proteins, p21$^{Waf1/Cip1}$, p27$^{Kip1}$, and p57$^{Kip2}$, a truncated cyclin C protein could inactivate its associated protein kinase at specific times during the cell cycle (Sherr et al., (1995)). Such a truncated cyclin C protein would function as an endogenously encoded CKI that is regulated via splicing of the cognate gene. This is supported by the observed cell cycle dependent regulation of the expression of the truncated cyclin C MRNA and protein species. In fact, two of the three isolated cyclin C mRNA species (CmRNA-1 and CmRNA-2) from various avian cell lines and tissues encode this truncated product. By CmRNA-2 encoding a CKI-like protein, the appearance of abundant levels of this mRNA during G2/M and early G1-phase would also support a role for the active cyclin C/cdk8 protein kinase complex during late G1- and S-phase, coincidental with the transcription of genes by activated RNA polymerase II (Akoulitchev et al., *Nature* 377: 557–560 (1995); Leclerc et al., supra; Maldonado et al., supra). Others have shown alternatively spliced cyclin E transcripts in tumor cells, but these types of mRNA transcripts could not be found in normal cells, and they did not produce a corresponding protein in the tumor cell lines in which they were detected (Keyomarsi et al., *Oncogene* 15:2612–2624 (1995); Ohtsubo et al., *Mol. Cell. Biol.* 15:2612–2624 (1995)). In addition, an alternatively spliced cyclin D 1 MRNA transcript has been found, disrupting the normal ORF in the extreme carboxyl terminal region (Betticher et al., *Oncogene* 11:1005–1011 (1995)). Such alternatively spliced cyclin D1 mRNAs were found to be invariably expressed in a number of normal and tumor cell lines, but there was no demonstration of a specific protein associated with this altered transcript. In addition, these studies did not elucidate the possible role, if any, for such a transcript. One possible explanation put forth by the authors suggests that such changes in the carboxyl terminus of cyclin D1 may affect protein stability and/or antigenicity; however, the altered portion of the protein does not overlap the critical cyclin-box, or other regions that may be required for its function (Betticher et al., supra). Similarly, the alternatively spliced cyclin E mRNA's did not appear to encode a protein, and these transcripts were not expressed in normal cells.

Unlike the alternatively spliced cyclin D1 and cyclin E transcripts, the truncated cyclin C mRNA is specifically regulated during the cell cycle and it encodes a protein. Its widespread expression, in both virally transformed cell lines and normal tissues, suggests that its function is not tumor-specific.

Example 2

THE TRUNCATED CYCLIN C PROTEIN FUNCTIONS AS A CYCLIN DEPENDENT KINASE INHIBITOR

Introduction

The truncated cyclin box protein retains its ability to bind to the catalytic subunit through interactions between the cyclin box and cdk (Parry et al., *EMBO J.* 14:503–511 (1995)) and thereby competes for binding to cdk8 with the wild-type cyclin C protein during specific intervals of the cell cycle. The truncated cyclin C protein functions in such a manner as to resemble other CKIs, although it is the first example of the utilization of a portion of the same cyclin protein coding region as a CKI within either the cyclin or cdk gene families.

In vitro analysis of normal and truncated cyclin C protein function, and generation of antibodies.

To determine whether a truncated cyclin C protein is produced in vivo, antibodies generated to the first 98 amino acids of cyclin C are utilized. Two commercial polyclonal rabbit anti-human cyclin C antibodies corresponding to different aminoterminal peptides of the human protein have been reported (Upstate Biotechnology, Inc. and Pharmingen). At least one of these reagents (Upstate Biotechnology, Inc.) will immunoprecipitate the full-length and truncated avian cyclin C proteins generated by [$^{35}$S]-methionine labeled IVTT reactions using these cDNAs (FIG. 3). Western blots are performed using cell lysates (Xiang et al., supra) and are detected with using chemoluminescence with horseradish peroxidase-conjugated secondary antibodies (Leclerc et al., supra). Additional antibodies to either glutathione-S-transferase (GST) or 6-Histidine fusion proteins containing the aminoterminal domain, or the carboxyl terminal domain specific to the full-length form of cyclin C (which will not react with the truncated cyclin C protein), are generated by using the carboxyl-terminal region of cyclin C (amino acids 99–183) which are not found in the truncated cyclin C protein. Similarly, cdk8-specific antibodies are generated by use of GST or 6-Histidine fusion constructs. A human cdk8 cDNA has been obtained by RT-PCR and is analyzed by DNA sequence analysis. The avian homologue is isolated and analyzed in a similar manner (Parry et al., supra; Pelech et al., *TIBS* 17:233–238 (1992)). Rabbit polyclonal antibodies are generated and affinity purified as previously described (Parry et al., supra). Antisera's that specifically recognize the cdk8 and cyclin C proteins by both Western blotting and immunoprecipitation, using the IVTT cdk8, cyclin C, and truncated cyclin C polypeptides, are obtained and used to examine the expression and function of the truncated cyclin C protein in DT40 cells that are synchronously progressing through the cell cycle. This is an especially important point since cyclin C expression is not regulated during the cell cycle (Lew et al., supra) but the expression of the truncated cyclin C mRNA (CmRNA-2) is regulated during the cell cycle.

Both cyclin C and cdk8 antibodies are used to analyze cellular protein kinase activity as described by Tassan et al. (supra). DT40 cells are synchronized by either nocodazole or aphidicolin block of elutriated cell fractions, as described previously. The cyclin C antibodies are also used to detect similar truncated cyclin C protein made in either human or murine cell lines. Specific details of these experiments are provided below. These experiments conclusively demonstrate the existence of the truncated cyclin C protein and confirm that its expression parallels the cell cycle regulated expression of its corresponding mRNA.

The truncated cyclin C protein functions as an effective inhibitor of the normal cyclin C/cdk8 protein kinase complex in vitro in the Sf9 insect cell expression system. The infection and/or coinfection of insect Sf9 cells with baculovirus vectors encoding human and murine cell cycle gene products has elucidated specific functional interactions between a number of cell cycle proteins (Kato et al., *Genes & Devel.* 7:331–342 (1993); Lee et al., *Mol. Biol. Cell.* 3:73–84 (1992); Parker et al., *Proc. Natl. Acad. Sci., USA* 89:2917–2921 (1992); Parker et al., *Science* 55:1211–1214 (1995)). The Sf9 expression system successfully expressed many cell cycle related products, including cyclins A, B, D1, D2, D3 and E, and the cell cycle protein kinases cdk2, cdk4, cdk6, PCTAIRE 1 and PITSLREβ1. Expression of the full-length form of cyclin C and cdk8 in these cells creates an active cyclin/cdk protein kinase complex (Kato et al. (1993)). It is important to note that the avian cyclin C and truncated cyclin C proteins are highly homologous to the human cyclin C protein (99% identity for the former and at least 94% identity for the latter). Baculovirus expression constructs containing the truncated cyclin C protein and cdk8, as well as versions of each of the cyclin C proteins and the cdk8 kinase containing a small portion of hemagglutinin (HA) protein sequence attached to the carboxyl-terminus (e.g., HA-tagged cyclin C and truncated cyclin C constructs) are constructed by the methods used for other cyclines and cdks by Meloche et al. (*Mol. Biol. Cell.* 3:63–71 (1992)). The cyclin C and cdk8 proteins, the (His)$_6$- or HA-tagged proteins are affinity purified from nickel columns or from HA epitope affinity columns, respectively, as described by Meloche et al. (supra). Additional purifications, when needed, rely upon anion-exchange and gel filtration chromatography as described by Rosenblatt et al., *Proc. Natl. Acad. Sci. USA* 89:2824–2828 (1992). Column fractions can be assayed by SDS-PAGE and Western blotting with an appropriate antibody. Fractions of cyclin C or truncated cyclin C proteins are assayed for ability to phosphorylate histone H1 in the presence and absence of the cdk8 catalytic subunit. This is done by infection of Sf9 cells with each component separately (i.e., kinase or cyclin) and subsequently mixing equivalent amounts of protein from the lysates for a kinase assay, or by co-infection of Sf9 cells with multiple constructs (i.e., kinase and cyclin) and direct assay of a predetermined amount of cell lysate (Desai et al., *Mol. Biol. Cell,* 3:571–582 (1992).; Kato et al. (1993); Rosenblatt et al., supra). The ability to inhibit protein kinase activity assayed as described by others for previously identified CKIs can be demonstrated by adding the truncated cyclin C protein to active cyclin C/cdk 8 complexes (Guan et al., *Genes & Devel.* 8:2939–2952 (1994); Hirai et al., *Cell. Biol.* 15:2672–2681 (1995); Koh et al., *Nature* 375:506–510 (1995); Polyak et al., *Genes & Devel.* 8:9–22 (1994); Polyak et al, *Genes & Devel.* 8:9–22 (1994); Serrano et al., *Nature* 366:704–707 (1993)). Intrinsic cellular factors are provided in the reactions by mixing mammalian cell lysates, or specific immunoprecipitated proteins containing associated factors, with insect cell lysates containing the expressed kinase and/or cyclin and assaying for kinase activity, as described (Kato et al. (1993); Matsushime et al., supra). In other words, the purified cyclin and cdk produced by baculovirus infection of insect Sf9 cells are added back to total cell lysates. Thus, the baculovirus encoded cyclin or cdk can be readily purified using techniques that are well-established (Kato et al. (1993).

In vivo analysis of the function of the normal and truncated cyclin C proteins.

The analysis of the truncated cyclin C protein function is augmented by examining the function of this protein in eukaryotic expression systems and cell lines. The effect of regulated expression of the truncated cyclin C protein on the normal growth of several different mammalian cell types are studied by using the available chicken clone encoding the truncated cyclin C protein since it is identical in sequence to the human cyclin C protein for 98 of its 105 amino acid residues. Additionally, as described below, the cognate human homologue of the chicken mRNA is isolated. The human CDNA is used in both the in vitro studies described above and the in vivo studies outlined below. For stable expression of the cyclin C proteins in mammalian cells, the preferred approach is a tightly regulated, inducible expression system. These systems permit selection of stable integrants while keeping gene expression extinguished. Thus, even if expression of either cyclin C or its truncated form is deleterious to cell viability, stable cell lines are established.

A human T-cell line (Jurkat) and an epithelial cell line (HeLa) are obtained that express exogenous proteins under the control of a tetracycline-responsive promoter (Resnitzky et al., *Mol. Cell. Biol.* 14:1669–1679 (1994). The tetracycline-responsive promoter is created by fusing the tetracycline repressor with the activation domain of VP16 (a herpes simplex viral protein), thereby creating a tetracycline-controlled transactivator (tTA) that is constitutively expressed in cells. This tTA stimulates transcription of the gene of interest from a minimal promoter sequence containing tetracycline operator sequences, which are carried on a second plasmid. (This vector and its use in protein expression in human cells is described in detail by Gossen et al., *Proc. Natl. Acad. Sci., USA* 89:5547–5551 (1992)). Thus, expression of an exogenous gene is regulated by decreasing the concentration of tetracycline in the media. The tetracycline-responsive promoter expression system has been successfully used to regulate exogenously introduced G1-phase cyclins (D1 and E) in mammalian cells, as well as to regulate the developmentally controlled and tissue-specific genes in mice (Resnitzky et al., *Mol. Cell. Biol.,* 14:1669–1679 (1994); Gu et al., *Science* 265:103–106 (1994)). Alterations in the endogenous levels of either cyclin C or the truncated cyclin C protein result in significant changes in cell growth due to alterations of the cell cycle. Enhanced expression of either of these proteins, particularly the truncated protein, may also result in increased or decreased cell growth, or alternatively, programmed cell death. Changes in cell cycle progression and growth parameters are monitored by flow cytometry, growth curve analysis, and BudR incorporation, as described previously (Lahti et aL, *Mol. Cell. Biol.* 15: 1–11 (1995)). Concomitantly, the effect of sustained cyclin C or truncated cyclin C overexpression on RNA polymerase II CTD phosphorylation are examined as described previously (Akoulitchev et al., supra; Leclerc et al., supra; Maldonado et al., supra). To measure the extent of apoptosis, parameters of programmed cell death can be assayed, including the appearance of apoptotic nuclei, DNA fragmentation (as sensitively assayed by fluorescently labeled nick-translated DNA (Lahti et al. (1995)), and DNA ladder formation.

The existence of a novel mRNA transcript generated from the normal cyclin C locus which is widely expressed, cell cycle regulated, and encodes a truncated cyclin C protein suggests that its function may be linked to the normal protein kinase activity of the cyclin C/cdk8 complex. Furthermore, the avian truncated cyclin C protein interacts with CDK8. These experiments were performed by mixing lystates containing 35S-methionine labeled in vitro transcribed and translated cyclin C proteins (both the normal and truncated proteins were used in these studies) with rabbit reticulocyte lysates containing radioactive CDK8. After a one hour incubation at room temperature, antibodies to either cyclin C or CDK8 were added to the lysates. The immunoprecipitates were collected on protein A beads and analyzed by SDS-PAGE on 12.5% acrylimide gels. After electrophoresis the gels were dried and autoradiographed. Both CDK8 and the cyclin C proteins were present in the immunoprecipitates, demonstrating the interaction of both cyclin C and truncated cyclin C with CDK8.

Utilization of a single gene to differentially express multiple mRNA transcripts during distinct intervals of the cell cycle has not been associated with other cyclins. These observations indicate that the further examination of the expression and function of this truncated cyclin C protein, as well as the normal cyclin C protein, yields valuable information regarding cyclin C function and the function of the truncated cyclin C protein, as well as possible insights into the mechanism involved in the inactivation of cyclin/cdk complexes.

Example 3

CYCLIN C MRNAS AND PROTEINS IN MAMMALS

Introduction

The truncated cyclin C protein exists in humans and has a similar or identical function as the avian truncated cyclin C. In addition, a human cyclin C with an alternative carboxy terminal end is identified. Finally, the in vitro and in vivo systems established in this example can be used to functionally examine any genetic alterations identified in the CCNC locus in human tumors.

Both the predicted ORF of the cyclin C protein and the mosaic structure of the gene is absolutely conserved between human and chicken (Li et al. (1996a). Antibodies that recognize the aminoterminal region of cyclin C, and, as a result, the truncated cyclin C protein, allow identification of a similar truncated protein to be made in mammals. Several different human cell lines (including HeLa and W138 normal diploid fibroblasts) are synchronized with either drugs (such as nocodazole or aphidicolin), serum depletion, or centrifugal elutriation as described. Cell cycle synchrony is verified by flow cytometry analysis. Synchronized cells are used for these experiments since expression of the alternatively spliced avian transcript, and truncated protein, is cell cycle regulated. Total cell protein lysates are isolated from each fraction of cells and analyzed by Western blotting for the presence of a truncated cyclin C protein using the cyclin C amino-terminal antibody. Detection of the normal wild-type cyclin C protein provides an internal control for these experiments. As a complementary approach metabolically labeled synchronized cells are made by pulsing with [$^{35}$S]-methionine prior to immunoprecipitating the cyclin C proteins as described.

Several distinct, but complementary, approaches are taken to isolate a cDNA clone encoding this protein. The first, and most direct, approach involves the use of reverse transcriptase-polymerase chain reaction (RT-PCR). Total RNA and/or poly(A)+RNA from different human cell lines are converted to cDNA using cyclin C specific gene primers and then subjected to nested PCR (Li et al.; Li et al. (1996a)). cDNA are synthesized from primers originating from the 3' end of the mRNA (corresponding to exons 10–12) of the CCNC gene (which encodes cyclin C). Placement of the oligonucleotides for cDNA synthesis at this position allows identification of an alternatively spliced transcript in human cells, since the alternatively spliced avian mRNA contains an insertion of an exon between exons 4 and 5 of the gene. Due to the identity of the human and avian genes (Li et al. (1996a, b), oligonucleotides for the nested PCR reactions within exons 3/4 and 5/6 are generated. The highly conserved nature of both the genes and their polypeptides, indicates that exon 4a is similar in size (73 bp) in humans. In the event this exon is not as highly conserved in humans, the placement of the oligonucleotides for the nested PCR reactions within exons 4 and 5 (inversely orientated to generate an appropriate PCR product) ensures its isolation. Alternatively, cDNA libraries generated from RNA isolated from G2/M and early G1-phase synchronized cells are screened with the human cyclin C cDNA (Lew et al., supra; Li et al. (1996a). The inserts from any resulting positive clones are analyzed by DNA sequence analysis using oligonucleotide sequencing primers located in exons 4 and 5 which are oriented towards one another. Such primers currently exist, and are used in the analysis of the human CCNC gene (Li et al. (1996a). Oligonucleotides from other regions of the gene and restriction enzyme analysis using enzymes that cut frequently are also used to identify the genomic exon encoding an alternatively produced transcript from a different location within the human gene.

Human cyclin C variant transcripts were isolated by screening a human testis cDNA library with a human cyclin C cDNA probe containing the entire coding sequence for the human cyclin C protein. In addition to the normal cyclin C cDNA, two other classes of cDNA clones have been isolated. One of these represents an alternatively spliced human mRNA. This transcript is generated by the insertion of additional coding sequence between sequences derived from exons 11 and 12 in the human cyclin C cDNA (FIG. 7). The protein encoded by this MRNA has an alternative carboxy-terminal end (FIG. 6). This substitution changes the stability of the protein since the alternatively spliced transcript no longer encodes a protein with a PEST sequence rich carboxyl-terminal domain. (PEST sequences have been shown to be involved in the rapid turnover of many proteins including other GI cyclins).

A second class of cDNA clones represents a partially spliced mRNA. All of the intronic sequences have been removed from these transcripts with the exception of the introns located between exon 7 and 9 (exon 8 is included) (FIG. 9). Extensive analysis of other cDNA clones has revealed that this is the only partially spliced cyclin C transcript found in the cells, indicating it has biological significance. This transcript is predicted to encode a truncated cyclin C protein (FIG. 8), similar in nature although slightly larger than that found in avians.

Example 4

ELIMINATION OF FULL-LENGTH AND/OR TRUNCATED CCNC PRODUCTS

The linking of cyclin C to cell cycle specific regulation of RNA polymerase II indicates that the extracellular growth signals and nuclear transcription complexes are coordinated, at least in part, to the action of the cyclin C/cdk 8 protein kinase complex. Such a link could be integral for normal cell growth, and any alteration of this pathway could prove to have devastating consequences. A strong correlation between deletion of the human cyclin C (CCNC) gene and deletion and/or translocation of the 6q21 chromosome region in human acute lymphoblastic leukemia (ALL) has also been established (Li et al. (1996a). However, the complete loss and/or functional alteration of both CCNC gene alleles has not been observed. This could be explained by the essential function of this gene product. The existence of the widely expressed and cell cycle regulated alternatively spliced transcript, encoding a truncated cyclin C protein of the present invention, suggests that the CCNC gene is normally regulated in a complex manner. More importantly, this truncated cyclin C protein may, in fact, directly inhibit normal cyclin C protein function by competing for binding to the cdk8 subunit during specific intervals of the cell cycle. Elucidation of the requirements for both normal cyclin C and the truncated cyclin C protein in vertebrate cells provides valuable insights regarding their normal function as well as their possible involvement in tumorigenesis. This can be accomplished by specific ablation of either the normal or truncated cyclin C protein via targeted disruption of the gene. In addition, further analysis of the truncated cyclin C protein in human tumor cells, with emphasis on determining its integrity within these cells, is warranted, particularly since the truncated protein functions as a CKI of the normal cyclin C/cdk8 complex. The studies described herein address questions regarding the requirements, and function, of both the normal and truncated cyclin C proteins. Experiments are performed to investigate the role of the truncated cyclin C protein regarding tumor suppression in malignancies with deletions of one CCNC gene allele, as well as to determine the extent that alterations in the level of either cyclin C or the truncated cyclin C proteins affect parameters of cell growth. Genetic alterations identified in the CCNC gene locus in human tumors as a result of these studies are then functionally examined as outlined above.

Another approach for examining the functional relationship between the normal cyclin C, or the truncated cyclin C and the in vivo protein kinase catalytic subunit, cdk8, involves gene targeting in cultured vertebrate cells. Elimination of the various CCNC gene products specifically, or in combination, allow the assessment of their normal function in a manner that is distinct, but complementary, to the in vitro reconstitution and tightly regulated overexpression studies described above.

Targeted disruption of the CCNC gene regions encoding cyclin C and/or the truncated cyclin C protein in avian cells.

Further evidence that the truncated cyclin C protein functions as an inhibitor of normal cyclin C/cdk 8 complexes is derived from studies where truncated cyclin C is specifically eliminated from vertebrate cells. Concomitantly, the effect of cyclin C deficiency or elimination is examined. Targeted disruption of a specific gene via homologous recombination has become a very powerful tool in molecular genetics (Capecchi et al., Science 244:1288–1292 (1989); Doetschman et al., Proc. Natl. Acad. Sci., USA 85:8583–8587)). Mouse models of disease can now be produced. The approximate ratio of specifically targeted gene disruption events to random integration events after transfection of DNA constructs into mammalian cells is 1:102 to 1:105 (Serrano et al. (1993)). A chicken B cell line, DT40, incorporates foreign DNA by specific targeted integration at frequencies that are similar to those seen for random integration (Buerstedde et al., supra). This was not a gene-specific event, since targeted integration occurred at identically elevated frequencies at four different genetic loci (Buerstedde et al., supra)). Therefore, the chicken DT40 cell line provides a valuable system for the ready isolation of mutant cells that is technically less difficult and less time consuming than the murine model. To perform these studies the chicken homologue of the particular gene of interest needs to be isolated and characterized. The chicken cyclin C cDNA, truncated cyclin C cDNA, and their cognate gene have been isolated and are part of the present invention, as are polyclonal antisera that recognize both the normal and truncated cyclin C proteins by immunoprecipitation. The chicken cell system described here provides a practical advantage to murine systems due to the ease of generation and decreased complexity of DT40 cell culture. In addition, this cell system has already been used to eliminate both alleles of cyclin D1 and it has been demonstrated that the corresponding alteration in cell cycle progression can be evaluated. This system can be used to disrupt both products of the avian CCNC gene (the normal cyclin C mRNA and the alternatively spliced mRNA encoding a truncated cyclin C protein), individually and in tandem, in the DT40 cell line to determine whether cell growth parameters and/or programmed cell death (PCD) are affected.

Complete characterization of the avian CCNC gene indicates that the positions of all intron/exon positions are absolutely conserved. Specific disruption of the alternatively spliced cyclin C transcript is achieved by disruption of exon 4a, which encodes the alternatively spliced region of this cell cycle regulated transcript. Simultaneous disruption of both cyclin C and the alternatively spliced cyclin C is achieved by disrupting either exon 1, 2, 3, or 4, which are shared between the two transcripts and encode essential portions of their open reading frames. Specific disruption of cyclin C can be achieved by targeting any region of exons 5–11, which contain essential portions of the cyclin C open reading frame (ORF), but are not required for expression of the truncated cyclin C protein. Targeted disruption of the gene can involve the insertion of neomycin (neo), hygromycin (hyg), (puromycin), or (histidino) (his) selectable marker gene cassettes into unique exonic restriction sites. These genes are derived from bacteria that are resistant to the corresponding drug. Since these antibiotic resistance genes are encoded by the expression vector containing the cyclin sequences, and are not naturally found in eucaryotic cells, those cells that survive drug treatment will contain an expression vector that also contains the cyclin gene. The availability of at least four distinct selectable markers allow the generation of multiple disruption plasmids.

Two disruption plasmids containing either a neo or hyg cassette are prepared which target both full-length and truncated cyclin C proteins. To create these constructs a ~1 kb EagI-KpnI restriction fragment containing exons 1–2 is removed and replaced with the selection cassettes, resulting in the disruption of a major portion of the cyclin box domain. Additional constructs are made that can target exon 4a specifically, by deletion of this exon and its immediately adjacent intronic regions using restriction enzymes that remove only this region from a large 7 kb EcoRI fragment containing exons 3–7. Finally, disruption of only the cyclin C protein, but not the truncated cyclin C protein corresponding to the ORF encoded by exons 1–4a, can be achieved by similar deletion of a region of the avian CCNC gene containing exon 7 by using two EcoRI fragments (~2 kb), containing exons 7–9, from a larger 13 kb BamHI-SacI fragment which contains exons 4–12 of the gene (FIG. 2). These selectable marker gene cassettes have been used to disrupt the avian CCND1 gene, and are used to replace this region and disrupt the normal cyclin C protein. As performed previously for the avian CCND1 gene, targeted disruption of the CCNC gene and its encoded products are verified by Southern and Northern blotting, and by either immunoprecipitation and/or Western blotting of the protein. Single cell clones can be selected by FACS sorting, as previously performed for the avian CCND1 gene disruptions, after continuous culture in selection drug for a period of 2–3 weeks (Reznitzky et al. (1994)).

The effect of ablation/haploinsufficiency of cyclin C and/or the truncated cyclin C box protein on cell growth, programmed cell death, and tumorigenesis.

In the event that elimination of both CCNC alleles encoding the cyclin C protein is lethal, isolation of resistant colonies containing the second selectable marker gene following disruption, appropriate selection, and analysis of the first homologous recombination event may not be possible. In this case the result can be verified by switching the order of selectable marker genes used to disrupt these genes, insuring that this result is not due to technical problems or selection protocols, as performed with the CCND1 gene knockouts. Verification of lethality due to CCNC gene disruption would suggest that their function is essential, and these experiments can then be terminated. However, the single allele knockout clones can be analyzed for changes in cell growth, cell death, and tumorigenicity. In the case that disruption of both CCNC genes is not lethal, further experiments with these cell lines can be conducted as described below. Once clonal cell lines are obtained with one and/or both CCNC genes disrupted, cyclin C protein expression can be verified to be diminished/ablated by immunoprecipitation with the cyclin C-specific antibodies of the present invention, using appropriately metabolically labeled cell lysates and/or Western blot analysis. The ability of parental DT40, CCNC−/+, and CCNC−/− to progress normally through the cell cycle after synchronization, or undergo apoptosis in response to glucocorticoids and anti-IgM antibodies can be assessed. Cell cycle studies can be performed as described for the CCND1 gene disruptions. The effect of diminished cyclin C protein expression on the ability of the cells to progress through the cell cycle, as measured by BudR incorporation and mitotic indices, using both asynchronous and synchronously blocked cell populations can be examined. Further, more detailed, analyses of specific cyclin/cdk complexes can be performed. The regulation of programmed cell death can be assayed as described previously (Lahti et al. (1995)). DT40 cells are an early B-cell lineage that express surface IgM and can undergo programmed cell death by sIgM cross-linking anti-chicken sIgM antibodies (Ezhevsky et al., *Mol. Biol. Cell* 7:553–564 (1996)). In the case that substantial changes in either cell cycle progression or the ability of these cell lines to undergo programmed cell death, several different CCNC −/− clonal cell lines can be compared to one another to eliminate any effects of clonal variation.

Further, more detailed analysis of the effect of diminished, or abolished (if not lethal), levels of cyclin C on cdk8 protein kinase activity as a function of the cell cycle, and with regard to the ability of the C-terminal domain (CTD) of RNA polymerase II to be phosphorylated, can also be examined. RNA polymerase II protein and antibody are available commercially, and can obtained for these studies (RNA polymerase II is a well conserved protein (Akoulitchev et al., supra; Osslpow et al., *Cell* 83:137–146 (1995)). Generation of appropriate antibodies against avian RNA polymerase II, as described previously for both cyclin C and cdk8 can also be undertaken. Immunoprecipitations and kinase assays can be performed as has been done for other cell cycle proteins. This type of analysis allows the determination of whether elimination of cyclin C leads to complete, or partial loss of cdk8 kinase activity; ultimately, these investigations can provide important information regarding the possibility of redundant cyclin, or cyclin-like, regulatory partners for this catalytic subunit in vertebrate cells, as well as its possible relationship with the cdk activating protein kinase (CAK; cdk7) (Desai et al. (1992); Solomon et al. (1993), reviewed in Morgan (1995).

Analogous experimental procedures for the selection, cloning, and examination of cell cycle progression and programmed cell death parameters can be performed on targeted disruptions of the truncated cyclin C protein, as well as the simultaneous elimination of both the cyclin C and truncated cyclin C proteins, as has been described above. In the case where significant differences in the parameters of cell growth and/or death are observed the rescue of the phenotype by re-expressing the protein that has been eliminated can be performed. A similar strategy was applied to the CCND1 gene knockouts, which successfully rescued these cells (Li et al. (1 996a)).

Deletion of one CCNC gene in tumor cells.

Previous studies of the deletion of the CCNC gene in human ALL may need to be re-examined (Li et al., supra). In those studies one CCNC allele was found to be deleted in 12/16 ALL patient samples with 6q21 anomalies (deletions and/or translocations), but the remaining allele harbored no apparent mutations within the 12 exons examined. At that time the alternatively transcribed mRNA product of the present invention was not known. Loss of both copies of the normal cyclin C protein could have devastating consequences on cell growth, particularly in light of the accumulating evidence regarding its involvement in the cell cycle regulation of RNA polymerase II (Akoulitchev et al., supra; Leclerc et al. (1996); Maldonado et al. (1996)). However, since human cells also express this truncated cyclin protein by alternatively splicing of an additional exon, this exon could harbor specific mutations that inactivate its ability to negatively regulate the cyclin C/cdk 8 complex, much like p16$^{INK4}$a deletion and mutation in human tumors (Cairns et al.; Caldas et al. *Nature Gen.* 8:27–32 (1994); He et al., *Cancer Res.* 54:5804–5807 (1994); He et al., *Cancer Res.* 55:4833–4836 (1995); Hussussian et al., *Nature Gen.* 8:15–21 (1994); Kamb et al., *Science* 264:436–440 (1994); Kamb et al. *Nature Gen.* 8:22–26 (1994); Koh et al., supra; Liu et al., *Oncogene* 10:1061–1067 (1995); Lukas et al., *Cancer Res.* 55:4818–4823 (1995); Lukas et al., *Nature*, 375:503–506 (1995); Medema et al., *Proc. Natl. Acad. Sci., USA,* 92:6289–6293 (1995); Parry et al., *EMBO J.,* 14:503–511 (1995). Since studies indicate that this truncated cyclin C protein functions as a CKI and that it is present in human cells, careful evaluation of the integrity of this exon in the previously analyzed ALL patient samples is required. The extensive bank of frozen tumor samples of St. Jude Children's Research Hospital and corresponding database allows for potential correlations to be made between mutations in the CCNC gene, tumor progression, and/or therapeutic responsiveness.

Mutation of the exon encoding the premature stop codon, leading to truncated cyclin C protein expression, in ALL patient samples with previously identified CCNC gene deletions As mentioned above, demonstration of the existence of an alternatively spliced cyclin C transcript encoding a truncated protein in human cells warrants further examination of the ALL patient samples. A single strand conformational polymorphism (SSCP) analysis of this exonic region and its immediately flanking intronic sequences, can be performed as has been performed by for remainder of the human CCNC gene (Li et al. (1996a)). PCR-based SSCP analysis has proved to be a reliable method for the rapid detection of point mutations, small deletions or insertions, and polymorphisms in short fragments of DNA that can be amplified by PCR. Specific oligonucleotides corresponding to the flanking intronic sequences immediately adjacent to this exon can be designed and used in these studies (Li et al., (1996a). The presence of point mutations or other alterations in the alternatively spliced exon can be confirmed by cloning and sequencing of this region of the CCNC gene by genomic PCR.

In the case when specific point mutations, deletions, and/or insertions are discovered in this region of the CCNC gene, their effect on the normal function of this gene can be evaluated. For example, if specific point mutations that interfere with the ability of the protein to be normally terminated are found, they can be programmed back into Sf9 insect cell expression system as described herein. Such mutations could lead to the expression of longer, non-specific protein regions at the carboxyl terminus. This would allow the examination of the ability, or inability, of such elongated proteins to bind to the cdk8 catalytic subunit and affect its activity. Similarly, mutations that might alter the ability of this exon to be normally spliced into an mRNA transcript, such as mutations within the canonical splice donor and acceptor sequences, can be examined by transient transfection analysis of appropriate plasmid expression constructs in human cells.

CCNC gene deletion resulting in haploinsufficiency of either the full-length and/or truncated form of the cyclin C protein.

It is possible that deletion of a single allele directly affects the level of cyclin C protein. One approach is to analyze these samples using quantitative competitive RT-PCR, and Western blot analysis of cell lysates. Quantitative competitive RT-PCR allows relatively precise quantitation of specific mRNAs (Gilliland et al., *PCR Protocols,* San Diego, Calif.: Academic Press, 60–69 (1990)). The procedure involves the co-amplification of a competitive template that uses the same oligonucleotide primers as those of the target cDNA, but this competitive template can be distinguished from the target cDNA after amplification. The tumor samples are examined using 3-glycerol aldehyde phosphate dehydrogenase (3-GAPH) as a positive control and p16$^{INK4a}$ as a negative control. The use of the latter as a negative control is based on previous analysis of these same ALL patient samples, many of which contain concomitant loss of one or both alleles of human chromosome 9p21 and the p16$^{INK4a}$ and/or p$_{15}$$^{INK4b}$ genes (Okuda et al., *Genomics* 29:623–630 (1995)). A potential problem of this approach stems from the fact that primary tumors are contaminated with a variable percentage of normal cells. However, the use of hematopoietic tumors can circumvent this problem, particularly when combined with morphologic examination (% blast cell determinations), direct fluorescence in situ hybridization (FISH) analysis (for CCNC deletions), and cytogenetic analysis which are well known in the art (Lahti et al., (1994)). These types of analyses can be coordinately used to identify cases with a low percentage of contaminating normal cells and to pinpoint those that have substantial deletions of the CCNC locus. When noticeable differences are detected in normal or truncated cyclin C mRNA and/or protein expression, the effect of such alterations on normal cell growth parameters can be assessed using the complementary studies involving targeted disruption of the CCNC gene as described above.

The following is a list of documents related to the above disclosure and particularly to the experimental procedures and discussions. These documents, and all others cited above, should be considered as incorporated by reference in their entirety.

Adames et al., Nature 318:533–538 (1984).

Akoulitchev, S., Makela, T. P., Weinberg, R. A., and Reinberg, D., Nature, 377: 557–560 (1995).

Alexander et al., Mol. Cell. Biol. 7:1436–1444 (1984).

Bar et al., J. Magn. Reson. 65:355–360 (1985).

Benoist et al., Nature 290:304–3 10 (198 1).

Betticher, D. C., Thatcher, N., Altermatt, H. J., Hoban, P., Ryder, W. D. J., and Heighway, J., Oncogene 11:1005 –1011 (1995).

R. A. Brady et al., Phil. Trans. R. Soc. Land. B 316:143–160 (1987).

Brinster et al. Nature, 296:39–42 (1986).

Buerstedde, J. M. and Takeda, S., Cell 67:179–188 (1991).

Bunnell, B. A., Heath, L. S., Adams, D. E., Lahti, J. M., and Kidd, V. J., Proc. Natl. Acad. Sci., USA 87:7467–7471 (1990).

Cairns, P., Polascik, T. J., Eby, Y., Tokino, K., Califano, J., Merlo, A., Mao, L., Herath, J., Jenkins, R., Westra, W., Rutter, J. L., Buckler, A., Gabrielson, E., Tockman, M., Cho, K. R., Hedrick, L., Bova, G. S., Isaacs, W., Koch, W., Schwab, D., and D. Sidransky, Nature Gen., 11:210–213 (1995).

Caldas., S. A. Hahn, L. T. daCosta, M. S. Redston, M. Schutte, A. B. Seymour, C. L. Weinstein, R. H. Hruban, C. J. Yeo, and S. E. Kern, Frequent somatic mutations and homozygous deletions of the p16 (MTS1) gene in pancreatic adenocarcinoma, Nature Gen. 8:27–32 (1994).

Capecchi, M. R., Science, 244:1288–1292.

Carpino et al., J. Org. Chem. 37:3403–3409 (1972).

Chou et al., Biochemistry 13:222 (1974).

Cross, F. R., Mol. Cell Biol. 10:6482–6490 (1990).

Darnell et al. (1986) in Molecular Cell Biology, pp. 146–148, Scientific American Books, New York.)

DeBoer et al., Proc. Natl. Acad. Sci., USA 80:21–25 (1983).

Demetrick, D. J., S. Matsumoto, G. J. Hannon, K. Okamoto, Y. Xiong, H. Zhang, and D. H. Beach, Cytogenet. Cell Genet. 69:190–192 (1995).

Desai, D., Gu, Y., and D. O. Morgan, Mol. Biol. Cell, 3:571–582 (1992).

Doetschman, T., Maeda, N., and O. Smithies, Proc. Natl. Acad. Sci., USA, 85:8583–8587 (1988).

Dolznig, H., Bartunek, P., Nasmyth, K., Mullner, E. W., and Beug, H., Cell Growth & Differ. 6:1341–1352 (1995).

Eipers, P. G., Lahti, J. M., and Kidd, V. J., Genomics 13:613–621 (1992).

Engstom, Biochem. Exp. Biol. 11:7–13 (1974).

Ezhevsky, S. A., Toyoshim, H., Hunter, T., and D. W. Scott, Mol. Biol. Cell., 7:553–564 (1996).

Fields et al., Int. J. Pept. Protein Res. 35:161–214 (1990).

Gallant, P. and Nigg, E. A., J. Cell Biol. 117:213–224 (1992).

Gold, R., Schmied, M., Rothe, G., Zischler, H., Breitschopf, H., Wekerle, H., and H. Lassman, Histochem. & Cytochem., 41:1023–1030 (1993).

Gossen, M., and H. Bujard, Proc. Natl. Acad. Sci., USA, 89:5547–5551 (1992).

Grosschedl et al. Cell, 38:647–658 (1984).

Gu, H., Marth, J. D., Orban, P. C., Mossman, H., and K. Rajewsky, Science, 265:103–106 (1994).

Guan, K.-L, Jenkins, W., Li, Y., Nichols, M. A., Wu, X., O'Keefe, C. L., Matera, A. G., and Y. Xiong, Genes & Devel., 8:2939–2952 (1994).

Hammer et al. Science 235:53–58 (1987).

Hanahan, Nature 315:115–122 (1985).

He, J., Allen, J. R., Collins, P., Allalunis-Turner, M. J., Godbout, R., Day, R. S., and C. D. James, Cancer Res., 54:5804–5807 (1994).

He, J., Olson, J. J., and James, C. D., Cancer Res., 55:4833–4836 (1995).

Hirai, H., Roussel, M. F., Kato, J-Y., Ashmun, R. A., and C. J. Sherr, Cell. Biol., 15:2672–2681 (1995).

Hopp et al., Proc. Natl. Acad. Sci., USA 78:3824 (1981).

Hussussian, C. J., Struewing, J. P., Goldstein, A. M., Higgins, P. A. T., Ally, D. S., Sheahan, M. D., Clark, W. H., Tucker, M. A., and N. C. Dracopoli, Nature Gen., 8:15–21 (1994).

Hutchinson, et al., J. Biol. Chem. 253:6551 (1978).

Hutchinson et al., Proc. Natl. Acad Sci., USA 83:710 (1986).

Kamb, A., Gruis, N.-A., Weaver-Feldhaus, J., Liu, Q., harshman, K., Tavtiglan, S.-V., Stockert, E., Day III, R.-S., Johnson, B.-E, and Skolnick, M.-H, Science, 264:436–440 (1994).

Kamb, A., Shattuck,-Eidens, D., Eeles, R., Liu, Q., Gruis, N. A., Ding, W., Hussey, C., Tran, T., Miki, Y., Weaver-Feldhaus, J., McClure, M., Aitken, J. F., Anderson, D. E., Bergman, W., Frants, R., Goldgar, D. E., Green, A., MacLennan, R., Martin, N. G., Meyer, L. J., Youl, P., Zone, J. J., Skolnick, M. H., and L. A. Cannon-Albright, Nature Gen., 8:22–26 (1994).

Kato etal., Genes & Devel., 7:331–342 (1993).

Kato, J-Y., M. Matsuoka, D. K. Strom, and C. J. Sherr, Mol. Cell. Biol., 14:2713–2721 (1994).

Kelsey et al., Genes and Devel., 1:161–171 (1987).

Keyomarsi, K., Conte, Jr.D., Toyofuku, W., and Fox, M. P., Oncogene 15: 2612–2624 (1995).

Kidd, V. J., Luo, W., Xiang, J., Tu, F., Easton, J., McCune, S., and Snead, M. L., Cell Growth & Differ. 2:85–93 (1991).

Kimura et al., Proc. Natl. Acad Sci., USA 77:1681–1685 (1980).

Kinzler, K. W., Nilbert, M. C., Su, L-K., Vogelstein, B., Bryan, T. M., Levy, D. B., Smith, K. J., Preisinger, A. C., Hedge, P., McKechnie, D., Finniear, R., Markham, A., Groffen, J., Boguski, M. S., Altschul, S. F., Horii, A., Ando, H., Miyoshi, Y., Miki, Y., Nishisho, I., and Nakamura, Y., Science 253:661–665 (1991).

Koh, J., Enders, G. H., Dynlacht, D., and E. Harlow, Nature, 375:506–510 (1995).

Kollias et al., Cell 46:89–94 (1986).

Kowalczyk, J. R., Grossi, M., and Sandberg, A. A., Cancer Genetics and Cytogenet. 15:47–60 (1985).

Krumlauf et al., Mol. Cell. Biol. 5:1639–1648 (1985).

Lahti, J. M., Chen, C.-l. H., Tjoelker, L. W., Pickel, J. M., Schat, K. A., Calnek, B. W., Thompson, C. B., and Cooper, M. D., Proc. Natl. Acad. Sci., USA 88:10595–10960 (1991).

Lahti, J. M., Valentine, M., Xiang, J., Joens, B., Amann, J., Grenet, J., Richmond, G., Look, A. T., and Kidd, V. J., *Nature Genetics* 7:370–375 (1994).

Lahti, J. M., Xiang, J., Heath, L. S., Campana, D., and V. J. Kidd, *Mol. Cell. Biol.,* 15:1–11 (1995).

Lahue, E. E., Smith, A. V., and Orr-Weaver, T. L., *Genes & Development* 5: 2166–2175 (1991).

Leclerc, V., Tassan, J-P., O'Farrell, P., Nigg, E. A., and Leopold, P., *Molec. Biol. Cell* 7:505–513 (1996).

Leder et al., *Cell,* 45:485–495 (1986).

Lee, M. S., Ogg, O., Xu, M., Parker, L. L., Donoghue, D. J., Maller, J. L., and H. Piwnica-Worms, *Mol. Biol. Cell* 3:73–84 (1992).

Lees, E. and E. Harlow. *Mol. Cell. Biol.* 13:1194–1201 (1993).

Leopold, P. and O'Farrell, P. H., *Cell,* 66:1207–1216 (1991).

Lew, D. J., Dulic, V., and Reed, S. I., *Cell,* 66:1197–1206 (1991).

Li, H., Grenet, J., Valentine, M., Lahti, J. M., and Kidd, V. J., Gene 153: 237–242 (1995).

Li, H., Lahti, J. M., Valentine, M., Saito, M., Reed, S. I., Look, A. T., and Kidd, V. J. *Genomics,* 32:253–259 (1996a).

Liao, S-M., Zhang, J., Jeffery, D. A., Koleske, A. J., Thompson, C. M., Chao, D. M., Viljoen, M., vanVuuren, H. J. J., and Young, R. A., *Nature* 374, 193–196 (1995).

Lukas, J., L. Aagaard, M. Strauss, and J. Bartek, *Cancer Res.* 55:4818–4823 (1995).

Lukas, J., Parry, D., Aagaard, L., Mann, D. J., Bartkova, J., Strauss, M., Peters, G., and J. Bartek, *Nature,* 375:503–506 (1995).

Liu, Q., Neuhausen, S., McClure, M., Frye, C., Weaver-Feldhaus, J., Gruis, N. A., Eddington, K., Allalunis-Turner, M. J., Skolnick, M. H., Fujimura, F. K., and A. Kamb, *Oncogene,* 10:1061–1067 (1995).

MacDonald, *Hepatology* 7:425–515 (1984)).

Marion et al., *Biochem. Biophys. Res. Comm.* 113:967–974 (1983).

Mason et al., *Science* 234:1372–1378 (1985).

Matsushime, H., Ewen, M. E., Strom, D. K., Kato, J.-Y., Harks, S. K., Roussel, M. R., and C. J. Sherr, *Cell,* 71:323–334 (1992).

Matsushime, H., D. E. Quelle, S. A. Shurtleff, M. Shibuya, C. J. Sherr, and J. Kato, *Mol. Cell. Biol.,* 14:2066–2076 (1994).

Medema, R. H., Herrera, R. E., Lam, F., and R. A. Weinberg, *Proc. Natl. Acad. Sci., USA,* 92:6289–6293 (1995).

Meloche, S., Pages, G., and Pouyssegur, J., J Mol. Biol. Cell. 3:63–71 (1992). Merrifield, *J. Am. Chem. Soc.* 85:2149–2154 (1963).

Minshull, J., R. Golsteyn, C. S. Hill, and T. Hunt, *EMBO J.* 9:2865–2875 (1990).

Mogram et al., *Nature* 315:338–340 (1985).

Morgan, D. O., Nature, 374:131–134 (1995).

Nobori, T., K. Miura, D. -J Wu, A. Lois, K. Takabayashi, and D. A. Carson, *Nature,* 368:753–756 (1994).

O'Neill, E. M. and O'Shea, E. K., *Nature,* 374:121–122 (1995).

Ohtsubo, M., Theodoras, A.M., Schumacher, J., Roberts, J.M., and Pagano, M., *Mol. Cell. Biol.,* 15:2612–2624 (1995).

Okuda, T., Hirai, H., Valentine, V. A., Shurtleff, S. A., Kidd, V. J., Lahti, J. M., Sherr, C. J., and J. R. Downing, *Genomics,* 2:623–630 (1995).

Oliphant et al., *Gene* 44:177 (1986).

Ornitz et al., *Cold Spring Harbor Symp. Quant. Biol.* 50:399–409 (1986)

Osslpow, V., Tassan, J. P., Nigg, E. A., and V. Schibler, *Cell,* 83:137–146 (1995).

Parker, L. L., Atherton-Fessler, S., and H. Piwnica-Worms, *Proc. Natl. Acad. Sci., USA* 89:2917–2921 (1992).

Parry, D., S. Bates, D. J. Mann, and G. Peters, *EMBO J.,* 14:503–511 (1995).

Pearson et al., *Proc. Natl. Acad. Sci., USA* 85:2444–48 (1988).

Pelech, S. L. and J. S. Sanghera, *TIBS,* 17:233–238 (1992).

Pietenpol, J. A., Bohlander, S. K., Sato, Y., Papadopoulos, N., Liu, B., Friedman, C., Trask, B. J., Roberts, J. M., Kinzler, K. W., Rowley, J. D., and B. Vogelstein, *Cancer Res.* 55:1206–1210 (1995).

Pinkert et al., *Genes and Devel.* 1:268–276.

Polyak, K., Kato, J.-Y., Solomon, M. J., Sherr, C. J., Massague, J., Roberts, J. M., and A. Koff, *Genes & Devel.,* 8:9–22 (1994).

Prigogina, E. L., Puchkova, G. P., and Mayakova, S. A., *Cancer Genet & Cytogenetics,* 32:183–195 (1988).

Quelle, D. E., F. Zindy, R. A. Ashmun, and C. J. Sherr, *Cell* 83:993–1000 (1995).

Ranade, K., C. J. Hussussian, R. S. Sikorski, H. E. Varmus, A. M. Goldstein, M. A. Tucker, M. Serrano, G. J. Hannon, D. Beach, and N. C. Dracopoli, *Nature Gen.* 10:114–116 (1995).

Readhead et al., *Cell* 48:703–712(1987)).

Reeck et al., *Cell* 50:667 (1987).

Reed, J. A., F. Loganzo, C. R. Shea, G. J. Walker, J. F. Flores, J. M. Glendening, J. K. Bogdany, M. J. Shiel, F. G. Haluska, J. W. Fountain, and A. P. Albino, *Cancer Res.* 55:2713–2718 (1995).

Resnitzky, D., M. Gossen, H. Bujard, and S. I. Reed., *Mol. Cell. Biol.,* 14:1669–1679 (1992).

Rickert, P., W. Seghezzi, F. Shanahan, J-P. Tassan, E. A. Nigg, and E. Lees, *Keystone Symp.,* 1:61.(Abstract) (1996).

Rosenberg, C. L., H. G. Kim, T. B. Shows, H. M. Kronenberg, and A. Arnold, *Oncogene,* 6:449–453 (1991).

Rosenberg, C. L., E. Wong, E. M. Petty, A. E. Bale, Y. Tsujimoto, N. L. Harris, and A. Arnold, *Proc. Natl. Acad. Sci., USA,* 88:9638–9642 (1991).

Rosenblatt, J., Y. Gu, and D. 0. Morgan, Proc. Natl. Acad. Sci., USA, 89:2824–2828 (1992).

Roy, L. M., K. I. Swenson, D. H. Walker, B. G. Gabrielli, R. S. Li, H. Piwnica Worns, and J. L. Maller, *J. Cell Biol.,* 113:507–514 (1991).

Sani, *Nature* 314:283–286 (1985).

Serrano, M., G. J. Hannon, and D. Beach, *Nature* 366:704–707 (1993).

Sherr, C. J., Mammalian G1 cyclins. *Cell,* 73:1059–1065 (1993).

Sherr, C. J., *Trends Cell Biol.,* 4:15–18 (1993).

Sherr, C. J., *Cell,* 79:551–555 (1994).

Sherr, C. J. and J. M. Roberts, *Genes & Devel.,* 9:1149–1163 (1995).

Solomon, M. J., Harper, J. W., and J. Shuttleworth, *EMBO J.,* 12:3133–3142 (1993).

Stewart and Young, 1984, Solid Phase Synthesis, Second Edition, Pierce Chemical Co., Rockford, Ill.

Swift et al., *Cell* 38:639–646 (1984).

Tassan, J-P., Jaquenoud, M., Leopold, P., Schultz, S.J., and Nigg, E.A., *Proc. Natl. Acad. Sci., USA,* 92:8871–8875 (1995).

Villa-Kamaroff et al., *Proc. Natl. Acad Sci, USA* 75:3727–3731 (1978).

Wagner et al., *Proc. Natl. Acad. Sci., USA* 78:1441–1445 (1981).

Wu et al., *J. Biol. Chem.* 267:963–967 (1984).

Wu et al., *J. Biol. Chem.* 263:14621–14624(1988).

Xiang, J., Lahti, J.M., Grenet, J., Easton, J., and Kidd, V.J., *J. Biol. Chem.* 269:15786–15794 (1994).

Yamamoto et al., *Cell* 22:787–797 (1981).

Zoller et al., *DNA* 3:479–488 (1984).

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications in addition to the immediately foregoing are cited herein, the disclosures of which are incorporated by reference in their entireties.

What is claimed is:

1. An isolated amino acid polymer comprising the amino acid sequence of SEQ ID NO:4 or SEQ ID NO:4 comprising a conservative amino acid substitution.

2. An isolated amino acid polymer comprising the amino acid sequence of SEQ ID NO:52 or SEQ ID NO:52 comprising a conservative amino acid substitution.

3. The amino acid polymer of claim 1 comprising a detectable label.

4. An isolated amino acid polymer comprising the amino acid sequence of SEQ ID NO:50 or SEQ ID NO:50 comprising a conservative amino acid substitution.

5. An isolated amino acid polymer comprising the amino acid sequence of SEQ ID NO:3 or SEQ ID NO:3 comprising a conservative amino acid substitution.

6. The isolated amino acid polymer of claim 5 comprising the amino acid sequence of SEQ ID NO:3.

7. The amino acid polymer of claim 5 comprising a detectable label.

8. A fusion protein comprising the isolated amino acid polymer of claim 5.

9. The isolated amino acid polymer of claim 4 comprising the amino acid sequence of SEQ ID NO:50.

10. The amino acid polymer of claim 4 comprising a detectable label.

11. A fusion protein comprising the isolated amino acid polymer of claim 4.

12. The isolated amino acid polymer of claim 2 comprising the amino acid sequence of SEQ ID NO:52.

13. The amino acid polymer of claim 2 comprising a detectable label.

14. A fusion protein comprising the isolated amino acid polymer of claim 2.

15. The isolated amino acid polymer of claim 1 comprising the amino acid sequence of SEQ ID NO:4.

16. A fusion protein comprising the isolated amino acid polymer of claim 1.

17. An antigenic fragment of the human truncated cyclin C comprising 5 consecutive amino acids from amino acids 167–178 of SEQ ID NO:52.

18. A fusion peptide comprising the antigenic fragment of claim 17.

19. An antigenic fragment of the human truncated cyclin C comprising 5 consecutive amino acids from amino acids 286–325 of SEQ ID NO:50.

20. A fusion peptide comprising the antigenic fragment of claim 19.

* * * * *